(12) United States Patent
Plastow et al.

(10) Patent No.: US 12,213,464 B2
(45) Date of Patent: Feb. 4, 2025

(54) SINGLE NUCLEOTIDE POLYMORPHISMS AND FEEDING EFFICIENCY IN CATTLE

(71) Applicant: The Governors of the University of Alberta, Edmonton (CA)

(72) Inventors: Graham Plastow, Edmonton (CA); Mohammed Abo-Ismail, Edmonton (CA)

(73) Assignee: The Governors of the University of Alberta, Edmonton (CA)

( * ) Notice: Subject to any disclaimer, the term of this patent is extended or adjusted under 35 U.S.C. 154(b) by 675 days.

(21) Appl. No.: 16/757,505

(22) PCT Filed: Oct. 19, 2018

(86) PCT No.: PCT/CA2018/051326
§ 371 (c)(1),
(2) Date: Apr. 20, 2020

(87) PCT Pub. No.: WO2019/075577
PCT Pub. Date: Apr. 25, 2019

(65) Prior Publication Data
US 2021/0195876 A1 Jul. 1, 2021

Related U.S. Application Data

(60) Provisional application No. 62/574,925, filed on Oct. 20, 2017.

(51) Int. Cl.
*C12Q 1/68* (2018.01)
*A01K 67/027* (2006.01)
*C12P 19/34* (2006.01)
*C12Q 1/6876* (2018.01)

(52) U.S. Cl.
CPC .......... *A01K 67/027* (2013.01); *C12Q 1/6876* (2013.01); *A01K 2227/101* (2013.01); *C12Q 2600/124* (2013.01); *C12Q 2600/156* (2013.01)

(58) Field of Classification Search
CPC ............ C12Q 1/6883; C12Q 2600/124; C12Q 2600/156
See application file for complete search history.

(56) References Cited

FOREIGN PATENT DOCUMENTS

| CA | 2556911 | C | 12/2005 |
|---|---|---|---|
| CA | 2674297 | A1 | 7/2008 |
| CA | 2674298 | A1 | 7/2008 |
| CA | 2704208 | A1 | 5/2009 |

OTHER PUBLICATIONS

Wall, J.D. et al. "Haplotype Blocks and Linkage Disequilibrium in the Human Genome", Nature Reviews—Genetics, vol. 4, Aug. 2003, p. 587-597. (Year: 2003).*
Pennisi E. "A closer look at SNPs suggests difficulties" Science; Sep. 18, 1998; 281, 5384, p. 1787-1789. (Year: 1998).*
Rodrigues RT, et al. Differences in Beef Quality between Angus (*Bos taurus taurus*) and Nellore (*Bos taurus indicus*) Cattle through a Proteomic and Phosphoproteomic Approach. PLoS One. Jan. 19, 2017;12(1):e0170294. (Year: 2017).*
Bolormaa, S. et al. "Detection of quantitative trait loci in Bos indicus and Bos taurus cattle using genome-wide association studies". Genet Sel Evol 45, 43 (2013). (Year: 2013).*
Bolormaa et al., "A genome-wide association study of meat and carcass traits in Australian cattle1", J. Anim. Sci., vol. 89, pp. 2297-2309, 2011.
Enriquez-Valencia et al., "Effect of the g.98535683A> G SNP in the CAST gene on meat traits of Nellore beef cattle (*Bos indicus*) and their crosses with Bos taurus", Meat Science, vol. 123, pp. 64-66, 2017.
European Patent Office, "Supplementary Partial European Search Report", issued in connection to Application No. 18868315.5, 26 pages, mailed Aug. 5, 2021.
Gill et al., "Association of selected SNP with carcass and taste panel assessed meat quality traits in a commercial population of Aberdeen Angus-sired beef cattle", Genetics Selection Evolution, vol. 41, No. 36, pp. 1-12, 2009.
Islam et al., "Association analyses of a SNP in the promoter of IGF1 with fat deposition and carcass merit traits in hybrid, Angus and Charolais beef cattle", Animal Genetics, vol. 40, pp. 766-769, 2009.
Juszczuk-Kubiak et al., "The effect of polymorphisms in the intron 12 of CAST gene on meat quality of young bulls", Animal Science Papers and Reports, vol. 27, No. 4, pp. 281-292, 2009.
Maj et al., "Polymorphism in the 5'-noncoding region of the bovine growth hormone receptor gene and its association with meat production traits in cattle", Anim. Res., vol. 53, pp. 503-514, 2004.
Reardon et al., "Association of polymorphisms in candidate genes with colour, water-holding capacity, and composition traits in bovine M. longissimus and M. semimembranosus", Meat Science, vol. 86, pp. 270-275, 2010.
Soria et al., "Association of a novel polymorphism in the bovine PPARGC1A gene with growth, slaughter and meat quality traits in Brangus steers", Molecular and Cellular Probes, vol. 23, pp. 304-308, 2009.
Ujan et al., "Back fat thickness and meat tenderness are associated with a 526 T A mutation in the exon 1 promoter region of the MyF-5 gene in Chinese Bos taurus", Genetics and Molecular Research, vol. 10, No. 7, pp. 3070-3079, 2011.
Abo-Ismail et al., "Single nucleotide polymorphisms for feed efficiency and performance in crossbred beef cattle", BMC Genetics, vol. 15, 14 pages 2014.
Karisa et al., "Candidate genes and single nucleotide polymorphisms associated with variation in residual feed intake in beef cattle", J. Anim. Sci., vol. 91, pp. 3502-3513, Nov. 25, 2014.
The Canadian Patent Office, "The International Search Report and the Written Opinion of the International Searching Authority, or the Declaration" filed in connection with PCT/CA2018/051326 filed Oct. 19, 2018, 10 pages, mailed Feb. 19, 2019.

\* cited by examiner

*Primary Examiner* — Stephen T Kapushoc
(74) *Attorney, Agent, or Firm* — McKee, Voorhees & Sease, PLC

(57) ABSTRACT

Methods of identifying cattle having increased feed efficiency using a small panel of single nucleotide polymorphisms is provided. The method provides for using a thousand or less of such SNPs and includes using a panel of 250 or fewer SNPs. The method if useful with various cattle breeds including crossbred cattle. Provided are SNPs that are useful as markers with various traits associated with feed efficiency in cattle. Kits and methods of use are provided.

23 Claims, No Drawings

SINGLE NUCLEOTIDE POLYMORPHISMS AND FEEDING EFFICIENCY IN CATTLE

REFERENCE TO RELATED APPLICATION

This is a U.S. National Phase application claiming priority to PCT/CA18/51326, filed Oct. 19, 2018, which claims priority to previously filed and provisional application U.S. Ser. No. 62/574,925, filed Oct. 20, 2017, the contents of which are incorporated herein by reference in its entirety.

BACKGROUND

Selecting beef cattle for improved feed efficiency or low residual feed intake (RFI) has two direct benefits: reduced feed intake without compromising growth and product quality (Mao et al., 2013), and reducing the environmental footprint, particularly greenhouse gas emissions, per animal (Basarab et al., 2005; Manafiazar et al., 2016). These benefits can increase profitability for producers. Therefore, it is important to identify efficient animals and utilize them for production and breeding stock. A main challenge facing producers is to cost-effectively measure individual feed efficiency. Performance testing can be expensive and takes a long time before sufficient feed efficiency records can be accumulated to make them usable for selection purposes.

Utilizing genomics offers a potential alternative with several benefits including the ability to immediately predict feed efficiency at a young age. One of the preferred approaches to applying genomics for genetic improvement is genomic selection. This approach uses a reasonably dense set of single nucleotide polymorphisms (SNPs) (e.g. 50,000) evenly spaced across the genome (Meuwissen et al., 2001), and has been used very effectively for the Holstein breed (Hayes et al., 2009) and other species. However, to date, its routine use in crossbred beef cattle has been limited to more common breeds such as Angus and Simmental (Saatchi et al., 2014b) due to the large training populations required to establish selection criteria per breed. Additionally, estimates of marker effects differ between populations due to a number of factors, including linkage disequilibrium (e.g. where the marker phase differs in relation to causative mutations) (de Roos et al., 2009).

One option to overcome this problem is to identify causative mutations (or Quantitative Trait Nucleotides, QTN) associated with traits of interest, and to use a sufficient number of them to explain a useful proportion of the variation in the trait under consideration. In beef cattle, various studies have been used to identify genetic markers associated with feed efficiency including genome wide association studies (GWAS) (Sherman et al., 2008a; Sherman et al., 2009; Lu et al., 2013; Saatchi et al., 2014a) and the candidate gene approach (Sherman et al., 2008b; Abo-Ismail et al., 2013; Karisa et al., 2013; Abo-Ismail et al., 2014). These and other studies have reported a large number of SNPs associated with feed efficiency and its components traits. Nonetheless, these SNPs, genomic regions or candidate genes were not validated in other populations.

When identifying cattle for desirable characteristics, current practice involves using thousands of Single Nucleotide Polymorphisms (SNPs). As used herein a SNP or "single nucleotide polymorphism" refers to a specific site in the genome where there is a difference in DNA base between individuals. The SNP can act as an indicator to locate genes or regions of nucleotide sequences associated with a particular phenotype. As many as 10,000, 50,000, 80,000, 100,000 or even more SNPs would be analyzed in a sample from cattle at one time in order to determine if there is the presence or absence of a desired phenotype. Such large panels were considered necessary in order to assure a higher likelihood of detecting any mutation by relying upon linkages. A disadvantage of using such large panels is that the linkage may vary by breed, and thus a panel that detects mutation in one breed may not be useful in another breed. Also, this linkage decays after a few generations and prediction equations need to be updated. When referring to a panel in this context, a SNP profiling panel is meant, that is a selection or collection of SNPs used to analyze a biological sample for the presence of particular alleles of these the SNPs.

SUMMARY

Panels of single nucleotide polymorphisms are provided for use analyzing, selecting, feeding and breeding Bos sp. animals for feed efficiency. The panel sets out a small number of SNPs, including a panel 250 or less SNPs and in one example shows 54 markers within 34 genes associated with at least one trait associated with feed efficiency variation. The method may, in an embodiment comprises determining the genotype of the subject at a specific combination or sub-set of SNPs selected from those listed in Table 8. In embodiments, the method comprises determining the genotype of the subject of the SNPs listed in Table 2 or Table 3, or Table 4 or Table 5 or some of the SNPs at Tables 2-5 and 8 and/or only SNPs in linkage disequilibrium with one or more of the SNPs listed in Table 8. In an embodiment the 15 SNPs associated with Residual Feed Intake (RFI) and Residual Feed Intake (RFIf) adjusted for backfat listed in Table 2 are selected. In another embodiment, those SNPs associated with either Average Daily Gain (ADG), Dry Matter Intake (DMI), Midpoint Metabolic Weight (MMWT), or Backfat markers or any combination thereof are selected.

DESCRIPTION

Here, it has been discovered that considerably smaller panels of SNPs can be used in detecting feed efficiency in cattle. Here are shown examples to 1) identify SNPs located in genes within the regions reported to be associated with feed efficiency and to select SNPs with an increased likelihood of having a functional impact on the gene product or on gene expression; 2) to validate the association of SNPs with Residual Feed Intake (RFI) and its component traits using genetically distinct populations of beef cattle, and 3) to measure the proportion of variance explained by these SNPs in order to develop a low cost SNP panel to select for feed efficiency and its component traits.

The objective of this work was to develop and validate a customized cost-effective single nucleotide polymorphism (SNP) panel to select for feed efficiency in beef cattle. SNPs, identified in previous association studies and through analysis of candidate genomic regions and genes, were screened for their functional impact and allele frequency in Angus and Hereford breeds as candidates for the panel. Association analyses were performed on genotypes of 159 SNPs from new samples of Angus (n=160), Hereford (n=329) and Angus-Hereford crossbred (n=382) cattle using allele substitution and genotypic models in ASReml. Genomic heritabilities were estimated for feed efficiency traits using the full set of SNPs, SNPs associated with at least one of the traits (at P≤0.05 and P<0.10), as well as the Illumina bovine 50K representing a widely used commercial genotyping panel. A total of 63 SNPs within 43 genes showed association (P≤0.05) with at least one trait. The minor alleles of SNPs located in the GHR and CAST genes were associated with favorable effects on (i.e. decreasing) residual feed intake (RFI) and/or residual feed intake adjusted for backfat (RFI$_f$) whereas minor alleles of SNPs within MKI67 gene were associated with unfavorable effects on (i.e. increasing) RFI and RFI$_f$. Additionally, the minor allele of rs137400016 SNP within CNTFR was associated with increasing average daily gain (ADG). SNP genotypes within UMPS, SMARCAL, CCSER1 and LMCD1 genes showed significant overdominance effects whereas other SNPs located in SMARCAL1, ANXA2, CACNA1G, and PHYHIPL genes showed additive effects on RFI and RFI$_f$. Gene enrichment analysis indicated that gland development, as well as ion and cation transport are important physiological mechanisms contributing to variation in feed efficiency traits. The study revealed the effect of the Jak-STAT signaling pathway on feed efficiency through the CNTFR, OSMR, and GHR genes. Genomic heritability using the 63 significant (P≤0.05) SNPs was 0.09, 0.09, 0.13, 0.05, 0.05 and 0.07 for average daily gain, DMI, midpoint metabolic weight, RFI, RFI$_f$ and backfat, respectively. These SNPs explain up to 19% of genetic variation in these traits to be used to generate cost-effective molecular breeding values for feed efficiency in different breeds and populations of beef cattle.

The SNPs are effective across any breed because the SNPs are the mutation, or extremely close to the mutation so that they behave identically to a mutation, rather than relying upon linkages. In one embodiment the panel uses less than 1,000 SNPs, less than 250 SNPs and in other embodiments 200 or less, 150, 100, 95, 90, 85, 80, 75, 70, 65, 60, 55, 50, 45, 40, 35, 30, 25, 20, 15, 10, 5, or less and including amounts in-between, or even 1 SNP. Optionally, the method of this and other aspects of the invention may comprise determining the genotype of the bovine at 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55 or more of said SNPs. The method may, in some cases, comprise determining the genotype of the subject at a specific combination or sub-set of SNPs selected from those listed in Table 8, such as selecting one, two, three, four five, six or more of various SNPs set out in the table. In some cases, the method comprises determining the genotype of the subject at substantially all of the SNPs listed in Table 8. In some cases, the method comprises determining the genotype of the subject of the SNPs listed in Table 2 or Table 3, or Table 4 or Table 5 or some of the SNPs at Tables 2-5 and 8 and/or only SNPs in linkage disequilibrium with one or more of the SNPs listed in Table 8. In one embodiment all 159 SNPs are selected, in another 100 SNPs are selected, in yet another embodiment, some or all of the 54 SNPs of Table 2 are selected, in another, some or all of the 46 SNPs of Table 3 are selected, in another the 15 SNPs associated with Residual Feed Intake (RFI) and Residual Feed Intake (RFIf) adjusted for backfat listed in Table 2 are selected. In another embodiment, those SNPs associated with either Average Daily Gain (ADG), Dry Matter Intake (DMI), Midpoint Metabolic Weight (MMWT), or Backfat markers or any combination thereof are selected. By way of example, in table 2, 15 SNPs are associated with both RFI and RFIf, and additional SNPs listed in Table 3 associated with either RFI or RFIf. Tables 2 shows nine SNPs associated with DMI and 16 SNPs associated with ADG. Table 5 shows 16 SNPs associated with MMWT. Thus, any combination of the SNPs listed in Table 8, as well as those set out in Tables 2-5 may be used in a panel to test cattle.

In some embodiments, genetic markers associated with the invention are SNPs. In some embodiments the SNP is located in a coding region of a gene. In other embodiments the SNP is located in a noncoding region of a gene. In still other embodiments the SNP is located in an intergenic region. It should be appreciated that SNPs exhibit variability in different populations. In some embodiments, a SNP associated with the invention may occur at higher frequencies in some populations or breeds than in others. In some embodiments, SNPs associated with the invention are SNPs that are linked to feed efficiency or its component traits.

In certain embodiments a SNP associated with the invention is a SNP associated with a gene that is linked to feed efficiency. A SNP that is linked to feed efficiency may be identified experimentally. In one embodiment of the invention, further SNPs may be identified and added to a panel which includes the SNPs identified herein. In other embodiments a SNP that is linked to feed efficiency may be identified through accessing a database containing information regarding SNPs. Several non-limiting examples of databases from which information on SNPs or genes that are associated with bovines can be retrieved include NCBI resources, where organisms, including *Bos* sp. SNPs are collected and provided with identification numbers. See for example ncbi.nlm.nih.gov/projects/SNP/, The SNP Consortium LTD, NCBI dbSNP database, International HapMap Project, 1000 Genomes Project, Glovar Variation Browser, SNPStats, PharmGKB, GEN-SniP, and SNPedia. See also Sherry et al. (2001) "dbSNP: The NCBI database of genetic variation" Nucleic Acids Research, Vol. 29, Issue 1. In some embodiments, SNPs associated with the methods comprise two or more of the SNPs listed in Tables 2-5 and 8. In some embodiments 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 99, 100, 101, 102, 103, 104, 105, 106, 107, 108, 109, 110, 111, 112, 113, 114, 1115, 116, 117, 118, 119, 120, 121, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 1534, 154, 155, 156, 157, 158, 159, 160 or more SNPs are evaluated in a sample. In some embodiments, multiple SNPs are evaluated simultaneously while in other embodiments SNPS are evaluated separately.

SNPs are identified herein using the rs identifier numbers in accordance with the NCBI dbSNP database, which is publicly available at: http://www.ncbi.nlm.nih.gov/projects/SNP/. As used herein, rs numbers refer to the chromosome name and base pair position based on *Bos taurus* UMD 3.1.1 genome assembly. The rs # is informative for searching for the SNP in the dbSNP in NCBI to retrieve all information about each SNP Data for non-human variations is available through dbSNP (ftp.ncbi.nih.gov/snp/archive) and dbVar FTP sites, and after Sep. 1, 2017 new data is accepted at the European Variation Archive, through the European Bioinformatics Institute. See ebi.ac.uk/eva.

In some embodiments, SNPs in linkage disequilibrium with the SNPs associated with the processes are useful for obtaining similar results. As used herein, linkage disequilibrium refers to the non-random association of SNPs at two or more loci. Techniques for the measurement of linkage disequilibrium are known in the art. As two SNPs are in linkage disequilibrium if they are inherited together, the information they provide is correlated to a certain extent.

SNPs in linkage disequilibrium with the SNPs included in the models can be obtained from databases such as HapMap or other related databases, from experimental setups run in laboratories or from computer-aided in-silico experiments. Determining the genotype of a subject at a position of SNP as specified herein, e.g. as specified by NCBI dbSNP rs identifier, may comprise directly genotyping, e.g. by determining the identity of the nucleotide of each allele at the locus of SNP, and/or indirectly genotyping, e.g. by determining the identity of each allele at one or more loci that are in linkage disequilibrium with the SNP in question and which allow one to infer the identity of each allele at the locus of SNP in question with a substantial degree of confidence. In some cases, indirect genotyping may comprise determining the identity of each allele at one or more loci that are in sufficiently high linkage disequilibrium with the SNP in question so as to allow one to infer the identity of each allele at the locus of SNP in question with a probability of at least 90%, at least 95% or at least 99% certainty.

Feed efficiency refers to the efficiency with which the bodies of livestock convert animal feed into the desired output, such as meat or milk, for example. Examples of measurements of feed efficiency include residual feed intake (RFI) and/or residual feed intake adjusted for backfat (RFIf) which is the difference between actual feed intake of an animal and expected feed requirements for the maintenance and growth of the animal. A negative feed efficiency number reflects greater efficiency. Other measurements can be calculated from components which can include average daily gain (ADG), dry matter intake (DMI), midpoint metabolic weight (MMWT) and other combinations such as residual intake and gain. MMWT is the body weight at the middle of the performance testing period power 0.75. The MMWT presents the basal metabolizable energy required for maintenance of an animal.

Methods of Genotyping Animals

Any assay which identifies animals based upon here described allelic differences may be used and is specifically included within the scope of this disclosure. One of skill in the art will recognize that, having identified a causal polymorphism for a particular associated trait, or a polymorphism that is linked to a causal mutation, there are an essentially infinite number of ways to genotype animals for this polymorphism. The design of such alternative tests merely represents a variation of the techniques provided herein and is thus within the scope of this invention as fully described herein. See a discussion of such procedures as used in cattle at U.S. Pat. No. 8,008,011, incorporated herein by reference in its entirety. Illustrative procedures are described herein below.

Non-limiting examples of methods for identifying the presence or absence of a polymorphism include single-strand conformation polymorphism (SSCP) analysis, RFLP analysis, heteroduplex analysis, denaturing gradient gel electrophoresis, temperature gradient electrophoresis, ligase chain reaction and direct sequencing of the gene.

Non-limiting examples of amplification methods for identifying the presence or absence of a polymorphism include polymerase chain reaction (PCR), strand displacement amplification (SDA), nucleic acid sequence based amplification (NASBA), rolling circle amplification, T7 polymerase mediated amplification, T3 polymerase mediated amplification and SP6 polymerase mediated amplification.

Techniques employing PCR detection are especially advantageous in that detection is more rapid, less labor intensive and requires smaller sample sizes. Primers are designed to detect a polymorphism at the defined position. Primers that may be used in this regard may, for example, comprise regions of the sequence having the polymorphism and complements thereof. However, as is apparent, in order to detect a polymorphism at neither of the PCR primers in a primer pair need comprise regions of the polymorphism or a complement thereof, and both of the PCR primers in the pair may lie in the genomic regions flanking the genomic location of any of the SNP that may be present in cattle. However, preferably at least one primer of the oligonucleotide primer pair comprises at least 10 contiguous nucleotides of the nucleic acid sequence of including any of the SNP which may be present, or a complement thereof.

A PCR amplified portion of the sequence including the SNP can be screened for a polymorphism, for example, with direct sequencing of the amplified region, by detection of restriction fragment length polymorphisms produced by contacting the amplified fragment with a restriction endonuclease having a cut site altered by the polymorphism, or by SSCP analysis of the amplified region. These techniques may also be carried out directly on genomic nucleic acids without the need for PCR amplification, although in some applications this may require more labor.

Once an assay format has been selected, selections may be unambiguously made based on genotypes assayed at any time after a nucleic acid sample can be collected from an individual animal, such as a calf, or even earlier in the case of testing of embryos in vitro, or testing of fetal offspring.

As used herein, "Bos sp." means a *Bos taurus* or a *Bos indicus* animal, or a *Bos taurus/indicus* hybrid animal, and includes an animal at any stage of development, male and female animals, beef and dairy animals, any breed of animal and crossbred animals. Examples of beef breeds are Angus, Beefmaster, Hereford, Charolais, Limousin, Red Angus and Simmental. Examples of dairy breeds are Holstein-Friesian, Brown Swiss, Guernsey, Ayrshire, Jersey and Milking Shorthorn.

Any source of nucleic acid from an animal may be analyzed for scoring of genotype. Preferably, the nucleic acid used is genomic DNA. In one embodiment, nuclear DNA that has been isolated from a sample of hair roots, ear punches, blood, saliva, cord blood, amniotic fluid, semen, or any other suitable cell or tissue sample of the animal is analyzed. A sufficient amount of cells are obtained to provide a sufficient amount of DNA for analysis, although only a minimal sample size will be needed where scoring is by amplification of nucleic acids. The DNA can be isolated from the cells or tissue sample by standard nucleic acid isolation techniques.

In another embodiment samples of RNA, such as total cellular RNA or mRNA, may be used. RNA can be isolated from tissues by standard nucleic acid isolation techniques, and may be purified or unpurified. The RNA can be reverse transcribed into DNA or cDNA.

Hybridization of Nucleic Acids

The use of a probe or primer, preferably of between 10 and 100 nucleotides, preferably between 17 and 100 nucleotides in length, or in some aspects of the invention up to 1-2 kilobases or more in length, allows the formation of a duplex molecule that is both stable and selective. Molecules having complementary sequences over contiguous stretches greater than bases in length are generally preferred, to increase stability and/or selectivity of the hybrid molecules obtained. One will generally prefer to design nucleic acid molecules for hybridization having one or more complementary sequences of 20 to 30 nucleotides, or even longer where desired. Such fragments may be readily prepared, for example, by directly synthesizing the fragment by chemical means or by introducing selected sequences into recombinant vectors for recombinant production. The invention specifically provides probes or primers that correspond to or are a complement of a sequence that would include any SNP present or a portion thereof.

Accordingly, nucleotide sequences may be used in accordance with the invention for their ability to selectively form duplex molecules with complementary stretches of DNAs or to provide primers for amplification of DNA from samples. Depending on the application envisioned, one would desire to employ varying conditions of hybridization to achieve varying degrees of selectivity of the probe or primers for the target sequence.

For applications requiring high selectivity, one will typically desire to employ relatively high stringency conditions to form the hybrids. For example, relatively low salt and/or high temperature conditions, such as provided by about 0.02 M to about 0.10 M NaCl at temperatures of about 50° C. to about 70° C. Such high stringency conditions tolerate little, if any, mismatch between the probe or primers and the template or target strand.

For certain applications, lower stringency conditions may be preferred. Under these conditions, hybridization may occur even though the sequences of the hybridizing strands are not perfectly complementary, but are mismatched at one or more positions. Conditions may be rendered less stringent by increasing salt concentration and/or decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Hybridization conditions can be readily manipulated depending on the desired results.

In certain embodiments, it will be advantageous to employ nucleic acids of defined sequences with the present processes in combination with an appropriate means, such as a label, for determining hybridization. For example, such techniques may be used for scoring of RFLP marker genotype. A wide variety of appropriate indicator means are known in the art, including fluorescent, radioactive, enzymatic or other ligands, such as avidin/biotin, which are capable of being detected. In certain embodiments, one may desire to employ a fluorescent label or an enzyme tag such as urease, alkaline phosphatase or peroxidase, instead of radioactive or other environmentally undesirable reagents. In the case of enzyme tags, calorimetric indicator substrates are known that can be employed to provide a detection means that is visibly or spectrophotometrically detectable, to identify specific hybridization with complementary nucleic acid containing samples.

In general, it is envisioned that probes or primers will be useful as reagents in solution hybridization, as in PCR, for detection of nucleic acids, as well as in embodiments employing a solid phase. In embodiments involving a solid phase, the sample DNA is adsorbed or otherwise affixed to a selected matrix or surface. This fixed, single-stranded nucleic acid is then subjected to hybridization with selected probes under desired conditions. The conditions selected will depend on the particular circumstances (depending, for example, on the G+C content, type of target nucleic acid, source of nucleic acid, size of hybridization probe, etc.). Optimization of hybridization conditions for the particular application of interest is well known to those of skill in the art. After washing of the hybridized molecules to remove non-specifically bound probe molecules, hybridization is detected, and/or quantified, by determining the amount of bound label. Representative solid phase hybridization methods are disclosed in U.S. Pat. Nos. 5,843,663, 5,900,481 and 5,919,626. Other methods of hybridization that maybe used are disclosed in U.S. Pat. Nos. 5,849,481, 5,849,486 and 5,851,772. The relevant portions of these and other references identified in the specification are incorporated herein by reference.

Amplification of Nucleic Acids

Nucleic acids used as a template for amplification may be isolated from cells, tissues or other samples according to standard methodologies. Amplification can occur by any of a number of methods known to those skilled in the art.

The term "primer", as used herein, is meant to encompass any nucleic acid that is capable of priming the synthesis of a nascent nucleic acid in a template-dependent process. Typically, primers are short oligonucleotides from ten to twenty and/or thirty base pairs in length, but longer sequences can be employed. The primers are complementary to different strands of a particular target DNA sequence. This means that they must be sufficiently complementary to hybridize with their respective strands. Therefore, the primer sequence need not reflect the exact sequence of the template. Primers may be provided in double-stranded and/or single-stranded form, although the single-stranded form is preferred. Primers may, for example, comprise regions which include any SNP present and complements thereof.

Pairs of primers designed to selectively hybridize to nucleic acids are contacted with the template nucleic acid under conditions that permit selective hybridization. Depending upon the desired application, high stringency hybridization conditions may be selected that will only allow hybridization to sequences that are completely complementary to the primers. In other embodiments, hybridization may occur under reduced stringency to allow for amplification of nucleic acids containing one or more mismatches with the primer sequences. Once hybridized, the template-primer complex is contacted with one or more enzymes that facilitate template-dependent nucleic acid synthesis. Multiple rounds of amplification, also referred to as "cycles", are conducted until a sufficient amount of amplification product is produced.

The amplification product may be detected or quantified. In certain applications, the detection may be performed by visual means. Alternatively, the detection may involve indirect identification of the product via chemiluminescence, radioactive scintigraphy of incorporated radiolabel or fluorescent label or even via a system using electrical and/or thermal impulse signals (Affymax technology).

A number of template dependent processes are available to amplify the oligonucleotide sequences present in a given template sample. One of the best known amplification methods is the polymerase chain reaction (referred to as PCR™) which is described in detail in U.S. Pat. Nos. 4,683,195, 4,683,202 and 4,800,159, each of which is incorporated herein by reference in their entirety.

Other amplification techniques may comprise methods such as nucleic acid sequence based amplification (NASBA), rolling circle amplification, T7 polymerase mediated amplification, T3 polymerase mediated amplification and SP6 polymerase mediated amplification.

Another method for amplification is ligase chain reaction ("LCR"), disclosed in European Application No. 320,308, incorporated herein by reference in its entirety. U.S. Pat. No. 4,883,750 describes a method similar to LCR for binding probe pairs to a target sequence. A 10 method based on PCR™ and oligonucleotide ligase assay (OLA), disclosed in U.S. Pat. No. 5,912,148, also may be used.

An isothermal amplification method, in which restriction endonucleases and ligases are used to achieve the amplification of target molecules that contain nucleotide 5'-[α-thio]-triphosphates in one strand of a restriction site also may be useful in the amplification of nucleic acids (Walker et al, 1992).

Strand Displacement Amplification (SDA), disclosed in U.S. Pat. No. 5,916,779, is another method of carrying out isothermal amplification of nucleic acids which involves multiple rounds of strand displacement and synthesis, i.e., nick translation.

Detection of Amplified Nucleic Acids

Following any amplification, it may be desirable to separate the amplification product from the template and/or the excess primer. In one embodiment, amplification products are separated by agarose, agarose-acrylamide or polyacrylamide gel electrophoresis using standard methods. Separated amplification products may be cut out and eluted from the gel for further manipulation. Using low melting point agarose gels, the separated band may be removed by heating the gel, followed by extraction of the nucleic acid.

Separation of nucleic acids also may be affected by chromatographic techniques known in art. There are many kinds of chromatography which may be used, including adsorption, partition, ion-exchange, hydroxylapatite, molecular sieve, reverse-phase, column, paper, thin-layer, and gas chromatography as well as HPLC.

In certain embodiments, the amplification products are visualized. A typical visualization method involves staining of a gel with ethidium bromide and visualization of bands under UV light. Alternatively, if the amplification products are integrally labeled with radio- or fluorometrically-labeled nucleotides, the separated amplification products can be exposed to x-ray film or visualized under the appropriate excitatory spectra. Another typical method involves digestion of the amplification product(s) with a restriction endonuclease that differentially digests the amplification products of the alleles being detected, resulting in differently sized digestion products of the amplification product(s).

In one embodiment, following separation of amplification products, a labeled nucleic acid probe is brought into contact with the amplified marker sequence. The probe preferably is conjugated to a chromophore but may be radiolabeled. In another embodiment, the probe is conjugated to a binding partner, such as an antibody or biotin, or another binding partner carrying a detectable moiety.

In particular embodiments, detection is by Southern blotting and hybridization with a labeled probe. The techniques involved in Southern blotting are well known to those of skill in the art (see Sambrook et al, 1989). One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods disclosed.

Linkage with Another Marker

A genetic map represents the relative order of genetic markers, and their relative distances from one another, along each chromosome of an organism. During meiosis in higher organisms, the two copies of each chromosome pair align themselves closely with one another. Genetic markers that lie close to one another on the chromosome are seldom recombined, and thus are usually found together in the same progeny individuals ("linked"). Markers that lie close together show a small percent recombination, and are said to be "linked". Markers linked to loci that are associated with phenotypic effects (e.g., SNP's associated with phenotypic effects) are particularly important in that they may be used for selection of individuals having the desired trait. The identity of alleles at these loci can, therefore, be determined by using nearby genetic markers that are co-transmitted with the alleles, from parent to progeny. As such, by identifying a marker that is linked to such an allele, this will allow direct selection for the allele, due to genetic linkage between the marker and the allele. Particularly advantageous are alleles that are causative for the effect on the trait of interest Those of skill in the art will therefore understand that when genetic assays for determining the identity of the nucleotide at a defined position are referred to, this specifically encompasses detection of genetically linked markers (e.g., polymorphisms) that are informative for the defined locus. Such markers have predictive power relative to the traits related to feed efficiency, because they are linked to the defined locus. Such markers may be detected using the same methods as described herein for detecting the polymorphism at the defined locus. It is understood that these linked markers may be variants in genomic sequence of any number of nucleic acids, however SNP's are particularly preferred.

In order to determine if a marker is genetically linked to the defined locus, a lod score can be applied. A lod score, which is also sometimes referred to as $Z_{max}$, indicates the probability (the logarithm of the ratio of the likelihood) that a genetic marker locus and a specific gene locus are linked at a particular distance. Lod scores may e.g. be calculated by applying a computer program such as the MLINK program of the LINKAGE package (Lathrop et al., 1985; Am J. Hum Genet 37(3): 482-98). A lod score of greater than 3.0 is considered to be significant evidence for linkage between a marker and the defined locus. Thus, if a marker (e.g., polymorphism) and the g.-134 locus have a lod score of greater than 3, they are "linked".

Other Assays

Other methods for genetic screening may be used within the scope of the present disclosure, include denaturing gradient gel electrophoresis ("DGGE"), restriction fragment length polymorphism analysis ("RFLP"), chemical or enzymatic cleavage methods, direct sequencing of target regions amplified by PCR (see above), single-strand conformation polymorphism analysis ("SSCP") and other methods well known in the art.

Where amplification or extension is carried out on the microarray or bead itself, three methods are presented by way of example:

In the Minisequencing strategy, a mutation specific primer is fixed on the slide and after an extension reaction with fluorescent dideoxynucleotides, the image of the Microarray is captured with a scanner.

For cost-effective genetic diagnosis, in some embodiments, the need for amplification and purification reactions presents disadvantages for the on-chip or on-bead extension/amplification methods compared to the differential hybridization based methods. However, the techniques may still be used to detect and diagnose conditions.

Typically, Microarray or bead analysis is carried out using differential hybridization techniques. However, differential hybridization does not produce as high specificity or sensitivity as methods associated with amplification on glass slides. For this reason, the development of mathematical algorithms, which increase specificity and sensitivity of the hybridization methodology, are needed (Cutler et al.

Genome Research; 11:1913-1925 (2001). Methods of genotyping using microarrays and beads are known in the art. Some non-limiting examples of genotyping and data analysis can be found WO 2006/075254, which is hereby incorporated by reference. Testing, e.g. genotyping, may be carried out by any of the methods available such as those described herein, e.g. by microarray analysis as described herein. Testing is typically ex vivo, carried out on a suitable sample obtained from an individual.

Still another example is what is referred to as next-generation sequencing or genotype by sequencing. In such methods one may have a whole genome or targeted regions randomly digested into small fragments that are sequenced and aligned to a reference genome or assembled. This data can then be used to detect variants such as SNP, insertions and/or deletions (INDELS) and other variants such as copy number variants. These variations may then be used to identify sites with variation and/or genotype individual(s). For example, see WO2013/106737 and US20130184165. Variations available include those of Life Sciences Corporation as described in U.S. Pat. No. 7,211,390; Affymetrix Inc. as described in U.S. Pat. No. 7,459,275 and those by Hardin et al. US application 20070172869; to Lapidus et al. at US application US20077169560; Church et al. US application 20070207482, all of which are incorporated herein by reference in their entirety. A discussion is provided at Lin et al. (2008) "Recent Patents and Advances in the Next-Generation Sequencing Technologies" Recent Pat Biomed Eng. 2008(1):60-67, It will be evident to one skilled in the art there are many variations on approaches that may be taken, and which will be developed.

Kits

All the essential materials and/or reagents required for screening cattle for the defined allele may be assembled together in a kit. This generally will comprise a probe or primers designed to hybridize to the nucleic acids in the nucleic acid sample collected. Also included may be enzymes suitable for amplifying nucleic acids (e.g., polymerases such as reverse transcriptase or Taq polymerase), deoxynucleotides and buffers to provide the necessary reaction mixture for amplification. Such kits also may include enzymes and/or other reagents suitable for detection of specific nucleic acids or amplification products. Such reagents include, by way of example without limitation, enzymes, surfactants, stabilizers, buffers, deoxynucleotides, preservatives of the like. Embodiments provide the reagent is a detection reagent that identifies the presence or the SNP (such as through labeling via fluorescence or other chemical reaction) and/or an amplification reagent that amplifies nucleic acid. Embodiments provide for antibodies to be use a capture reagents. Such kits may be used with an isolated biological sample obtained from an animal.

Nucleic Acids and Proteins

In one aspect, the invention is an isolated DNA molecule comprising the SNP and sequences flanking, that is, adjacent to the SNP, or a variant or a portion thereof. This isolated DNA molecule, or variant or portion thereof may be used to synthesize a protein.

A nucleic acid molecule (which may also be referred to as a polynucleotide) can be an RNA molecule as well as DNA molecule, and can be a molecule that encodes for a polypeptide or protein, but also may refer to nucleic acid molecules that do not constitute an entire gene, and which do not necessarily encode a polypeptide or protein. The term DNA molecule generally refers to a strand of DNA or a derivative or mimic thereof, comprising at least one nucleotide base, such as, for example, a naturally occurring purine or pyrimidine base found in DNA (e.g., adenine "A", guanine "G" (or inosine "I), thymine "T" (or uracil "U"), and cytosine "C"). The term encompasses DNA molecules that are "oligonucleotides" and "polynucleotides". These definitions generally refer to a double-stranded molecule or at least one single-stranded molecule that comprises one or more complementary strand(s) r "complement(s)" of a particular sequence comprising a strand of the molecule.

"Variants" of DNA molecules have substantial identity to the sequences set forth in SEQ ID NO: 1 or SEQ ID NO: 6, including sequences having at least 70% sequence identity, preferably at least 75%, 80%, 85%, 90%, 95%, 96%, 97%, 98%, or 99% or higher sequence identity compared to a polynucleotide sequence of this invention using the methods described herein, (e.g., BLAST analysis, as described below).

Typically, a variant of a DNA molecule will contain one or more substitutions, additions, deletions and/or insertions, preferably such that the amino acid sequence of the polypeptide encoded by the variant DNA molecule is the same as that encoded by the DNA molecule sequences specifically set forth herein. It will be appreciated by those of ordinary skill in the art that, as a result of the degeneracy of the genetic code, there are many nucleotide sequences that may encode the same polypeptide. DNA molecules that vary due to differences in codon usage are specifically contemplated.

"Variants" of polypeptides and proteins have substantial identity to the sequences encoded including sequences having at least 90% sequence identity, preferably at least 95%, 96%, 97%, 98%, or 99% or higher sequence identity compared to an amino acid sequence of this invention using the methods described herein, (e.g., BLAST analysis, as described below).

Preference is given to introducing conservative amino acid substitutions at one or more of the predicted nonessential amino acid residues encoded by the DNA described here. A "conservative amino acid substitution" replaces the amino acid residue in the sequence by an amino acid residue with a similar side chain. Families of amino acid residues with similar side chains have been defined in the art. These families comprise amino acids with basic side chains (e.g. lysine, arginine, histidine), acidic side chains (e.g. aspartic acid, glutamic acid), uncharged polar side chains (e.g. glycine, asparagine, glutamine, serine, threonine, tyrosine, cysteine), nonpolar side chains (e.g. alanine, valine, leucine, isoleucine, proline, phenylalanine, methionine, tryptophan), beta-branched side chains (e.g. threonine, valine, isoleucine) and aromatic side chains (e.g. tyrosine, phenylalanine, tryptophan, histidine). A predicted nonessential amino acid residue in SEQ ID NO: 5 or 7 is thus preferably replaced by another amino acid residue of the same side-chain family. Other preferred variants may include changes to regulatory regions or splice site modifications.

In additional embodiments, the methods provide portions comprising various lengths of contiguous stretches of sequence identical to or complementary to that include the SNP and flanking sequences. Flanking sequences are those adjacent to the SNP. For example, DNA molecules are provided that comprise at least about 10, 15, 20, 30, 40, 50, 75, 100, 150, 200, 300, 400, or 500 or more contiguous nucleotides of the SNPs and their flanking sequences.

Percent sequence identity is calculated by determining the number of matched positions in aligned nucleic acid sequences, dividing the number of matched positions by the total number of aligned nucleotides, and multiplying by 100. A matched position refers to a position in which identical nucleotides occur at the same position in aligned nucleic acid sequences. Percent sequence identity also can be determined for any amino acid sequence. To determine percent sequence identity, a target nucleic acid or amino acid sequence is compared to the identified nucleic acid or amino acid sequence using the BLAST 2 Sequences (Bl2seq) program from the stand-alone version of BLASTZ containing BLASTN version 2.0.14 and BLASTP version 2.0.14. This stand-alone version of BLASTZ can be obtained on the U.S. government's National Center for Biotechnology Information web site (ncbi.nlm.nih.gov). Instructions explaining how to use the Bl2seq program can be found in the readme file accompanying BLASTZ.

Bl2seq performs a comparison between two sequences using either the BLASTN or BLASTP algorithm. BLASTN is used to compare nucleic acid sequences, while BLASTP is used to compare amino acid sequences. To compare two nucleic acid sequences, the options are set as follows: -i is set to a file containing the first nucleic acid sequence to be compared (e.g., C:\seq1.txt); -j is set to a file containing the second nucleic acid sequence to be compared (e.g., C:\seq2.txt); -p is set to blastn; -o is set to any desired file name (e.g., C:\output.txt); -q is set to -1; -r is set to 2; and all other options are left at their default setting. The following command will generate an output file containing a comparison between two sequences: C:\Bl2seq -i c:\seq1.txt -j c:\seq2.txt -p blastn -o c:\output.txt -q-1 -r 2. If the target sequence shares homology with any portion of the identified sequence, then the designated output file will present those regions of homology as aligned sequences. If the target sequence does not share homology with any portion of the identified sequence, then the designated output file will not present aligned sequences.

Once aligned, a length is determined by counting the number of consecutive nucleotides from the target sequence presented in alignment with sequence from the identified sequence starting with any matched position and ending with any other matched position. A matched position is any position where an identical nucleotide is presented in both the target and identified sequence. Gaps presented in the target sequence are not counted since gaps are not nucleotides. Likewise, gaps presented in the identified sequence are not counted since target sequence nucleotides are counted, not nucleotides from the identified sequence. The percent identity over a particular length is determined by counting the number of matched positions over that length followed by multiplying the resulting value by 100.

The DNA molecules may be part of recombinantly engineered constructs designed to express the DNA molecule, either as an RNA molecule or also as a polypeptide. In certain embodiments, expression constructs are transiently present in a cell, while in other embodiments, they are stably integrated into a cellular genome.

When creating probes, for example, methods well known to those skilled in the art may be used to construct expression vectors containing the DNA molecules of interest and appropriate transcriptional and translational control elements. These methods include in vitro recombinant DNA techniques, synthetic techniques, and in vivo genetic recombination. In one embodiment, expression constructs of the invention comprise polynucleotide sequences comprising all or a variant or a portion of the sequences described, to generate polypeptides that comprise all or a portion or a variant of encoded sequences.

Regulatory sequences present in an expression vector include those non-translated regions of the vector, e.g., enhancers, promoters, 5' and 3' untranslated regions, repressors, activators, and such which interact with host cellular proteins to carry out transcription and translation. Such elements may vary in their strength and specificity. Depending on the vector system and cell utilized, any number of suitable transcription and translation elements, including constitutive and inducible promoters, may be used. Expression vectors may also include sequences encoding polypeptides that will assist in the purification or identification of the polypeptide product made using the expression system.

A useful prokaryotic expression system is the pET Expression System 30 (Novagen™). This bacterial plasmid system contains the pBR322 origin of replication and relies on bacteriophage T7 polymerase for expression of cloned products. Host strains such as C41 and BL21 have bacteriophage T7 polymerase cloned into their chromosome. Expression of T7 pol is regulated by the lac system. Without the presence of IPTG for induction, the lac repressor is bound to the operator and no transcription occurs. IPTG titrates the lac repressor and allows expression of T7 pol, which then expresses the protein of interest on the plasmid. Kanamycin resistance is included for screening.

A useful eukaryotic expression system the pCI-neo Mammalian Expression Vector (Promega®), which carries the human cytomegalovirus (CMV) immediate-early enhancer/promoter region to promote constitutive expression of cloned DNA inserts in mammalian cells. This vector also contains the neomycin phosphotransferase gene, a selectable marker for mammalian cells. The pCI-neo Vector can be used for transient or stable expression by selecting transfected cells with the antibiotic G-418.

The identification of animals having the genotype identified allow decisions to be made with respect to an individual animal. The results can be used to sort feedlot animals by genotype to control the time to finishing and efficiency of feed use. Animals with the identified genotype can be fed lower amounts of feed or a different type of feed. Such animals may be particularly valuable for programs marketing beef or milk from "naturally-raised animals. Animals with an unfavorable genotype can be sorted and raised by using hormones or additives to promote more efficient growth. Further such animals with favorable genotypes may be used in a breeding program directed at optimization of feed use in a cattle herd.

Unless defined otherwise, technical and scientific terms used herein have the same meaning as commonly understood by one of ordinary skill in the art.

The term "locus" (plural loci) as used herein is a fixed position on a chromosome, and may or may not be occupied by one or more genes.

The term "allele" as used herein is a variant of the DNA sequence at a given locus.

The term "gene" is a functional protein, polypeptide, peptide-encoding unit, as well as non-transcribed DNA sequences involved in the regulation of expression. As will be understood by those in the art, this functional term includes genomic sequences, cDNA sequences, and smaller engineered gene segments that express, or is adapted to express, proteins, polypeptides, domains, peptides, fusion proteins, and mutants.

The term "genotype" or "genotypic" refers to the genetic constitution of an animal, for example, the alleles present at one or more specific loci. As used herein, the term "genotyping" refers to the process that is used to determine the animal's genotype.

The term "polymorphism" refers to the presence in a population of two (or more) allelic variants. Such allelic variants include sequence variation in a single base, for example a single nucleotide polymorphism (SNP).

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention. All references cited herein are incorporated herein by reference.

EXAMPLES

Example 1

SNP Panel Development and Design

Previous work identified significant associations among genomic regions or SNPs with feed efficiency in "discovery populations" of mainly crossbred or hybrid cattle (Karisa et al., 2013; Abo-Ismail et al., 2014). Additionally, a comprehensive literature search was completed to identify additional genes and SNPs reportedly associated with feed efficiency traits. These SNPs were then combined with those identified by screening sequences generated from the 1,000 Bulls Genome Project and the Canadian Cattle Genome Project (CCGP) (Daetwyler et al., 2014; Stothard et al., 2015). These resources were mined in silico to further improve the panel by seeking candidate genes within previously reported quantitative trait loci (QTL) (Hu et al., 2013) and polymorphisms predicted to impact gene function or expression using NGS-SNP (Grant et al., 2011). In addition, we selected genomic regions which had more than one candidate gene that were filtered based on their in-silico biological background using bioinformatics tools such as DAVID (Huang et al., 2009) to refine the list of genes to focus on those known to be involved in biological processes or pathways linked to feed efficiency. The impact of each polymorphism was assessed based on several criteria including SIFT (Sorting Intolerant From Tolerant) scores to predict whether amino acid substitutions significantly affected protein function (Ng and Henikoff, 2003). After initial filtering, we started with a set of 188,550 SNPs and focused on predicting functional variants in candidate genes that were segregating in Angus (AN) and Hereford (HH) cattle. Selected SNPs within genes known to be biologically linked to growth as well as lipid and energy metabolism were identified for consideration in the candidate SNP list. Allele frequency was also used to help select SNPs based on the data from the Canadian bulls (CCGP) in the 1,000 Bulls Genome Project (Daetwyler et al., 2014). By using minor allele frequency information from the previous step, the chance of detecting segregating causal mutations after genotyping is high. This would reduce the cost of genotyping non-segregating selected SNPs. The final selected list contained 250 SNPs to be used to optimise the multiplexes developed for this study. The number of multiplexes is a major factor in determining the final assay cost. See also Abo-Ismail, M. K., Lansink, N., Akanno, E., Karisa, B., Crowley, J. J., Moore, S., Bork, E., Stothard, P., Basarab, J.A., Plastow, G. (2018) Development and validation of a small SNP panel for feed efficiency in beef cattle. *J. Anim. Sci.* 96:375-397, (including FIGS. 1 and 2) the contents of which are incorporated herein by reference in its entirety.

Blood samples were collected by jugular venipuncture into evacuated tubes containing EDTA (Vacutainer, Becton Dickinson and Co., Franklin Lakes, New Jersey, USA) and refrigerated at 4° C. until DNA preparation. DNA extraction using the QiagenDNeasy 96 blood and tissue kit (Qiagen Sciences, Germantown, Maryland, USA) was performed by Delta Genomics (Edmonton, Alberta, Canada). The resulting samples were then used to develop multiplex sets for the Sequenom Mass-Array platform (San Diego, California, United States). The aim was to optimize the number of assays required to generate the maximum number of genotyped SNPs. The final panel design achieved by Sequenom resulted in assays for 216 SNPs. The panel was divided into 5 PCR based assays or multiplexes in order to generate genotypes for the 216 SNPs by Delta Genomics.

Animals and Phenotypic Data

All animals in the current study were cared for according to the guidelines of the Canadian Council on Animal Care (1993) and the protocols were approved by the University of Alberta Animal Use Committee. A set of animals born between 2002 and 2012 with accurate phenotypes for feed efficiency were identified from the Phenomic Gap project (PG1)(Crowley et al., 2014), initiated in 2008, primarily to generate phenotypic and genotypic information needed to discover and validate genome-wide selection methods and help address the issue of lack of data for traits difficult to measure in the Canadian beef cattle industry. Within the PG1 database, we selected AN, HH and crossbred (ANHH) animals (n=987), as these represented a population that was relatively genetically distinct from the research populations used for the initial SNP association studies at the Universities of Guelph and Alberta (Karisa et al., 2013; Abo-Ismail et al., 2014). Additionally, inclusion of crossbreds was considered more representative of the commercial beef industry, and which is therefore more likely to generate a panel useful in predicting feed efficiency for both purebred and commercial cattle. This made the selected population ideal to test our hypothesis (i.e. the tested SNPs could be used across breeds as well as crossbred herds).

The cattle in this study included HH bulls (n=284), replacement heifers (n=300), and finishing heifers (n=15), and steers (n=277). The AN and ANHH replacement heifers (n=300) were born from 2004 to 2012 and tested from 2005 to 2013 whereas the finished heifers were born in 2002, 2003 and 2011 and tested in 2003, 2004 and 2012 at the Lacombe Research Center (LRC). A detailed description of the breeding and management for the replacement and finishing heifers were described in previous studies (Basarab et al., 2011; Manafiazar et al., 2015). The ANHH steers were born in 2002 to 2010 at LRC. Additional information on the breeding and management of the ANHH steers was reported by Basarab et al. (2007) and Basarab et al. (2012). Briefly, heifers and steer calves were placed into separate feedlot pens each fitted with eight GrowSafe® (GrowSafe Systems Ltd., Airdrie, Alberta, Canada) feeding stations for the automatic monitoring of individual animal feed intake. The steers' finishing diet consisted of an average of 1% alfalfa silage, 22% barley silage, 70% barley grain and 7% supplement (as DMI basis; Table 8) and was fed ad libitum. The HH bulls were born in 2012 and tested at Olds College (n=164) and Cattleland (n=119) in 2012 and 2013. The bulls' test diet consisted of an average of 31-53% barley silage, 0-49% barley grain and 15-47% (chopped hay or beef developer pellet, respectively) (as DMI basis; Table 8). The feed intake testing protocol for the HH bulls was the same as in heifers and steer tests. Daily DMI was observed on all animals as well as frequent body weight measurements and ultrasound measurements at the start and end of test. From the performance test data, animals were tested for the following phenotypes: average daily gain (ADG), average daily dry matter intake (DMI), midpoint metabolic weight (MMWT), off test back fat (BFat), residual feed intake (RFI), and residual feed intake adjusted for back fat ($RFI_f$) (Table 1).

Genomic-Based Breed Composition and Retained Heterozygosity

Genomic-based breed composition was predicted using 43,172 SNPs distributed across the 29 autosomes from the Illumina Bovine 50K SNPs with ADMIXTURE software (Alexander et al., 2009) to account for stratification due to breed effects in the association analyses. A larger dataset (n=7845) of purebred animals of different breeds was used as a reference population. Additionally, the heterosis effect was accounted for in the association analyses, by calculating the genomic-based retained heterozygosity (RH) for each individual according to (Dickerson, 1973) as follows:

$$RH = 1 - \sum_{k=1}^{n} P_i^2 \qquad (1)$$

where P is the fraction of breed i from each of the n breeds.

Data Quality Control for the Developed Panel

A total of 987 animals were successfully genotyped for 216 SNPs. SNPs with call rates less than 70% (n=11), minor allele frequencies less than 1% (n=48), and excess of heterozygosity above 15%, were excluded from the analyses. Additionally, 20 animals with call rates less than 80% were excluded. Out of the initial 216 SNPs, 159 SNPs for 871 animals from AN (n=160), HH (n=329) and ANHH crossbred (n=382) cattle were considered for association analyses (Table 9).

Association Analysis

Three models were used to evaluate SNP associations, including allele substitution effects, as well as genotypic and additive/dominance models.

Allele substitution effect. Allele substitution effect is defined as the average change in phenotype value when the minor allele is substituted with the major allele. In order to estimate allele substitution effects for each SNP, genotypes were coded as 0, 1, or 2 corresponding to the number of minor alleles present using PLINK (Purcell et al., 2007). A univariate mixed model was fitted where phenotypes were regressed on the number of copies of the minor allele (0, 1, or 2) using ASReml 4 software (Gilmour et al., 2009). The mixed model was applied as follows:

$$Y_{ijk} = \mu + SNP_i + CG_j + \beta_1 AET + \beta_2 TL + \beta_3 AN + \beta_4 HH + \beta_5 RH + a_k + e_{ijk} \qquad (2)$$

where $Y_{jk}$ is the trait measured in the $k^{th}$ animal of the $j^{th}$ contemporary group; μ is the overall mean for the trait; $SNP_i$ is the fixed effect of the $i^{th}$ genotype for the SNP considered; $CG_j$ is the fixed effect of the $j^{th}$ gender, herd of origin, birth year, diet and management group; $\beta_1$ is the partial regression coefficient for age at the end of the test period (AET) of the $k^{th}$ animal; $\beta_2$ is the partial regression coefficient for test duration length (TL) of the $k^{th}$ animal; $\beta_3$ and $\beta_4$ are the partial regression coefficients for the genomic-based breed proportion of AN and HH breeds in the $k^{th}$ animal; $\beta_5$ is the regression coefficient of the linear regression on the percent of genomic-based retained heterozygosity of the $k^{th}$ animal; $a_k$ is the random additive genetic (polygenic) effect of the $k^{th}$ animal; and $e_{jklm}$ is the residual random effect associated with the $k^{th}$ animal record. Assumptions for this model are; $a_k$: a~N (0, A $\sigma^2$a) where A is a numerator relationship matrix, and $\sigma^2$a is the additive genetic variance; and $e_{ijk}$: e~(0, I $\sigma^2$e) where I is the identity matrix and $\sigma^2$e is the error variance. The expectations are that $E(a_k)$=0; and $E(e_{ijk})$=0; and the variances are $Var(a_k)$=$\sigma^2$a; $Var(e_{ijk})$=$\sigma^2$e. A$\sigma^2$a is the covariance matrix of the vector of animal additive genetic effects and the relationship matrix (A). Any contemporary group level that had less than three animals was excluded from the analysis. Phenotypic outliers were identified using Median Absolute Deviation method using R (Team, 2016) and excluded from the analysis.

Genoypic model: This model included the same effects as those in the allele substitution effect model, except that the allele substitution effect was replaced with the genotypes as a class variable (e.g. AA and BB for homozygous genotypes and AB for the heterozygous genotype). The least square means for each genotypic class was estimated.

Additive and dominance effect model. The additive and dominance effects of a SNP were estimated by fitting the substitution effect model as stated above and adding a covariate to the model with zeros for homozygous genotypes (coded 0 and 2) and ones for heterozygous genotypes (coded as 1) (Zeng et al., 2005). Thus, the linear regression coefficient of the substitution effect is the additive effect and the linear regression coefficient of the added covariate is the dominance effect for the SNP. For a SNP to be associated with a particular trait, the significance threshold of SNP association was 5% absolute P-value.

Gene Ontology and Pathway Enrichment Analyses

Enrichment analyses were performed to assign the associated candidate genes, those having at least one significant (P≤0.05) SNP, to predefined gene ontology (GO) terms and pathways based on their functional characteristics using the Database for Annotation, Visualization and Integrated Discovery (DAVID) v6.8 (Huang et al., 2009). The absolute P-value <0.05 was used to report the enriched GO terms and pathways. This relaxed threshold produces false positive results but may help in understanding the biological information about the candidate genes. To account for multi-hypotheses testing, the P-value of the enrichment analysis was adjusted using false discovery rate (FDR).

Heritability and Genetic Variance Explained by SNP Sets

Heritability was estimated using pedigree information and genomic-based methods. As the pedigree was available for all animals, the numerator relationship (A) matrix was constructed. The estimated breeding values (EBVs) for individuals and heritability of each trait were estimated using the univariate animal model in ASReml 4 software. To calculate the genomic based heritability, the genomic additive relationship matrix (G) was constructed following the formulas set out in (VanRaden, 2008). The genomic based heritability was calculated using the GREML method implemented in GVCBLUP software (Da et al., 2014) using different scenarios in terms of the number of SNPs; (1) all SNPs genotyped that passed quality control criteria in the small custom panel (n=158 SNPs), (2) a set of associated (P<0.05) SNPs with at least one of the feed efficiency traits (n=63 SNPs within 43 genes), (3) a set of associated (P<0.1) SNPs with at least one of the feed efficiency traits (n=92 SNPs), and (4) a set of SNPs (n=40465 SNPs) of the 50K SNP panel that passed quality control criteria. The proportion of genetic variance explained by the full list of SNPs was calculated by dividing the heritability calculated from GVCBLUP by the heritability estimated from the animal model.

RESULTS AND DISCUSSION

Association Analyses Using Allele Substitution Effect Model

A total of 54 markers within 34 genes were significantly ($P \leq 0.05$) associated with at least one phenotypic trait using an allele substitution effect regression model (Table 2). Furthermore, significant effects were identified for both feed efficiency traits (i.e. RFI and/or $RFI_f$) for 15 SNPs in 10 of the genes. The minor allele of SNPs within 8 of these genes (polycystin-2 (PKD2), calpastatin (CAST), calcium voltage-gated channel subunit alpha1 G (CACNA1G), occludin (OCLN), growth hormone receptor (GHR), proprotein convertase subtilisin/kexin type 6 (PCSK6), PAK1 interacting protein 1 (PAKIIP1) and phytanoyl-CoA 2-hydroxylase interacting protein like (PHYHIPL)) was associated with a negative, favorable, effect on RFI and/or $RFI_f$ (Table 2).

The minor alleles of three SNPs, rs137601357, rs210072660 and rs133057384, located in CAST were associated with decreases in RFI and $RFI_f$ (favorable effect). In addition, SNP rs384020496 in CAST was associated with MMWT, ADG, and Bfat, whereas SNP rs110711318 was associated with an increase in MMWT and Bfat (Table 2). The association of SNP rs384020496 with RFI was reported previously (Karisa et al., 2013). SNP rs137601357 is located 12 bases from SNP rs109727850 which had an additive effect on RFI (Karisa et al., 2013). Thus, the current results provide evidence that polymorphisms within CAST have important potential effects on feed efficiency and its component traits. The CAST gene is known to be associated with inhibition of the normal post-mortem tenderization of meat (Schenkel et al., 2006; Li et al., 2010). Additionally, the CAST gene can also play an important role in the metabolism of the live animal. For example, a previous study reported that during nutrient intake restriction, activity of the calpain system is upregulated by decreasing the expression level of CAST gene in bovine skeletal muscles, whereas the activity of the calpain system in a fetus is down-regulated through an increase in CAST expression maintaining fetal muscle growth during starvation (Du et al., 2004). Nonetheless, when selecting for favourable alleles for tenderness, this would be associated with higher protein metabolism (i.e. turnover) without negative effects on growth, efficiency, temperament, or carcass characteristics (Cafe et al., 2010).

The current study confirmed OCLN to be associated with RFI and $RFI_f$. The SNP rs134264563 within OCLN was associated with RFI and $RFI_f$. Another SNP rs109638814 within the OCLN gene was previously reported to be associated with RFI (Karisa et al., 2013), however, this was not the case in the current study. A previous study suggested an association between SNP rs134264563 and both cow as well as daughter conception rates in dairy cattle (Ortega et al., 2016). Although the SIFT values were 0.2 and 1 for rs134264563 and rs109638814, respectively, suggesting they are tolerated missense mutations, this may be in agreement with the hypothesis that when using QTN based selection (i.e. rs134264563), the SNP effect would be repeatable across different populations and breeds; this is in contrast to LD markers (i.e. rs109638814).

Our results indicated that a synonymous SNP rs110362902 within ABCG2 was associated with an increase in MMWT. The allele G of rs110362902 SNP was reported to be associated with increasing MMWT and decreasing intermuscular fat and marbling in beef cattle (Abo-Ismail et al., 2014). Additionally, SNP rs43702346 on BTA 6, within PKD2, was significantly associated with RFI, $RFI_f$ and MMWT, whereas substitution with the minor allele was associated with an increase of RFI, $RFI_f$ and MMWT, as well as a decrease in Bfat. These findings agreed with previous results reported for rs43702346 (Abo-Ismail et al., 2014) where substitution with the minor allele was associated with an increase in MMWT and a decrease in intermuscular fat percentage. The PKD2 gene is involved in negative regulation of G1/S transition of mitotic cell cycle process. Gene PKD2 is located near an identified QTL for bone percentage, fat percentage, meat percentage, meat to bone ratio, moisture content and subcutaneous fat (Gutiérrez-Gil et al., 2009). A SNP near to PKD2 (1063 Kbp) was associated with body weight in Australian Merino sheep (Al-Mamun et al., 2015). The results suggest that the SNP may be in linkage disequilibrium with a causative mutation associated with these traits.

Our findings indicated that the minor allele of tolerated missense mutations rs109065702, rs109808135, rs110348122 and rs208660945 within the SWI/SNF (SWItch/Sucrose Non-Fermentable)-related matrix associated actin-dependent regulator (SMARCAL1) gene were significantly associated with a decrease in $RFI_f$, whereas the minor allele of rs109382589, and having a deleterious mutation SIFT score=0.02, was associated with an increase of RFI and $RFI_f$. This study confirmed the significant association between rs109065702 (missense mutation) and RFI reported by Karisa et al. (2013). Furthermore, the minor allele of rs208660945 within SMARCAL1 was associated with a decrease in RFI and $RFI_f$ (favorable effect) and a decrease in ADG (unfavorable effect). The SMARCAL1 gene is involved in a network interacting with the Ubiquitin C (UBC) gene, which in turn, is involved in regulation of gene expression through DNA transcription, protein stability and degradation (Karisa et al., 2014).

The current results also revealed that the minor allele of the deleterious SNP rs476872493, within CACNA1G on BTA 19, was associated with decreasing RFI and $RFI_f$. SNP rs476872493 is located close to (23,710 bases) a synonymous SNP, rs41914675, which was reported to be associated with RFI, DMI and FCR (Abo-Ismail et al., 2014). These results lend support to the relationship between CACNA1G and feed efficiency traits. Feed efficiency was also associated with a deleterious SNP (rs385640152), within the GHR, gene where the minor allele was associated with favorable effects by decreasing RFI and $RFI_f$ (Table 2). SNP rs385640152 is located close to (18,371 bases) to SNP rs209676814, which was previously reported to have an over-dominant effect on RFI (Karisa et al., 2013). Another SNP in the 4[*1] intronic region was associated with RFI (Sherman et al., 2008b). The minor allele of the deleterious SNP rs43020736, within PCSK6, was associated with decreasing DMI, MMWT, RFI and $RFI_f$ (Table 2). This SNP was previously reported to affect DMI and RFI where animals with the C allele have lower DMI and RFI (Abo-Ismail et al., 2014). The current result is in agreement with the physiological role of PCSK6 as it is involved in apoptosis and other physiological processes (Wang et al., 2014). The results indicated that the marker of the proliferation Ki-67 (MKI67) gene harbours three SNPs (rs110216983, rs109930382 and rs109558734), which were associated with MMWT, DMI, RFI and $RFI_f$ (Table 2). The minor allele of these SNPs was associated with increasing MMWT, DMI, RFI and $RFI_f$. Other studies suggested that polymorphisms within MKI67 were associated with meat tenderness and meat quality traits in Blonde d'Aquitaine cattle (Ramayo-Caldas et al., 2016).

In total, minor alleles of 5 SNPs were associated with a decrease in DMI, while minor alleles of 4 SNPs were associated with an increase in DMI (Table 2). A positive effect (i.e. decreased feed intake) of the minor allele provides the greatest opportunity for improvement. However, the value depends on the actual frequency in the population of interest and markers with a frequency less than 0.8 associated with reduced intake are still expected to be useful for improvement, especially when combined into a molecular breeding value.

Genotypic and Additive & Dominance Models

The genotypes of 46 SNPs within 32 genes were associated (P≤0.05) with at least one feed efficiency trait or its component traits based on the genotypic model. Of these SNPs, 18 were associated with RFI and/or $RFI_f$ (Table 3). Four SNPs located in UMPS(rs110953962), SMARCAL1 (rs208660945), CCSER1 (rs41574929), and LMCD1 (rs208239648) genes showed significant overdominance effects on RFI and $RFI_f$ (Table 3). Other SNPs located in SMARCAL1 (rs109382589), ANXA2 (rs471723345), CACNA1G (rs476872493), and PHYHIPL (rs209765899) showed significant additive effects on RFI and $RFI_f$ (Table 3).

Three SNPs within MKI67 showed strong additive effects on RFI (Table 3). Additionally, in addition to the substantial effect reported previously, results characterized the effect of rs210072660 SNP located in CAST on RFI as significantly additive in decreasing RFI. The MKI67 and CAST genes have both been reported to affect meat quality traits, particularly meat tenderness (Schenkel et al., 2006; Ramayo-Caldas et al., 2016). The significant association between CAST and feed efficiency may explain the correlation between the selection of efficient animals (low RFI) and a negative effect on meat tenderness through the changes in calpastatin and myofibril fragmentation (McDonagh et al., 2001). Also, the significant association of MKI67 may explain the relationship between RFI and meat tenderness and related meat quality traits (Ramayo-Caldas et al., 2016) especially as these associations remained significant after adjusting RFI for fatness (i.e. $RFI_f$) (Table 3). These associations support the link between body composition and the true energetic efficiency of efficient animals (Richardson et al., 2001).

The genotypes of 9 SNPs within 6 genes were associated (P<0.05) with DMI (Table 4). Genotypes of three SNPs located in MKI67had significant additive effects on DMI (Table 4). Additionally, SNPs located in ERCC5 (rs133716845) and LMCD1 (rs208239648) showed significant dominance effects on DMI (Table 4). In a previous study, the rs133716845 SNP located in ERCC5 showed significant effects on carcass and meat quality traits by increasing lean meat yield and decreasing fatness (Abo-Ismail et al., 2014). A study in mice selected for high muscle mass found that ERCC5 was located in a QTL for lean mass (Kärst et al., 2011). Another sixteen SNPs were significantly associated with ADG and 12 SNPs showed additive effects (Table 4).

Genotypes of 9 SNPs located within 9 genes had significant associations with MMWT (Table 5). Out of these SNPs, 5 showed significant additive effects. For example, SNP rs133269500 within the thyroglobulin precursor (TG) gene showed an additive effect on MMWT (Table 5). These findings are in agreement with this gene's biological role as the precursor for thyroid hormones which control fat and lean deposition. A previous study reported polymorphisms in the 7G gene to have effects on growth and carcass composition (Zhang et al., 2015). Polymorphisms in 7G were associated with marbling score (Gan et al., 2008) and one of the commercially available DNA markers known as GeneSTAR MARB for evaluating marbling in beef cattle is in 7G (Rincker et al., 2006). The current results also found that rs110519795 SNP, a missense mutation, located in DPP6, showed a significant additive effect on MMWT, whereas SNP rs132717265 showed a significant additive effect on back fat (Table 5). The current associations are in agreement with the physiological role of DPP6 as the latter is involved in ion and cation transport, and which is reported to contribute to variation in feed efficiency (Richardson and Herd, 2004; Herd and Arthur, 2009). In a previous GWAS study in Angus and Simmental, as well as their crosses, an intronic SNP (rs110787048) located in DPP6, was reported to affect the efficiency of gain (i.e. residual average daily gain) (Serão et al., 2013). In another GWAS in Canchim beef cattle, DPP6 was reported to affect birth and weaning weights (Buzanskas et al., 2014). Another study suggested that polymorphisms within DPP6 had effects on the susceptibility of dairy cattle to *Mycobacterium bovis* infection (Richardson et al., 2016). SNPs located in the C27H8orf40 (rs135814528), ELMOD1 (rs42235500), MAPK15 (rs110323635), AFF3 (rs42275280), and PPM1K (rs134225543) genes all showed significant additive effects on backfat (Table 5).

Gene Ontology and Pathways Enrichment Analyses

Gland development. The gene set enrichment analysis suggested that the biological process of gland development (GO:0048732) was significantly enriched (P=0.0016) by the MKI67, PKD2, 7G and RB1CC1 genes (Table 6). Additionally, MKI67, PKD2 and RB1CC1 genes were each significantly (P<0.05) over-represented in liver development (GO:0001889) and mechanisms in the hepaticobiliary system (GO:0061008). The importance of these genes in organ development were presented in a study by Saatchi et al. (2014b) where the study identified 8 pleiotropic QTL's affecting body weights and carcass traits, and having genes involved in tissue development.

Ion transport (GO:0034220). The current results highlighted the importance of ion transport as a mechanism for controlling feed efficiency traits where it was promoted by DPP6, CNGA3, PKD2, ATP6V1E2, ANXA2, 7G and CACNA1G genes (Table 6). Previous studies have emphasised the importance of ion transport as part of the metabolic processes controlling variation in feed efficiency (Herd et al., 2004). Metabolism was reported to account for 42% variation in observed RFI (Herd and Arthur 2009).

Jak-STAT signaling pathway (bta04630). In the current study, JAK-STAT signaling was identified as a key pathway contributing to variation in feed efficiency traits. This pathway was enriched by the CNTFR, OSMR, and GHR genes (Table 6). Growth hormone binds its receptors (GHR) to activate the Janus kinases (Jaks) signal transduction pathway affecting important processes such as lipid metabolism and the cell cycle (Richard and Stephens, 2014). The mRNA expression of GHR is greater in the muscle and liver of efficient animals when compared to non-efficient animals (Chen et al., 2011; Kelly et al., 2013) where RFI was negatively associated with GHR expression (r=−0.5) (Kelly et al., 2013). The JAK-STAT pathway mediates several biological mechanisms including lipid and glucose metabolism, insulin signaling, development and adipogenesis regulation (Richard and Stephens, 2014). Other studies suggested that the GHR and OSMR genes repress adipocyte differentiation through an anti-adipogenic activity of STATS in different model systems (Richard and Stephens, 2014). This might explain the relationship between variation in RFI and body composition, especially body fat (Richardson et al., 2001; Richardson and Herd, 2004; Herd and Arthur, 2009).

Pedigree and Genomic Heritability and Genetic Variance Explained by SNP Panel

The pedigree-based heritability ($h_p^2$) estimates for feed efficiency traits in the current population were moderate to high, and ranged from 0.25 to 0.69 (Table 7). In general, the $h_p^2$ for the studied traits were in agreement with published values for Hereford and Angus populations (Schenkel et al., 2004). Generally, the estimated heritability for RFI (0.25) and RFI$_f$ (0.27) are within the reported range of 0.16 to 0.45 (Herd and Bishop, 2000; Crowley et al., 2010) in British Hereford and Irish beef cattle breeds. Also, the heritability (0.69) for MMWT agreed with that reported by Crowley et al. (2010). For DMI, heritability (0.49) was within previous estimates ranging from 0.31 to 0.49 (Herd and Bishop, 2000; Crowley et al., 2010). The fact that the heritability estimates calculated for feed efficiency traits were consistent with previously documented values support the use of the current population for estimating SNP effects and genomic heritability.

The genomic heritability using the different SNP sets ranged from 0.037 to 0.13 (Table 7). The associated ($P<0.05$) SNPs list explained 19.4% of the genetic variance of RFI and RFI$_f$ with genomic heritability of 0.05. Up to 32, 18, 18, 19.4, 19.4 and 15% of the genetic variance in average daily gain, DMI, midpoint metabolic weight, residual feed intake, and residual feed intake adjusted for back fat, respectively, were explained by the developed marker (n=159) panel or its subsets. About 16% of the genetic variance of the DMI was explained by the full SNP set in the panel tested. Interestingly, the highest genomic heritability for the full set of the developed markers (n=158) was for MMWT (0.13). This might support the link between candidate genes and the tissue development and energy maintenance mechanisms discussed previously. The population size used (n=871) in the current study was relatively low and the accuracy of prediction may improve as the number of individuals in the reference population increases (Goddard, 2009; VanRaden et al., 2009; Zhang et al., 2011). Candidate genes explained up to 19.4% in genetic variance in feed efficiency (RFI and RFI$_f$). Thus, using the SNP panel in marker assisted selection could be effective. Nonetheless, feed efficiency is a complex trait affected by many genes, and adding more informative SNPs to this panel would be needed to achieve the same proportion of genetic variance explained by a larger panel such as 50K SNP which explained 87% of genetic variance in feed efficiency in this study.

This study sought to generate and validate a set of SNPs selected to have a high chance of being causative mutations, or closely linked to such mutations (i.e. in linkage disequilibrium), which could have an effect on feed efficiency. Such SNPs would likely be useful for genetic improvement of feed efficiency across different populations of cattle or for selection in commercial crossbred populations which are prevalent in Canada. The results obtained are in good agreement with those from previous studies including those describing the roles of these genes and pathways in traits related to feed efficiency and its component traits. Generally, to develop a SNP panel as a selection tool, Crews et al. (2008) suggested it would be necessary to explain at least 10 to 15% of the genetic variation in order to be cost effective. Additionally, genomic selection is potentially cheaper than phenotypic selection especially if the number of SNPs on the panel is small and limited to only those with the largest effect (Zhang et al., 2011). More recently, it has been shown that including causative mutations or functional annotations of polymorphisms, can potentially improve the performance of genomic prediction (e.g. see (MacLeod et al., 2016). Thus, the current study incorporated biological information by selecting genes based on gene expression analyses, enriched data, and previously identified causal variants, to improve the power and precision of genomic prediction, including for crossbred or less related cattle populations. The current study also supports the value of incorporating variants from candidate genes reported in previous studies and known to be related to feed efficiency.

CONCLUSION

An informative cost-effective SNP marker panel was developed that predicted a useful proportion of variation in important feed efficiency traits for cattle. The study identified 63 SNP's associated with substantial variation (19.4%) in feed efficiency which can subsequently be used in practice by the beef industry. Such a panel with a small set of SNPs may be useful to generate molecular breeding values for feed efficiency at relatively low cost. Further testing in other populations including a wider variety of crossbred cattle is warranted. Some of the SNPs within the UMPS, SMARCAL, CCSER1 and LMCD1 genes showed significant over-dominance effects, whereas other SNPs located in the SMARCAL1, ANXA2, CACNA1G, and PHYHIPL genes showed additive effects on RFI and RFI$_f$. These results need to be taken into account in any cross breeding system to optimize useful allele combinations. Gland development, ion and cation transport were important physiological mechanisms contributing to variation in the feed efficiency traits. Finally, the study revealed the effect of a Jak-STAT signaling pathway on feed efficiency through the CNTFR, OSMR, and GHR genes which could be useful for genetic selection for feed efficiency.

Example 2

In this example a cow-calf producer will send in samples of his calves for genotyping.

These animals will then be assigned to one of three groups—efficient, average, and inefficient—based on their molecular breeding values (MBVs), where efficient represents the top 16% of the herd (within >+1 standard deviation), average represents the middle 68% (e.g., within +/−1 standard deviation from the mean of a normal distribution), and inefficient represents the bottom 16% (within <−1 standard deviation). The MBVs in this example were calculated using the estimates of allele substitution effects (ASEs) found in the first example. (See Table 2). Molecular breeding value is a value assigned to an animal by adding the estimate of allele substitution effect for one or more traits. In an embodiment the MBV is based upon a combination of one or more of the estimates of allele substitution effects (ASEs) in Table 2. These estimated values may be compared to actual feeding data from cattle. Part of the population of animals can be placed into these groups based upon their molecular breeding value. A panel consisting of 62 SNPs from Table 8 were analyzed using genotypes from the animals listed in Table 10.

Note these estimates may be improved over time as more data is added to the training population. However, the validation population used in the example results from a population with breed composition including Angus (50%), Charolais (14%), Hereford (10%), and Limousin (6%) indicating that the panel should be useful for predicting the efficiency of crossbred animals which is the challenge addressed by the invention. In addition, these estimates may be improved by assigning genomic breed composition to the test samples in order to choose which animals are selected from the training population to customize the estimates to the specific herd being tested.

Here a total of 391 animals with available residual feed intake corrected for back fat ($RFI_f$) phenotypes were genotyped for 62 SNPs from Table 2 (as above).

These SNPs were chosen as having significant associations with feed efficiency traits, although not necessarily $RFI_f$ and all ASEs were used whether significant or not. A person of skill in the art appreciates that this type of data can be employed in analysing different traits.

In order to show how the panel would be used in practice, we used the predicted ASE for each SNP to classify the animals into 3 groups—efficient, average, and inefficient—according to the proportions of 16%, 68% and 16%, described above, of the population using the MBV. Data on the actual feed efficiency phenotype of the animals was concealed for the prediction calculation.

In the next step, the actual performance of the animals assigned to each group was compared using the animals' own records in terms of the cost of feeding. In this case (using dry matter intake) it was found that the efficient group generated a reduction in cost of feed of $1,332.64 for a group of 50 animals (i.e. $26.65 per head) over 265 days. This compared to the reduction in cost of feed from the average groups of $526.40 for a group of 50 animals (i.e. $10.53 per head) compared to the inefficient group.

If the producer is interested in keeping replacement animals to improve the performance of the next generation, it can be seen that he will be able to improve the performance of his herd by using the MBVs to select these replacements.

If we assume that half of the value will be passed onto their progeny (e.g., 50% of the genes from each parent is passed to each offspring, on average) then he will generate an extra $5 per head from the efficient animals compared to the average of the herd. Based on the information garnered, producers could choose to keep top animals for future breeding or cull the bottom animals from the breeding program.

Example 3

The independent population of animals described in Example 2 and listed in Table 10 were used to determine the associations with feed efficiency traits. These animals were genotyped with a small panel of the SNPs from Table 8. A total of 62 SNPs were genotyped and analyzed for trait associations as done previously. Thirty (34) of these SNPs were significant for at least one of the traits (p<0.1) (See Table 11.) Note all these SNPs were used for the calculation of the prediction of the efficient, average, and inefficient animals in Example 2. Using the information for the markers shown in Table 2, these markers were assigned significant effects for 51 (P<0.1) trait-marker combinations. In this dataset there were 10 that overlapped between both datasets, and a total of 26 trait marker combinations that were significant for these new animals. A total of 41 had p-values <0.2. Those with skill in the art would understand these markers have utility.

The results support the use of these markers in predicting feed efficiency traits for different populations of commercial cattle. Further it illustrates the approaches used to refine the number of SNPs required for a panel to be effective in each specific population.

Example 4

As indicated previously it is possible to choose the best set of SNPs for a particular population or customer by testing for associations with available SNPs identified as potential QTN.

In this example the samples available in Table 10 were tested with 28 additional SNPs selected from Table 8.

To determine their utility in this sample of animals these 28 SNPs were used to replace 28 of the non-significant SNPs in the panel tested in Example 3. The panel tested contained 62 SNPs—34 found to be significant from Table 11 and 28 selected from Table 8. As expected in this case the new panel explained a greater proportion of the genetic variance for each trait. With this proportion doubling for RFI and DMI In a second analysis 11 SNPs from Table 8 were added to 61 SNPs used in Example 2 to make a new panel of 72 SNPs (one of the SNPs tested in Example 2 was removed). Although the proportion of genetic variance explained for RFI was approximately the same as in Example 2, the prediction for DMI was improved nearly two fold. See Table 12 where markers used for Examples 3 and 4 are identified in columns L and M.

Example 5

In order to illustrate how additional SNPs can be generated to be added to these small panels, we genotyped the animals listed in Table 10 with a commercial high density panel (with more than 220,000 SNPs): the GGP F-250 from Neogen. See http://genomics.neogen.com/en/ggp-f-250-beef and the PDF fact sheet http://genomics.neogen.com/pdf/ag265_ggp_f-250.pdf. The top 20 SNPs were determined for DMI and RFI by determining their effects in these animals (Table 13). These SNPs were then combined with the top 55 SNPs from Example 4 to generate a panel of 75 SNPs. Each new panel explained a large proportion of the genetic variance in DMI (40%) and RFI (57%). After validation of the top 20 SNPs in unrelated populations, the combination of these panels would generate a panel of 95 SNPs suitable to predict DMI and RFI together. Such customized small panels have the potential to predict these traits with relatively high accuracy at a significantly lower cost than the commercial high density panel.

LITERATURE CITED

Abo-Ismail, M., M. Kelly, E. Squires, K. Swanson, S. Bauck, and S. Miller. 2013. Identification of single nucleotide polymorphisms in genes involved in digestive and metabolic processes associated with feed efficiency and performance traits in beef cattle. Journal of animal science 91(6):2512-2529.

Abo-Ismail, M. K., G. Vander Voort, J. J. Squires, K. C. Swanson, I. B. Mandell, X. Liao, P. Stothard, S. Moore, G. Plastow, and S. P. Miller. 2014. Single nucleotide polymorphisms for feed efficiency and performance in crossbred beef cattle. BMC genetics 15(1):1.

Al-Mamun, H. A., P. Kwan, S. A. Clark, M. H. Ferdosi, R. Tellam, and C. Gondro. 2015. Genome-wide association study of body weight in Australian Merino sheep reveals an orthologous region on OAR6 to human and bovine genomic regions affecting height and weight. Genetics Selection Evolution 47(1):66.

Alexander, D. H., J. Novembre, and K. Lange. 2009. Fast model-based estimation of ancestry in unrelated individuals. Genome research 19(9):1655-1664.

Basarab, J., V. Baron, Ó. López-Campos, J. Aalhus, K. Haugen-Kozyra, and E. Okine. 2012. Greenhouse gas emissions from calf- and yearling-fed beef production systems, with and without the use of growth promotants. Animals 2(2):195-220.

Basarab, J., M. Colazo, D. Ambrose, S. Novak, D. McCartney, and V. Baron. 2011. Residual feed intake adjusted for backfat thickness and feeding frequency is independent of fertility in beef heifers. Canadian Journal of Animal Science 91(4):573-584.

Basarab, J. A., D. McCartney, E. K. Okine, and V. S. Baron. 2007. Relationships between progeny residual feed intake and dam productivity traits. Canadian Journal of Animal Science 87(4):489-502. doi: 10.4141/CJAS07026

Basarab, J. A., E. K. Okine, V. S. Baron, T. Marx, P. Ramsey, K. Ziegler, and K. Lyle. 2005. Methane emissions from enteric fermentation in Alberta's beef cattle population. Canadian Journal of Animal Science 85(4):501-512. doi: 10.4141/A04-069

Buzanskas, M. E., D. A. Grossi, R. V. Ventura, F. S. Schenkel, M. Sargolzaei, S. L. C. Meirelles, F. B. Mokry, R. H. Higa, M. A. Mudadu, M. V. G. B. da Silva, S. C. M. Niciura, R. A. A. T. Junior, M. M. Alencar, L. C. A. Regitano, and D. P. Munari. 2014. Genome-Wide Association for Growth Traits in Canchim Beef Cattle. PLOS ONE 9(4):e94802. doi: 10.1371/journal.pone.0094802

Cafe, L. M., B. L. McIntyre, D. L. Robinson, G. H. Geesink, W. Barendse, and P. L. Greenwood. 2010. Production and processing studies on calpain-system gene markers for tenderness in Brahman cattle: 1. Growth, efficiency, temperament, and carcass characteristics1. Journal of Animal Science 88(9):3047-3058. doi: 10.2527/jas.2009-2678

Chen, Y., C. Gondro, K. Quinn, R. M. Herd, P. F. Parnell, and B. Vanselow. 2011. Global gene expression profiling reveals genes expressed differentially in cattle with high and low residual feed intake. Animal Genetics 42(5):475-490. doi: 10.1111/j.1365-2052.2011.02182.x Crews, D., S. Moore, and R. Enns. 2008. Optimizing traditional and marker assisted evaluation in beef cattle. Proceedings of the 40th Beef Improvement Federation, Calgary, Alberta:44-49.

Crowley, J. J., M. McGee, D. A. Kenny, D. H. Crews, R. D. Evans, and D. P. Berry. 2010. Phenotypic and genetic parameters for different measures of feed efficiency in different breeds of Irish performance-tested beef bulls. Journal of Animal Science 88(3):885-894. doi: 10.2527/jas.2009-1852

Crowley, J. J., P. Stothard, J. A. Basarab, S. P. Miller, C. Li, Z. Wang, G. Plastow, E. De Pauw, S. S. Moore, and D. Lu. 2014. Collation of Data and Genetic Parameter Estimation in Different Experimental Canadian Beef Cattle Populations Measured for Feed Efficiency 10th World Congress on Genetics Applied to Livestock Production (WCGALP). p Paper 117, Vancouver, Canada.

Da, Y., C. Wang, S. Wang, and G. Hu. 2014. Mixed Model Methods for Genomic Prediction and Variance Component Estimation of Additive and Dominance Effects Using SNP Markers. PLOS ONE 9(1):e87666. doi: 10.1371/journal.pone.0087666

Daetwyler, H. D., A. Capitan, H. Pausch, P. Stothard, R. van Binsbergen, R. F. Brondum, X. Liao, A. Djari, S. C. Rodriguez, C. Grohs, D. Esquerre, O. Bouchez, M.-N. Rossignol, C. Klopp, D. Rocha, S. Fritz, A. Eggen, P. J. Bowman, D. Coote, A. J. Chamberlain, C. Anderson, C. P. VanTassell, I. Hulsegge, M. E. Goddard, B. Guldbrandtsen, M. S. Lund, R. F. Veerkamp, D. A. Boichard, R. Fries, and B. J. Hayes. 2014. Whole-genome sequencing of 234 bulls facilitates mapping of monogenic and complex traits in cattle. Nat Genet 46(8):858-865. (Article) doi: 10.1038/ng.3034 de Roos, A. P. W., B. J. Hayes, and M. E. Goddard. 2009. Reliability of Genomic Predictions Across Multiple Populations. Genetics 183(4):1545. (10.1534/genetics.109.104935)

Dickerson, G. E. 1973. Inbreeding and heterosis in animals. Journal of Animal Science 1973 (Symposium):54-77.

Du, M., M. J. Zhu, W. J. Means, B. W. Hess, and S. P. Ford. 2004. Effect of nutrient restriction on calpain and calpastatin content of skeletal muscle from cows and fetuses1. Journal of Animal Science 82(9):2541-2547. doi: 10.2527/2004.8292541x Gan, Q.-F., L.-P. Zhang, J.-Y. Li, G.-Y. Hou, H.-D. Li, X. Gao, H.-Y. Ren, J.-B. Chen, and S.-Z. Xu. 2008. Association analysis of thyroglobulin gene variants with carcass and meat quality traits in beef cattle. Journal of Applied Genetics 49(3):251-255. (journal article) doi: 10.1007/bf03195621

Gilmour, A., B. J. Gogel, B. Cullis, and R. Thompson. 2009. ASReml User Guide Release 3.0. VSN International Ltd Hemel Hempstead, HP1 1ES, UK.

Goddard, M. 2009. Genomic selection: prediction of accuracy and maximisation of long term response. Genetica 136(2):245-257.

Grant, J. R., A. S. Arantes, X. Liao, and P. Stothard. 2011. In-depth annotation of SNPs arising from resequencing projects using NGS-SNP. Bioinformatics 27(16):2300-2301.

Gutiérrez-Gil, B., J. Williams, D. Homer, D. Burton, C. Haley, and P. Wiener. 2009. Search for quantitative trait loci affecting growth and carcass traits in a cross population of beef and dairy cattle. Journal of animal science 87(1):24-36.

Hayes, B. J., P. J. Bowman, A. J. Chamberlain, and M. E. Goddard. 2009. <em>Invited review</em>: Genomic selection in dairy cattle: Progress and challenges. Journal of Dairy Science 92(2):433-443. doi: 10.3168/jds.2008-1646

Herd, R., and P. Arthur. 2009. Physiological basis for residual feed intake. Journal of animal science 87(14_suppl):E64-E71.

Herd, R., V. Oddy, and E. Richardson. 2004. Biological basis for variation in residual feed intake in beef cattle. 1. Review of potential mechanisms. Animal Production Science 44(5):423-430.

Herd, R. M., and S. C. Bishop. 2000. Genetic variation in residual feed intake and its association with other production traits in British Hereford cattle. Livestock Production Science 63(2):111-119. doi: http://dx.doi.org/10.1016/S0301-6226(99)00122-0

Hu, Z.-L., C. A. Park, X.-L. Wu, and J. M. Reecy. 2013. Animal QTLdb: an improved database tool for livestock animal QTL/association data dissemination in the post-genome era. Nucleic Acids Research 41 (Database issue): D871-D879. doi: 10.1093/nar/gks1150

Huang, D. W., B. T. Sherman, and R. A. Lempicki. 2009. Systematic and integrative analysis of large gene lists using DAVID bioinformatics resources. Nature protocols 4(1):44-57.

Karisa, B., S. Moore, and G. Plastow. 2014. Analysis of biological networks and biological pathways associated with residual feed intake in beef cattle. Animal Science Journal 85(4):374-387. doi: 10.1111/asj.12159

Karisa, B., J. Thomson, Z. Wang, P. Stothard, S. Moore, and G. Plastow. 2013. Candidate genes and single nucleotide polymorphisms associated with variation in residual feed intake in beef cattle. Journal of animal science 91(8): 3502-3513.

Kärst, S., R. Cheng, A. O. Schmitt, H. Yang, F. P. M. De Villena, A. A. Palmer, and G. A. Brockmann. 2011. Genetic determinants for intramuscular fat content and water-holding capacity in mice selected for high muscle mass. Mammalian genome 22(9-10):530.

Kelly, A. K., S. M. Waters, M. McGee, J. A. Browne, D. A. Magee, and D. A. Kenny. 2013. Expression of key genes of the somatotropic axis in longissimus dorsi muscle of beef heifers phenotypically divergent for residual feed intake. Journal of Animal Science 91(1):159-167. doi: 10.2527/jas.2012-5557

Li, J., L.-P. Zhang, Q.-F. Gan, J.-Y. Li, H.-J. Gao, Z.-R. Yuan, X. Gao, J.-B. Chen, and S.-Z. Xu. 2010. Association of CAST Gene Polymorphisms with Carcass and Meat Quality Traits in Chinese Commercial Cattle Herds. Asian-Australas J Anim Sci 23(11):1405-1411. doi: 10.5713/ajas.2010.90602

Lu, D., S. Miller, M. Sargolzaei, M. Kelly, G. Vander Voort, T. Caldwell, Z. Wang, G. Plastow, and S. Moore. 2013. Genome-wide association analyses for growth and feed efficiency traits in beef cattle1. Journal of Animal Science 91(8):3612-3633. doi: 10.2527/jas.2012-5716

MacLeod, I. M., P. J. Bowman, C. J. Vander Jagt, M. Haile-Mariam, K. E. Kemper, A. J. Chamberlain, C. Schrooten, B. J. Hayes, and M. E. Goddard. 2016. Exploiting biological priors and sequence variants enhances QTL discovery and genomic prediction of complex traits. BMC Genomics 17(1):144. (journal article) doi: 10.1186/s12864-016-2443-6

Manafiazar, G., J. Basarab, V. Baron, L. McKeown, R. Doce, M. Swift, M. Undi, K. Wittenberg, and K. Ominski. 2015. Effect of post-weaning residual feed intake classification on grazed grass intake and performance in pregnant beef heifers. Canadian journal of animal science 95(3):369-381.

Manafiazar, G., S. Zimmerman, and J. Basarab. 2016. Repeatability and variability of short-term spot measurement of methane and carbon dioxide emissions from beef cattle using GreenFeed emissions monitoring system. Canadian Journal of Animal Science 97(1):118-126.

Mao, F., L. Chen, M. Vinsky, E. Okine, Z. Wang, J. Basarab, D. Crews, and C. Li. 2013. Phenotypic and genetic relationships of feed efficiency with growth performance, ultrasound, and carcass merit traits in Angus and Charolais steers. Journal of Animal Science 91(5):2067-2076.

McDonagh, M., R. Herd, E. Richardson, V. Oddy, J. Archer, and P. Arthur. 2001. Meat quality and the calpain system of feedlot steers following a single generation of divergent selection for residual feed intake. Animal Production Science 41(7):1013-1021.

Meuwissen, T. H. E., B. J. Hayes, and M. E. Goddard. 2001. Prediction of Total Genetic Value Using Genome-Wide Dense Marker Maps. Genetics 157

Ng, P. C., and S. Henikoff. 2003. SIFT: Predicting amino acid changes that affect protein function. Nucleic acids research 31(13):3812-3814.

Ortega, M. S., A. C. Denicol, J. B. Cole, D. J. Null, and P. J. Hansen. 2016. Use of single nucleotide polymorphisms in candidate genes associated with daughter pregnancy rate for prediction of genetic merit for reproduction in Holstein cows. Animal Genetics 47(3):288-297. doi: 10.1111/age.12420

Purcell, S., B. Neale, K. Todd-Brown, L. Thomas, Manuel A R. Ferreira, D. Bender, J. Maller, P. Sklar, Paul I W. de Bakker, Mark J. Daly, and Pak C. Sham. 2007. PLINK: A Tool Set for Whole-Genome Association and Population-Based Linkage Analyses. American Journal of Human Genetics 81(3):559-575.

Ramayo-Caldas, Y., G. Renand, M. Ballester, R. Saintilan, and D. Rocha. 2016. Multi-breed and multi-trait co-association analysis of meat tenderness and other meat quality traits in three French beef cattle breeds. Genetics Selection Evolution 48(1):37. (journal article) doi: 10.1186/s12711-016-0216-y Richard, A. J., and J. M. Stephens. 2014. The role of JAK-STAT signaling in adipose tissue function. Biochimica et biophysica acta 1842(3):431-439. doi: 10.1016/j.bbadis.2013.05.030

Richardson, E., R. Herd, V. Oddy, J. Thompson, J. Archer, and P. Arthur. 2001. Body composition and implications for heat production of Angus steer progeny of parents selected for and against residual feed intake. Animal Production Science 41(7):1065-1072.

Richardson, E. C., and R. M. Herd. 2004. Biological basis for variation in residual feed intake in beef cattle. 2. Synthesis of results following divergent selection. Australian Journal of Experimental Agriculture 44(5):431-440. doi: https://doi.org/10.1071/EA02221

Richardson, I. W., D. P. Berry, H. L. Wiencko, I. M. Higgins, S. J. More, J. McClure, D. J. Lynn, and D. G. Bradley. 2016. A genome-wide association study for genetic susceptibility to *Mycobacterium bovis* infection in dairy cattle identifies a susceptibility QTL on chromosome 23. Genetics Selection Evolution 48(1):19. (journal article) doi: 10.1186/s12711-016-0197-x Rincker, C. B., N. A. Pyatt, L. L. Berger, and D. B. Faulkner. 2006. Relationship among GeneSTAR marbling marker, intramuscular fat deposition, and expected progeny differences in early weaned Simmental steers. Journal of Animal Science 84(3):686-693. doi: 10.2527/2006.843686x Saatchi, M., J. E. Beever, J. E. Decker, D. B. Faulkner, H. C. Freetly, S. L. Hansen, H. Yampara-Iquise, K. A. Johnson, S. D. Kachman, M. S. Kerley, J. Kim, D. D. Loy, E. Marques, H. L. Neibergs, E. J. Pollak, R. D. Schnabel, C. M. Seabury, D. W. Shike, W. M. Snelling, M. L. Spangler, R. L. Weaber, D. J. Garrick, and J. F. Taylor. 2014a. QTLs associated with dry matter intake, metabolic mid-test weight, growth and feed efficiency have little overlap across 4 beef cattle studies. BMC Genomics 15:1004.

Saatchi, M., R. D. Schnabel, J. F. Taylor, and D. J. Garrick. 2014b. Large-effect pleiotropic or closely linked QTL segregate within and across ten US cattle breeds. BMC Genomics 15doi: 10.1186/1471-2164-15-442

Schenkel, F. S., S. Miller, Z. Jiang, I. Mandell, X. Ye, H. Li, and J. Wilton. 2006. Association of a single nucleotide polymorphism in the calpastatin gene with carcass and meat quality traits of beef cattle. Journal of Animal Science 84(2):291-299.

Schenkel, F. S., S. P. Miller, and J. W. Wilton. 2004. Genetic parameters and breed differences for feed efficiency, growth, and body composition traits of young beef bulls. Canadian Journal of Animal Science 84(2):177-185. doi: 10.4141/A03-085

Serão, N. V. L., D. Gonzalez-Pella, J. E. Beever, D. B. Faulkner, B. R. Southey, and S. L. Rodriguez-Zas. 2013. Single nucleotide polymorphisms and haplotypes associated with feed efficiency in beef cattle. BMC Genetics 14(1):94. doi: 10.1186/1471-2156-14-94

Sherman, E., J. Nkrumah, B. Murdoch, and S. Moore. 2008a. Identification of polymorphisms influencing feed intake and efficiency in beef cattle. Animal genetics 39(3):225-231.

Sherman, E. L., J. D. Nkrumah, C. Li, R. Bartusiak, B. Murdoch, and S. S. Moore. 2009. Fine mapping quantitative trait loci for feed intake and feed efficiency in beef cattle1. Journal of Animal Science 87(1):37-45. doi: 10.2527/jas.2008-0876

Sherman, E. L., J. D. Nkrumah, B. M. Murdoch, C. Li, Z. Wang, A. Fu, and S. Moore. 2008b. Polymorphisms and haplotypes in the bovine neuropeptide Y, growth hormone receptor, ghrelin, insulin-like growth factor 2, and uncoupling proteins 2 and 3 genes and their associations with measures of growth, performance, feed efficiency, and carcass merit in beef cattle1. J. Anim. Sci 86:1-16.

Stothard, P., X. Liao, A. S. Arantes, M. De Pauw, C. Coros, G. S. Plastow, M. Sargolzaei, J. J. Crowley, J. A. Basarab, F. Schenkel, S. Moore, and S. P. Miller. 2015. A large and diverse collection of bovine genome sequences from the Canadian Cattle Genome Project. GigaScience 4(1):49. (journal article) doi: 10.1186/s13742-015-0090-5

Team, R. C. 2016. R: A language and environment for statistical computing. Vienna: R Foundation for Statistical Computing; 2014.

VanRaden, P., C. Van Tassell, G. Wiggans, T. Sonstegard, R. Schnabel, J. Taylor, and F. Schenkel. 2009. Invited review: Reliability of genomic predictions for North American Holstein bulls. Journal of dairy science 92(1): 16-24.

VanRaden, P. M. 2008. Efficient Methods to Compute Genomic Predictions. Journal of Dairy Science 91(11): 4414-4423. doi: 10.3168/jds.2007-0980

Wang, Y., X.-H. Wang, D.-X. Fan, Y. Zhang, M.-Q. Li, H.-X. Wu, and L.-P. Jin. 2014. PCSK6 regulated by LH inhibits the apoptosis of human granulosa cells via activin A and TGFβ2. Journal of Endocrinology 222(1):151-160. doi: 10.1530/joe-13-0592

Zeng, Z. B., T. Wang, and W. Zou. 2005. Modeling quantitative trait loci and interpretation of models. Genetics 169(3):1711-1725.

Zhang, L., Q. Gan, G. Hou, H. Gao, J. Li, and S. Xu. 2015. Investigation of TG gene variants and their effects on growth, carcass composition, and meat quality traits in Chinese steers. Genetics and Molecular Research 14(2): 5320-5326.

Zhang, Z., X. Ding, J. Liu, Q. Zhang, and D.-J. de Koning. 2011. Accuracy of genomic prediction using low-density marker panels. Journal of dairy science 94(7):3642-3650.

TABLE 1

The descriptive statistics for feed efficiency traits and its components of Herford, Angus and their crossbred beef cattle

| Trait | $N^1$ | Mean | SD | Minimum | Maximum |
|---|---|---|---|---|---|
| Average daily gain, kg/d$^2$ | 870 | 1.28 | 0.364 | 0.452 | 2.42 |
| Average daily dry matter intake, kg$^3$ | 831 | 8.577 | 1.259 | 4.97 | 12.43 |
| Midpoint metabolic weight, kg$^4$ | 822 | 87.77 | 9.037 | 64.72 | 114.81 |
| Residual feed intake, kg/d$^5$ | 855 | 0.038 | 0.450 | −1.3 | 1.35 |
| Residual feed intake adjusted for fatness, kg/d$^6$ | 852 | 0.013 | 0.437 | −1.25 | 1.26 |
| Back fat thickness, mm$^7$ | 865 | 6.833 | 2.590 | 1 | 14.81 |

$N^1$ = total number of animals used in the association analyses;
$ADG^2$ = average daily gain: recorded in kg per day from start to end of the finishing period;
$DMI^3$ = dry matter intake: recorded in kg per day from start to end of the finishing period;
$MMWT^4$ = midpoint metabolic weight: expressed in kg;
$RFI^5$ = residual feed intake: expressed in kg per day;
$RFI^6$ = residual feed intake adjusted for backfat: expressed in kg per day;
$BFat^7$ = backfat: recorded as fat depth at the end of the finishing period in millimeters.

TABLE 2

The P-values and effect estimate (SE) for the markers associated (P ≤ 0.05) with feed efficiency traits using allele substitution effect model

| Gene Name | rs#[1] | MAF[2] | ADG[3] P-value | ADG[3] Estimate ± SE | DMI[4] P-value | DMI[4] Estimate ± SE | MMWT[5] P-value | MMWT[5] Estimate ± SE | RFI[6] P-value | RFI[6] Estimate ± SE | RFI$_l$[7] P-value | RFI$_l$[7] Estimate ± SE | BFat[8] P-value | BFat[8] Estimate ± SE |
|---|---|---|---|---|---|---|---|---|---|---|---|---|---|---|
| SMARCAL1 | rs109065702 | 0.368 | | | | | | | 0.038 | -0.048 ± 0.023 | | | | |
| SMARCAL1 | rs109808135 | 0.367 | | | | | | | 0.043 | -0.047 ± 0.023 | | | | |
| SMARCAL1 | rs110348122 | 0.367 | | | | | | | 0.038 | -0.048 ± 0.023 | | | | |
| SMARCAL1 | rs109382589 | 0.312 | | | | | | | 0.036 | 0.048 ± 0.023 | | | | |
| SMARCAL1 | rs208660945 | 0.417 | 0.009 | -0.024 ± 0.009 | | | | | 0.05 | -0.042 ± 0.022 | | | | |
| LRRIQ3 | rs42417924 | 0.128 | | | 0.014 | -1.124 ± 0.45 | | | | | | | | |
| MGAM | rs110632853 | 0.076 | | | 0.032 | 0.17 ± 0.079 | | | | | | | | |
| DPP6 | rs110519795 | 0.388 | | | | | 0.030 | -0.651 ± 0.3 | | | | | 0.002 | -0.267 ± 0.09 |
| DPP6 | rs132717265 | 0.468 | | | | | | | | | | | | |
| CHADL | rs109499238 | 0.445 | | | | | 0.032 | -0.644 ± 0.3 | | | | | | |
| PPM1K | rs134225543 | 0.086 | 0.019 | 0.038 ± 0.016 | | | 0.006 | 1.402 ± 0.512 | | | | | 0.005 | -0.394 ± 0.14 |
| ABCG2 | rs110362902 | 0.102 | | | | | 0.016 | 1.224 ± 0.51 | | | | | | |
| PKD2 | rs29010894 | 0.207 | | | | | | | 0.030 | 0.051 ± 0.024 | 0.044 | 0.048 ± 0.023 | | |
| PKD2 | rs43702346 | 0.114 | | | | | 0.022 | 1.085 ± 0.47 | 0.041 | -0.045 ± 0.022 | 0.024 | 0.078 ± 0.034 | 0.025 | -0.29 ± 0.13 |
| EVC2 | rs207525537 | 0.174 | 0.041 | -0.026 ± 0.013 | | | | | | | | | | |
| CAST | rs137601357 | 0.376 | | | | | | | 0.048 | -0.047 ± 0.024 | 0.046 | -0.046 ± 0.023 | | |
| CAST | rs210072660 | 0.379 | | | | | | | 0.019 | -0.052 ± 0.022 | 0.022 | -0.05 ± 0.022 | | |
| CAST | rs384020496 | 0.096 | 0.021 | 0.032 ± 0.014 | | | 0.032 | 0.925 ± 0.43 | | | | | 0.009 | 0.317 ± 0.12 |
| CAST | rs133057384 | 0.107 | | | | | | | 0.044 | -0.072 ± 0.036 | 0.05 | -0.067 ± 0.035 | 0.005 | 0.366 ± 0.13 |
| CAST | rs110711318 | 0.087 | | | | | 0.031 | 1.087 ± 0.503 | | | | | 0.004 | 0.401 ± 0.14 |
| CNTFR | rs137400016 | 0.417 | 0.015 | 0.023 ± 0.01 | | | | | | | | | | |
| ANXA2 | rs471723345 | 0.084 | | | | | | | | | | | | |
| CNGA3 | rs43657898 | 0.405 | 0.039 | 0.02 ± 0.01 | | | | | 0.049 | 0.079 ± 0.04 | | | | |
| AFF3 | rs42275280 | 0.080 | 0.002 | -0.034 ± 0.011 | 0.023 | -0.111 ± 0.049 | 0.007 | -1.105 ± 0.41 | | | | | 0.025 | -0.248 ± 0.11 |
| ATP6V1E2 | rs43673198 | 0.278 | | | | | 0.016 | 0.746 ± 0.309 | | | | | 0.020 | 0.2 ± 0.086 |
| MAPK15 | rs110323635 | 0.476 | | | | | 0.037 | -0.902 ± 0.43 | | | | | | |
| FAM135B | rs381726438 | 0.373 | | | 0.021 | -0.141 ± 0.061 | 0.051 | -0.836 ± 0.43 | | | | | | |
| TG | rs109575847 | 0.169 | | | | | | | | | | | | |
| TG | rs133269500 | 0.133 | 0.006 | -0.038 ± 0.014 | | | | | | | | | | |
| TG | rs105472220 | 0.133 | 0.002 | -0.033 ± 0.011 | | | | | | | | | | |
| RB1CC1 | rs109800133 | 0.133 | | | | | | | 0.022 | 0.052 ± 0.022 | | | 0.019 | -0.303 ± 0.129 |
| CNTN5 | rs42544329 | 0.431 | | | | | | | | | | | 0.018 | -0.189 ± 0.08 |
| ELMOD1 | rs42235500 | 0.164 | | | | | | | | | | | 0.049 | 0.163 ± 0.083 |
| HMCN1 | rs211555481 | 0.476 | 0.033 | 0.024 ± 0.011 | | | | | | | | | | |
| HMCN1 | rs209012152 | 0.295 | 0.011 | 0.027 ± 0.01 | | | | | | | | | | |
| HMCN1 | rs41821600 | 0.348 | | | | | | | 0.021 | -0.117 ± 0.051 | 0.024 | -0.111 ± 0.049 | | |
| HMCN1 | rs210494625 | 0.049 | 0.026 | 0.025 ± 0.011 | | | | | | | | | | |
| HMCN1 | rs209439233 | 0.296 | 0.033 | 0.023 ± 0.011 | | | | | | | | | | |
| CACNA1G | rs476872493 | 0.305 | | | | | | | 0.0001 | -0.124 ± 0.032 | 0.0004 | -0.109 ± 0.031 | | |
| OCLN | rs134264563 | 0.154 | | | | | | | 0.05 | -0.066 ± 0.033 | 0.024 | -0.074 ± 0.033 | | |
| IPO11 | rs207541156 | 0.133 | | | | | | | | | 0.041 | 0.177 ± 0.087 | | |
| GHR | rs385640152 | 0.018 | | | | | | | 0.05 | -0.06 ± 0.031 | 0.021 | -0.07 ± 0.03 | | |
| OSMR | rs41947101 | 0.157 | | | | | | | | | 0.05 | 0.043 ± 0.022 | | |
| SLC45A2 | rs134604394 | 0.417 | 0.015 | 0.026 ± 0.011 | 0.016 | -0.13 ± 0.054 | 0.027 | -0.844 ± 0.38 | | | | | | |
| SLC45A2 | rs41946086 | 0.414 | 0.001 | -0.04 ± 0.012 | | | | | | | | | | |

TABLE 2-continued

The P-values and effect estimate (SE) for the markers associated (P ≤ 0.05) with feed efficiency traits using allele substitution effect model

| Gene Name | rs#[1] | MAF[2] | ADG[3] P-value | ADG[3] Estimate ± SE | DMI[4] P-value | DMI[4] Estimate ± SE | MMWT[5] P-value | MMWT[5] Estimate ± SE | RFI[6] P-value | RFI[6] Estimate ± SE | RFI$_f$[7] P-value | RFI$_f$[7] Estimate ± SE | BFat[8] P-value | BFat[8] Estimate ± SE |
|---|---|---|---|---|---|---|---|---|---|---|---|---|---|---|
| PCSK6 | rs43020736 | 0.451 | 0.016 | −0.109 ± 0.045 | 0.011 | −0.812 ± 0.32 | 0.048 | −0.046 ± 0.023 | 0.047 | −0.045 ± 0.023 | | |
| TMEM40 | rs133838809 | 0.216 | | | 0.022 | 0.862 ± 0.375 | | | | | | |
| TMEM40 | rs132658346 | 0.216 | | | 0.022 | 0.862 ± 0.375 | | | | | | |
| PAK1IP1 | rs42342962 | 0.340 | | | | | | | 0.034 | −0.048 ± 0.023 | | |
| MKI67 | rs110216983 | 0.381 | 0.021 | 0.104 ± 0.045 | 0.030 | 0.693 ± 0.319 | 0.014 | 0.059 ± 0.024 | 0.025 | 0.052 ± 0.023 | | |
| MKI67 | rs109930382 | 0.328 | 0.007 | 0.123 ± 0.045 | 0.024 | 0.727 ± 0.322 | 0.009 | 0.064 ± 0.025 | 0.016 | 0.058 ± 0.024 | | |
| MKI67 | rs109558734 | 0.332 | 0.006 | 0.124 ± 0.045 | 0.020 | 0.748 ± 0.32 | 0.007 | 0.066 ± 0.024 | 0.013 | 0.059 ± 0.024 | 0.039 | 0.184 ± 0.089 |
| C27H8orf40 | rs135814528 | 0.054 | | | 0.002 | 2.015 ± 0.654 | | | | | | |
| PHYHIPL | rs209765899 | 0.312 | | | | | 0.003 | −0.076 ± 0.025 | 0.003 | −0.074 ± 0.024 | | | rs#[1] = a reference SNP ID number assigned by National Center for Biotechnology Information (NCBI);
MAF[2] = Minor allele frequency;
ADG[3] = average daily gain: recorded in kg per day from start to end of the finishing period;
DMI[4] = dry matter intake: recorded in kg per day from start to end of the finishing period;
MMWT[5] = midpoint metabolic weight,
RFI[6] = residual feed intake expressed kg per day,
RFI$_f$[7] = residual feed intake adjusted for backfat,
BFat[8] = backfat: recorded as fat depth at the end of the finishing period in millimeters.

TABLE 3

The least squares means (SE) and P-values for the markers associated (P ≤ 0.05) with residual feed intake using genotypic effect and additive and dominance models

| Gene Name | rs#[1] | Genotype | P-value | Residual Feed Intake[2] LSM ± SE | a[3] ± SE | d[4] ± SE | P Value | Adjusted Back Fat Residual Feed Intake LSM ± SE | a ± SE | d ± SE |
|---|---|---|---|---|---|---|---|---|---|---|
| UMPS | rs110953962 | CC | 0.031 | 0.0164 ± 0.0281 | −0.0274 ± 0.028 | 0.0931 ± 0.035** | 0.035 | −0.0026 ± 0.028 | −0.0366 ± 0.028 | 0.0894 ± 0.034** |
|  |  | CT |  | 0.0821 ± 0.0262 |  |  |  | 0.0501 ± 0.026 |  |  |
|  |  | TT |  | −0.0384 ± 0.0514 |  |  |  | −0.0759 ± 0.050 |  |  |
| SMARCAL1 | rs109382589 | GG | 0.027 | 0.1569 ± 0.0477 | 0.0688 ± 0.026** | −0.0545 ± 0.035 | 0.018 | 0.1333 ± 0.046 | 0.0684 ± 0.025** | −0.0638 ± 0.034 |
|  |  | GT |  | 0.0337 ± 0.0277 |  |  |  | 0.0011 ± 0.027 |  |  |
|  |  | TT |  | 0.0194 ± 0.0258 |  |  |  | −0.0035 ± 0.025 |  |  |
| SMARCAL1 | rs208660945 | CC | 0.015 | 0.0274 ± 0.037 | −0.0369 ± 0.022 | −0.0648 ± 0.031* | 0.009 | 0.009 ± 0.036 | −0.0325 ± 0.022 | −0.0723 ± 0.030* |
|  |  | CT |  | −0.0005 ± 0.0264 |  |  |  | −0.0308 ± 0.026 |  |  |
|  |  | TT |  | 0.1011 ± 0.0294 |  |  |  | 0.074 ± 0.029 |  |  |
| CCSER1 | rs41574929 | GG | 0.003 | 0.0232 ± 0.021 | −0.0639 ± 0.057 | 0.1957 ± 0.067** | 0.005 | −0.0007 ± 0.021 | −0.0708 ± 0.055 | 0.1884 ± 0.065** |
|  |  | GT |  | 0.1551 ± 0.0411 |  |  |  | 0.1168 ± 0.040 |  |  |
|  |  | TT |  | −0.1046 ± 0.1129 |  |  |  | −0.1424 ± 0.11 |  |  |
| PKD2 | rs29010894 | CC |  | 0.0649 ± 0.0235 | −0.0154 ± 0.042 | −0.0528 ± 0.049 | 0.041 | 0.0422 ± 0.023 | −0.0099 ± 0.040 | −0.0717 ± 0.047 |
|  |  | TC |  | −0.0032 ± 0.03 |  |  |  | −0.0393 ± 0.029 |  |  |
|  |  | TT |  | 0.0342 ± 0.0813 |  |  |  | 0.0225 ± 0.079 |  |  |
| PKD2 | rs43702346 | GG | 0.025 | 0.0202 ± 0.022 | −0.0171 ± 0.061 | 0.1250 ± 0.069 | 0.015 | −0.0079 ± 0.022 | −0.0102 ± 0.059 | 0.1232 ± 0.067 |
|  |  | GT |  | 0.1281 ± 0.0379 |  |  |  | 0.1051 ± 0.037 |  |  |
|  |  | TT |  | −0.014 ± 0.1203 |  |  |  | −0.0283 ± 0.117 |  |  |
| CAST | rs210072660 | AA | 0.046 | 0.0888 ± 0.0277 | −0.0470 ± 0.023* | −0.0264 ± 0.032 | 0.042 | 0.0617 ± 0.027 | −0.0437 ± 0.023 | −0.0317 ± 0.031 |
|  |  | AG |  | 0.0153 ± 0.0266 |  |  |  | −0.0137 ± 0.026 |  |  |
|  |  | GG |  | −0.0053 ± 0.0404 |  |  |  | −0.0257 ± 0.039 |  |  |
| ANXA2 | rs471723345 | AA |  | 0.3293 ± 0.1361 | 0.1491 ± 0.068* | −0.1008 ± 0.080 | 0.048 | 0.3314 ± 0.132 | 0.1622 ± 0.066* | −0.1384 ± 0.077 |
|  |  | AG |  | 0.0794 ± 0.045 |  |  |  | 0.0308 ± 0.044 |  |  |
|  |  | GG |  | 0.0311 ± 0.021 |  |  |  | 0.0069 ± 0.021 |  |  |
| CNTN5 | rs42544329 | GG | 0.024 | −0.0197 ± 0.030 | 0.0464 ± 0.023* | 0.0459 ± 0.031 |  | −0.0333 ± 0.030 | 0.0372 ± 0.022 | 0.0343 ± 0.030 |
|  |  | GT |  | 0.0726 ± 0.026 |  |  |  | 0.0382 ± 0.026 |  |  |
|  |  | TT |  | 0.0732 ± 0.038 |  |  |  | 0.0411 ± 0.037 |  |  |
| CACNA1G | rs476872493 | AA | 0.0004 | −0.2255 ± 0.094 | −0.1499 ± 0.048** | 0.0407 ± 0.055 | 0.001 | −0.24 ± 0.0908 | −0.1413 ± 0.046** | 0.0505 ± 0.054 |
|  |  | GA |  | −0.0349 ± 0.034 |  |  |  | −0.0481 ± 0.034 |  |  |
|  |  | GG |  | 0.0742 ± 0.022 |  |  |  | 0.0426 ± 0.022 |  |  |
| IPO11 | rs207541156 | CA |  |  |  |  | 0.041 | 0.184 ± 0.086 |  |  |
|  |  | CC |  |  |  |  |  | 0.0068 ± 0.020 |  |  |
| GHR | rs385640152 | AA |  |  |  |  | 0.021 | 0.0425 ± 0.023 | −0.0148 ± 0.047 | −0.0825 ± 0.054 |
|  |  | TA |  |  |  |  |  | −0.0548 ± 0.032 |  |  |
|  |  | TT |  |  |  |  |  | 0.0129 ± 0.092 |  |  |
| PCSK6 | rs43020736 | CC | 0.039 | 0.0667 ± 0.033 | −0.0500 ± 0.023* | 0.0503 ± 0.031 |  | 0.0507 ± 0.032 | −0.0467 ± 0.023* | 0.0217 ± 0.030 |
|  |  | TC |  | 0.067 ± 0.0259 |  |  |  | 0.0257 ± 0.025 |  |  |
|  |  | TT |  | −0.0333 ± 0.036 |  |  |  | −0.0427 ± 0.035 |  |  |
| LMCD1 | rs208239648 | CC | 0.050 | 0.0382 ± 0.021 | −0.4254 ± 0.223 | 0.5324 ± 0.233* |  | 0.014 ± 0.021 | −0.4114 ± 0.217 | 0.4691 ± 0.226* |
|  |  | TC |  | 0.1452 ± 0.071 |  |  |  | 0.0717 ± 0.069 |  |  |
|  |  | TT |  | −0.8127 ± 0.446 |  |  |  | −0.8088 ± 0.433 |  |  |
| MKI67 | rs110216983 | AA | 0.011 | 0.0136 ± 0.028 | 0.0720 ± 0.025** | −0.0559 ± 0.033 | 0.038 | −0.0125 ± 0.028 | 0.0613 ± 0.024* | −0.0400 ± 0.032 |
|  |  | GA |  | 0.0297 ± 0.026 |  |  |  | 0.0088 ± 0.026 |  |  |
|  |  | GG |  | 0.1576 ± 0.044 |  |  |  | 0.11 ± 0.043 |  |  |

TABLE 3-continued

The least squares means (SE) and P-values for the markers associated (P ≤ 0.05) with residual feed intake using genotypic effect and additive and dominance models

| Gene Name | rs#[1] | Genotype | P-value | Residual Feed Intake[2] | | | P Value | Adjusted Back Fat Residual Feed Intake | | |
|---|---|---|---|---|---|---|---|---|---|---|
| | | | | LSM ± SE | a[3] ± SE | d[4] ± SE | | LSM ± SE | a ± SE | d ± SE |
| MKI67 | rs109930382 | CC | 0.025 | 0.0073 ± 0.026 | 0.0738 ± 0.028** | -0.0276 ± 0.035 | 0.043 | -0.0158 ± 0.026 | 0.0664 ± 0.027* | -0.0245 ± 0.034 |
| | | CT | | 0.0535 ± 0.027 | | | | 0.0261 ± 0.026 | | |
| | | TT | | 0.1549 ± 0.05 | | | | 0.117 ± 0.05 | | |
| MKI67 | rs109558734 | CC | 0.019 | 0.0055 ± 0.026 | 0.0760 ± 0.027** | -0.0291 ± 0.035 | 0.036 | -0.0172 ± 0.026 | 0.0676 ± 0.026* | -0.0257 ± 0.034 |
| | | GC | | 0.0524 ± 0.026 | | | | 0.0247 ± 0.026 | | |
| | | GG | | 0.1575 ± 0.050 | | | | 0.118 ± 0.049 | | |
| PHYHIPL | rs209765899 | AA | 0.010 | -0.0749 ± 0.051 | -0.0812 ± 0.028** | 0.0149 ± 0.036 | 0.011 | -0.0941 ± 0.049 | -0.0773 ± 0.027** | 0.0101 ± 0.034 |
| | | TA | | 0.0211 ± 0.027 | | | | -0.0067 ± 0.027 | | |
| | | TT | | 0.0874 ± 0.026 | | | | 0.0606 ± 0.026 | | | rs#[1] = a reference SNP ID number assigned by National Center for Biotechnology Information (NCBI);
Residual Feed Intake[2] = residual feed intake expressed in kg per day;
a[3] = Additive effect of SNP expressed in kg per day;
d[4] = Dominance effect of SNP expressed in kg per day;
*is significant at P < 0.05;
**is significant at P < 0.01

TABLE 4

The least squares means (SE) and P-values for the markers associated (P ≤ 0.05) with average daily gain and dry matter intake using genotypic effect and additive and dominance models

| | | | Average Daily Gain (kg) | | | | Dry Matter Intake (kg) | | | |
|---|---|---|---|---|---|---|---|---|---|---|
| Gene Name | rs#[1] | Genotype | P-value | LSM ± SE | $a^2$ ± SE | $d^3$ ± SE | P-value | LSM ± SE | a ± SE | d ± SE |
| ACAD11 | rs210293774 | CC | 0.004 | 1.405 ± 0.024 | 0.028 ± | −0.047 ± | 0.008 | 8.754 ± 0.048 | 0.114 ± | −0.196 ± |
| | | GC | | 1.331 ± 0.016 | 0.012* | 0.015** | | 8.444 ± 0.048 | 0.053* | 0.067** |
| | | GG | | 1.35 ± 0.015 | | | | 8.526 ± 0.048 | | |
| ACAD11 | rs208270150 | CC | 0.006 | 1.349 ± 0.015 | 0.028 ± | −0.044 ± | 0.013 | 8.526 ± 0.048 | 0.108 ± | −0.187 ± |
| | | CT | | 1.333 ± 0.016 | 0.012* | 0.015** | | 8.447 ± 0.048 | 0.054* | 0.067** |
| | | TT | | 1.405 ± 0.024 | | | | 8.742 ± 0.048 | | |
| SMARCAL1 | rs109065702 | CC | 0.05 | 1.354 ± 0.016 | 0.013 ± | −0.032 ± | | 8.529 ± 0.048 | 0.039 ± | −0.095 ± |
| | | CT | | 1.335 ± 0.015 | 0.01 | 0.013* | | 8.472 ± 0.048 | 0.047 | 0.058 |
| | | TT | | 1.38 ± 0.022 | | | | 8.606 ± 0.048 | | |
| SMARCAL1 | rs109808135 | CC | 0.049 | 1.38 ± 0.022 | 0.012 ± | −0.032 ± | | 8.6 ± 0.048 | 0.035 ± | −0.092 ± |
| | | TC | | 1.336 ± 0.015 | 0.011 | 0.013* | | 8.473 ± 0.048 | 0.047 | 0.058 |
| | | TT | | 1.356 ± 0.016 | | | | 8.531 ± 0.048 | | |
| SMARCAL1 | rs109382589 | GG | | 1.382 ± 0.022 | 0.017 ± | −0.029 ± | 0.029 | 8.678 ± 0.048 | 0.082 ± | −0.161 ± |
| | | GT | | 1.336 ± 0.016 | 0.011 | 0.014* | | 8.436 ± 0.048 | 0.049 | 0.062* |
| | | TT | | 1.348 ± 0.016 | | | | 8.515 ± 0.048 | | |
| SMARCAL1 | rs208660945 | CC | 0.024 | 1.311 ± 0.019 | −0.026 ± | 0.011 ± | | 8.434 ± 0.048 | −0.067 ± | −0.015 ± |
| | | CT | | 1.348 ± 0.016 | 0.009** | 0.013 | | 8.486 ± 0.048 | 0.042 | 0.056 |
| | | TT | | 1.362 ± 0.016 | | | | 8.567 ± 0.048 | | |
| LRRIQ3 | rs42417924 | CC | | 1.35 ± 0.014 | −0.055 ± | 0.056 ± | | 8.528 ± 0.048 | −0.067 ± | −0.028 ± |
| | | GC | | 1.352 ± 0.019 | 0.024* | 0.027* | | 8.433 ± 0.048 | 0.106 | 0.116 |
| | | GG | | 1.241 ± 0.049 | | | | 8.394 ± 0.048 | | |
| PPM1K | rs134225543 | CC | 0.028 | 1.338 ± 0.014 | 0.015 ± | 0.038 ± | | 8.481 ± 0.048 | 0.019 ± | 0.147 ± |
| | | TC | | 1.391 ± 0.022 | 0.024 | 0.029 | | 8.648 ± 0.048 | 0.104 | 0.128 |
| | | TT | | 1.368 ± 0.049 | | | | 8.52 ± 0.048 | | |
| CAST | rs137601357 | CC | 0.039 | 1.377 ± 0.021 | 0.006 ± | −0.034 ± | | 8.505 ± 0.05 | −0.045 ± | −0.079 ± |
| | | TC | | 1.337 ± 0.016 | 0.01 | 0.013* | | 8.471 ± 0.05 | 0.046 | 0.058 |
| | | TT | | 1.366 ± 0.017 | | | | 8.594 ± 0.05 | | |
| CAST | rs384020496 | AA | 0.013 | 1.444 ± 0.035 | 0.051 ± | −0.045 ± | | 8.769 ± 0.048 | 0.14 ± | −0.114 ± |
| | | GA | | 1.348 ± 0.022 | 0.017** | 0.025 | | 8.514 ± 0.048 | 0.075 | 0.109 |
| | | GG | | 1.343 ± 0.014 | | | | 8.488 ± 0.048 | | |
| CNTFR | rs137400016 | CC | 0.022 | 1.321 ± 0.017 | 0.021 ± | 0.016 ± | | 8.418 ± 0.048 | 0.055 ± | 0.09 ± |
| | | CT | | 1.358 ± 0.015 | 0.01 | 0.013 | | 8.562 ± 0.048 | 0.044 | 0.055 |
| | | TT | | 1.363 ± 0.019 | | | | 8.527 ± 0.048 | | |
| ATP6V1E2 | rs43673198 | CC | 0.008 | 1.365 ± 0.015 | −0.033 ± | −0.002 ± | | 8.567 ± 0.048 | −0.091 ± | 0.04 ± |
| | | CT | | 1.33 ± 0.016 | 0.013 | 0.016 | | 8.436 ± 0.048 | 0.059 | 0.07 |
| | | TT | | 1.299 ± 0.027 | | | | 8.385 ± 0.048 | | |
| ERCC5 | rs133716845 | CC | | 1.343 ± 0.016 | −0.011 ± | 0.024 ± | 0.036 | 8.488 ± 0.048 | −0.083 ± | 0.149 ± |
| | | TC | | 1.356 ± 0.015 | 0.011 | 0.014 | | 8.554 ± 0.048 | 0.048 | 0.061* |
| | | TT | | 1.321 ± 0.023 | | | | 8.322 ± 0.048 | | |
| TG | rs133269500 | AA | 0.011 | 1.231 ± 0.051 | −0.062 ± | 0.032 ± | | 8.037 ± 0.048 | −0.244 ± | 0.18 ± |
| | | GA | | 1.324 ± 0.018 | 0.025 | 0.027 | | 8.461 ± 0.048 | 0.106* | 0.116 |
| | | GG | | 1.354 ± 0.014 | | | | 8.525 ± 0.048 | | |
| TG | rs110547220 | CC | 0.005 | 1.289 ± 0.024 | −0.039 ± | 0.017 ± | | 8.328 ± 0.047 | −0.118 ± | 0.081 ± |
| | | GC | | 1.345 ± 0.016 | 0.012** | 0.015 | | 8.527 ± 0.047 | 0.054* | 0.064 |
| | | GG | | 1.367 ± 0.015 | | | | 8.565 ± 0.047 | | |
| HMCN1 | rs209012152 | AA | 0.037 | 1.385 ± 0.023 | 0.028 ± | −0.004 ± | | 8.587 ± 0.048 | 0.046 ± | −0.048 ± |
| | | GA | | 1.353 ± 0.015 | 0.011* | 0.014 | | 8.493 ± 0.048 | 0.051 | 0.061 |
| | | GG | | 1.329 ± 0.016 | | | | 8.496 ± 0.048 | | |
| SLC45A2 | rs134604394 | AA | 0.05 | 1.38 ± 0.021 | 0.027 ± | −0.005 ± | | 8.606 ± 0.048 | 0.085 ± | −0.008 ± |
| | | AT | | 1.348 ± 0.015 | 0.011* | 0.013 | | 8.513 ± 0.048 | 0.049 | 0.057 |
| | | TT | | 1.325 ± 0.018 | | | | 8.436 ± 0.048 | | |
| SLC45A2 | rs41946086 | AA | 0.003 | 1.388 ± 0.019 | −0.04 ± | −0.009 ± | 0.042 | 8.642 ± 0.048 | −0.128 ± | −0.043 ± |
| | | AG | | 1.339 ± 0.015 | 0.012** | 0.013 | | 8.472 ± 0.048 | 0.054* | 0.058 |
| | | GG | | 1.309 ± 0.02 | | | | 8.387 ± 0.048 | | |
| LMCD1 | rs208239648 | CC | 0.053 | 1.347 ± 0.014 | −0.216 ± | 0.228 ± | 0.042 | 8.517 ± 0.048 | −0.987 ± | 0.916 ± |
| | | TC | | 1.359 ± 0.032 | 0.091* | 0.095* | | 8.445 ± 0.048 | 0.395* | 0.408* |
| | | TT | | 0.916 ± 0.183 | | | | 6.543 ± 0.048 | | |
| MKI67 | rs110216983 | AA | | 1.337 ± 0.016 | 0.013 ± | −0.001 ± | 0.039 | 8.441 ± 0.048 | 0.119 ± | −0.063 ± |
| | | GA | | 1.349 ± 0.016 | 0.011 | 0.013 | | 8.496 ± 0.048 | 0.047* | 0.058 |
| | | GG | | 1.362 ± 0.021 | | | | 8.678 ± 0.048 | | |
| MKI67 | rs109930382 | CC | | 1.335 ± 0.016 | 0.013 ± | 0.01 ± | 0.025 | 8.433 ± 0.048 | 0.131 ± | −0.023 ± |
| | | CT | | 1.357 ± 0.016 | 0.011 | 0.014 | | 8.54 ± 0.048 | 0.05** | 0.062 |
| | | TT | | 1.36 ± 0.024 | | | | 8.694 ± 0.048 | | |
| MKI67 | rs109558734 | CC | | 1.334 ± 0.016 | 0.014 ± | 0.009 ± | 0.02 | 8.431 ± 0.048 | 0.134 ± | −0.029 ± |
| | | GC | | 1.357 ± 0.016 | 0.011 | 0.014 | | 8.536 ± 0.048 | 0.05** | 0.061 |
| | | GG | | 1.362 ± 0.023 | | | | 8.7 ± 0.048 | | | rs#[1] = a reference SNP ID number assigned by National Center for Biotechnology Information (NCBI);
$a^2$ = Additive effect of SNP;
$d^3$ = Dominance effect of SNP;
*is significant at P < 0.05;
**is significant at P < 0.01

TABLE 5

The least squares means (SE) and P-values for the markers associated ($P \leq 0.05$) with midpoint metabolic weight and back fat using genotypic effect and additive and dominance models

| Gene Name | rs#[1] | Geno-type | Midpoint Metabolic Weight (kg) | | | | Back fat (mm) | | | |
|---|---|---|---|---|---|---|---|---|---|---|
| | | | P-value | LSM ± SE | $a^2$ ± SE | $d^3$ ± SE | P-value | LSM ± SE | $a^1$ ± SE | $d^2$ ± SE |
| RRP1B | rs43285609 | AA | | 85.739 ± 0.381 | −0.135 ± | 0.312 ± | 0.05 | 7.022 ± 0.183 | 0.019 ± | 0.254 ± |
| RRP1B | rs43285609 | GA | | 86.185 ± 0.381 | 0.321 | 0.388 | | 7.257 ± 0.137 | 0.089 | 0.109* |
| RRP1B | rs43285609 | GG | | 86.008 ± 0.381 | | | | 6.984 ± 0.151 | | |
| GALNT13 | rs438856835 | AA | | 85.883 ± 0.38 | 0.196 ± | 0.828 ± | 0.035 | 7.094 ± 0.13 | −0.486 ± | 0.77 ± |
| GALNT13 | rs438856835 | CA | | 86.908 ± 0.38 | 0.962 | 1.063 | | 7.378 ± 0.191 | 0.274 | 0.304* |
| GALNT13 | rs438856835 | CC | | 86.275 ± 0.38 | | | | 6.122 ± 0.555 | | |
| SMARCAL1 | rs208660945 | CC | | 85.764 ± 0.382 | −0.172 ± | 0.219 ± | 0.049 | 7.177 ± 0.174 | 0.111 ± | 0.203 ± |
| SMARCAL1 | rs208660945 | CT | | 86.155 ± 0.382 | 0.297 | 0.391 | | 7.269 ± 0.141 | 0.083 | 0.109 |
| SMARCAL1 | rs208660945 | TT | | 86.109 ± 0.382 | | | | 6.955 ± 0.148 | | |
| LRRIQ3 | rs42417924 | CC | 0.043 | 86.331 ± 0.38 | −0.857 ± | −0.368 ± | | 7.171 ± 0.132 | −0.013 ± | −0.187 ± |
| LRRIQ3 | rs42417924 | GC | | 85.107 ± 0.38 | 0.742 | 0.806 | | 6.971 ± 0.17 | 0.211 | 0.231 |
| LRRIQ3 | rs42417924 | GG | | 84.618 ± 0.38 | | | | 7.145 ± 0.427 | | |
| DPP6 | rs110519795 | AA | 0.05 | 86.44 ± 0.381 | −0.725 ± | 0.446 ± | | 7.178 ± 0.148 | −0.062 ± | 0.017 ± |
| DPP6 | rs110519795 | AG | | 86.161 ± 0.381 | 0.308* | 0.395 | | 7.133 ± 0.142 | 0.086 | 0.112 |
| DPP6 | rs110519795 | GG | | 84.99 ± 0.381 | | | | 7.054 ± 0.18 | | |
| DPP6 | rs132717265 | AA | | 85.689 ± 0.382 | −0.393 ± | −0.015 ± | 0.007 | 6.895 ± 0.164 | −0.264 ± | −0.067 ± |
| DPP6 | rs132717265 | GA | | 86.068 ± 0.382 | 0.313 | 0.381 | | 7.092 ± 0.138 | 0.086** | 0.107 |
| DPP6 | rs132717265 | GG | | 86.476 ± 0.382 | | | | 7.423 ± 0.159 | | |
| PPM1K | rs134225543 | CC | 0.018 | 85.78 ± 0.383 | 1.013 ± | 0.673 ± | 0.015 | 7.198 ± 0.129 | −0.521 ± | 0.214 ± |
| PPM1K | rs134225543 | TC | | 87.465 ± 0.383 | 0.727 | 0.886 | | 6.891 ± 0.194 | 0.207* | 0.253 |
| PPM1K | rs134225543 | TT | | 87.806 ± 0.383 | | | | 6.156 ± 0.424 | | |
| CAST | rs384020496 | AA | | 87.727 ± 0.377 | 0.973 ± | −0.124 ± | 0.014 | 7.465 ± 0.31 | 0.203 ± | 0.277 ± |
| CAST | rs384020496 | GA | | 86.631 ± 0.377 | 0.518 | 0.751 | | 7.539 ± 0.199 | 0.15 | 0.214 |
| CAST | rs384020496 | GG | | 85.782 ± 0.377 | | | | 7.058 ± 0.13 | | |
| CAST | rs133057384 | AA | | 87.548 ± 0.38 | 0.827 ± | −0.102 ± | 0.018 | 7.665 ± 0.42 | 0.307 ± | 0.088 ± |
| CAST | rs133057384 | GA | | 86.619 ± 0.38 | 0.731 | 0.846 | | 7.447 ± 0.179 | 0.207 | 0.24 |
| CAST | rs133057384 | GG | | 85.894 ± 0.38 | | | | 7.052 ± 0.13 | | |
| CAST | rs110711318 | CC | | 85.843 ± 0.38 | 1.273 ± | −0.272 ± | 0.017 | 7.058 ± 0.131 | 0.37 ± | 0.045 ± |
| CAST | rs110711318 | TC | | 86.843 ± 0.38 | 0.831 | 0.968 | | 7.473 ± 0.188 | 0.233 | 0.272 |
| CAST | rs110711318 | TT | | 88.388 ± 0.38 | | | | 7.797 ± 0.472 | | |
| AFF3 | rs42275280 | CC | 0.011 | 84.288 ± 0.382 | −0.992 ± | −2.594 ± | | 6.691 ± 0.242 | −0.238 ± | −0.271 ± |
| AFF3 | rs42275280 | CT | | 82.687 ± 0.382 | 0.417* | 1.999 | | 6.658 ± 0.576 | 0.112* | 0.577 |
| AFF3 | rs42275280 | TT | | 86.272 ± 0.382 | | | | 7.167 ± 0.13 | | |
| ERCC5 | rs133716845 | CC | 0.031 | 85.967 ± 0.38 | −0.598 ± | 1.054 ± | | 7.098 ± 0.144 | 0.019 ± | 0.066 ± |
| ERCC5 | rs133716845 | TC | | 86.423 ± 0.38 | 0.34 | 0.419* | | 7.182 ± 0.141 | 0.096 | 0.119 |
| ERCC5 | rs133716845 | TT | | 84.771 ± 0.38 | | | | 7.135 ± 0.205 | | |
| MAPK15 | rs110323635 | AA | 0.047 | 85.592 ± 0.382 | 0.811 ± | −0.228 ± | | 6.957 ± 0.148 | 0.185 ± | 0.055 ± |
| MAPK15 | rs110323635 | GA | | 86.175 ± 0.382 | 0.33* | 0.403 | | 7.196 ± 0.138 | 0.091* | 0.114 |
| MAPK15 | rs110323635 | GG | | 87.213 ± 0.382 | | | | 7.326 ± 0.192 | | |
| TG | rs133269500 | AA | 0.02 | 82.153 ± 0.379 | −2.021 ± | 1.59 ± | | 6.736 ± 0.437 | −0.214 ± | 0.073 ± |
| TG | rs133269500 | GA | | 85.765 ± 0.379 | 0.731** | 0.798* | | 7.024 ± 0.165 | 0.212 | 0.232 |
| TG | rs133269500 | GG | | 86.195 ± 0.379 | | | | 7.165 ± 0.131 | | |
| ELMOD1 | rs42235500 | AA | | 85.947 ± 0.382 | −0.039 ± | 0.502 ± | 0.043 | 6.751 ± 0.192 | −0.2 ± | 0.25 ± |
| ELMOD1 | rs42235500 | GA | | 86.488 ± 0.382 | 0.287 | 1.095 | | 7.202 ± 0.314 | 0.081* | 0.301 |
| ELMOD1 | rs42235500 | GG | | 86.025 ± 0.382 | | | | 7.151 ± 0.129 | | |
| UGT3A1 | rs42345570 | AA | | 85.329 ± 0.381 | −0.278 ± | 0.747 ± | 0.027 | 7.009 ± 0.255 | 0.001 ± | 0.292 ± |
| UGT3A1 | rs42345570 | CA | | 86.354 ± 0.381 | 0.455 | 0.512 | | 7.3 ± 0.142 | 0.124 | 0.143* |
| UGT3A1 | rs42345570 | CC | | 85.884 ± 0.38 | | | | 7.006 ± 0.14 | | |
| SLC45A2 | rs134604394 | AA | | 86.476 ± 0.382 | 0.406 ± | 0.081 ± | | 7.012 ± 0.185 | −0.05 ± | 0.128 ± |
| SLC45A2 | rs134604394 | AT | | 86.151 ± 0.382 | 0.348 | 0.397 | | 7.191 ± 0.137 | 0.097 | 0.112 |
| SLC45A2 | rs134604394 | TT | | 85.664 ± 0.382 | | | | 7.113 ± 0.161 | | |
| PCSK6 | rs43020736 | CC | 0.027 | 86.725 ± 0.38 | −0.824 ± | 0.336 ± | | 7.09 ± 0.16 | −0.041 ± | 0.183 ± |
| PCSK6 | rs43020736 | TC | | 86.237 ± 0.38 | 0.319* | 0.383 | | 7.232 ± 0.142 | 0.09 | 0.109 |
| PCSK6 | rs43020736 | TT | | 85.078 ± 0.38 | | | | 7.009 ± 0.169 | | |
| C27H8orf40 | rs135814528 | AA | 0.009 | 85.856 ± 0.379 | 1.856 ± | 0.175 ± | 0.036 | 7.117 ± 0.128 | −1.284 ± | 1.505 ± |
| C27H8orf40 | rs135814528 | GA | | 87.887 ± 0.379 | 2.012 | 2.098 | | 7.338 ± 0.215 | 0.564* | 0.589* |
| C27H8orf40 | rs135814528 | GG | | 89.569 ± 0.379 | | | | 4.549 ± 1.132 | | | rs#[1] = a reference SNP ID number assigned by National Center for Biotechnology Information (NCBI);
$a^2$ = Additive effect of SNP;
$d^3$ = Dominance effect of SNP;
*is significant at $P < 0.05$;
**is significant at $P < 0.01$

TABLE 6

The enriched (at P < 0.05) gene ontology terms and biological pathways having genes associated with feed efficiency and its components traits

| Category[1] | Term | P-Value[2] | Genes Name |
|---|---|---|---|
| BP | GO:0001889~liver development | 0.010[&] | MKI67, PKD2, RB1CC1 |
| BP | GO:0034220~ion transmembrane transport | 0.011[&] | DPP6, CNGA3, PKD2, ATP6V1E2, ANXA2, CACNA1G |
| BP | GO:0061008~hepaticobiliary system development | 0.011[&] | MKI67, PKD2, RB1CC1 |
| BP | GO:0055085~transmembrane transport | 0.012[&] | DPP6, CNGA3, PKD2, ATP6V1E2, ANXA2, CACNA1G, ABCG2 |
| BP | GO:0006812~cation transport | 0.018 | DPP6, CNGA3, PKD2, ATP6V1E2, ANXA2, CACNA1G |
| BP | GO:0098655~cation transmembrane transport | 0.018 | DPP6, CNGA3, PKD2, ATP6V1E2, ANXA2 |
| BP | GO:0006811~ion transport | 0.024 | DPP6, CNGA3, PKD2, ATP6V1E2, ANXA2, TG, CACNA1G |
| BP | GO:0070509~calcium ion import | 0.031 | PKD2, ANXA2, CACNA1G |
| BP | GO:0030001~metal ion transport | 0.034 | DPP6, CNGA3, PKD2, ANXA2, CACNA1G |
| BP | GO:0015672~monovalent inorganic cation transport | 0.036 | DPP6, CNGA3, PKD2, ATP6V1E2 |
| BP | GO:0006813~potassium ion transport | 0.040 | DPP6, CNGA3, PKD2 |
| BP | GO:0048732~gland development | 0.040 | MKI67, PKD2, TG, RB1CC1 |
| MF | GO:0008324~cation transmembrane transporter activity | 0.009[&] | SLC45A2, CNGA3, PKD2, ATP6V1E2, ANXA2, CACNA1G |
| MF | GO:0004896~cytokine receptor activity | 0.017[&] | CNTFR, OSMR, GHR |
| MF | GO:0005262~calcium channel activity | 0.023 | PKD2, ANXA2, CACNA1G |
| MF | GO:0022890~inorganic cation transmembrane transporter activity | 0.023 | CNGA3, PKD2, ATP6V1E2, ANXA2, CACNA1G |
| MF | GO:0005261~cation channel activity | 0.028 | CNGA3, PKD2, ANXA2, CACNA1G |
| MF | GO:0015085~calcium ion transmembrane transporter activity | 0.029 | PKD2, ANXA2, CACNA1G |
| MF | GO:0022843~voltage-gated cation channel activity | 0.038 | CNGA3, PKD2, CACNA1G |
| MF | GO:0072509~divalent inorganic cation transmembrane transporter activity | 0.049 | PKD2, ANXA2, CACNA1G |
| KEGG | bta04630:Jak-STAT signaling pathway | 0.027 | CNTFR, OSMR, GHR |

Category[1] = gene ontology (GO) and pathway categories where BP is biological process, MF is molecular function and KEGG is the Kyoto Encyclopedia of Genes and Genomes pathway.
P-Value[2] is the absolute P-Value;
[&]P-value is significant at less than 20% false discovery rate (FDR)

TABLE 7

Heritability values estimated using the different SNP sets

| Trait | $h^2_p \pm SE^1$ | $h^2_{50k} \pm SE^2$ | $h^2_{full} \pm SE^3$ | $h^2_{sig10} \pm SE^4$ | $h^2_{sig5} \pm SE^5$ |
|---|---|---|---|---|---|
| ADG, kg/d[6] | 0.276 ± 0.083 | 0.254 ± 0.080 | 0.078 ± 0.030 | 0.089 ± 0.030 | 0.072 ± 0.027 |
| DMI, kg[7] | 0.499 ± 0.095 | 0.513 ± 0.077 | 0.079 ± 0.031 | 0.089 ± 0.032 | 0.077 ± 0.029 |
| MMWT, kg[8] | 0.690 ± 0.090 | 0.572 ± 0.072 | 0.126 ± 0.037 | 0.111 ± 0.036 | 0.076 ± 0.03 |
| RFI, kg/d[9] | 0.247 ± 0.078 | 0.213 ± 0.066 | 0.038 ± 0.020 | 0.048 ± 0.021 | 0.047 ± 0.021 |
| RFIf, kg/d[10] | 0.273 ± 0.080 | 0.240 ± 0.069 | 0.044 ± 0.021 | 0.053 ± 0.022 | 0.053 ± 0.022 |
| BFat, mm[11] | 0.446 ± 0.093 | 0.369 ± 0.073 | 0.037 ± 0.024 | 0.064 ± 0.027 | 0.067 ± 0.028 |

$h^2_p{}^1$ = Heritability estimate from using the pedigree information;
$h^2_{50k}{}^2$ = Heritability estimate from using the 50 k panel (n= 40465 SNP);
$h^2_{full}{}^3$ = Heritability estimate using the full SNPs set (n =159 SNP);
$h^2_{sig10}{}^4$ = Heritability estimate from using the significant (P < 0.10) SNPs set (n = 92 SNP);
$h^2_{sig5}{}^5$ = Heritability estimate from using the significant (P < 0.05) SNPs set (n = 63 SNP);
ADG[6] = average daily gain: recorded in kg per day from start to end of the finishing period;
DMI[7] = dry matter intake: recorded in kg per day from start to end of the finishing period;
MMWT[8] = midpoint metabolic weight,
RFI[9] = residual feed intake expressed kg per day,
RFIf[10] = residual feed intake adjusted for backfat,
BFat[11] = backfat: recorded as fat depth at the end of the finishing period in millimeters.

TABLE 8

| NCBI_dbSNP_rs_ID | Chromosome Name | Base Pair Position | Gene Name | Ensembl Gene ID | Alleles | EntrezGene ID | Author for reference population | Variant Type | SIFT value | SIFT prediction |
|---|---|---|---|---|---|---|---|---|---|---|
| rs43242284 | 1 | 67635588 | PARP14 | ENSBTAG00000016656 | G/A | 540789 | Karisa_et_al_2014 | Missense | 0.04 | deleterious |
| rs110953962 | 1 | 69753035 | UMPS | ENSBTAG00000013727 | C/T | 281568 | Karisa_et_al_2014 | Missense | 0.01 | deleterious |
| rs110746934 | 1 | 136620597 | RAB6B | ENSBTAG00000000905 | G/A | 526526 | Serão et al. BMC Genetics 2013, 14:94 | Splice Region | — | |
| rs384044855 | 1 | 137993085 | UBA5 | ENSBTAG00000004495 | T/A | 509292 | Karisa_et_al_2014 | missense_variant | 0.18 | tolerated |
| rs210293774 | 1 | 138014396 | ACAD11 | ENSBTAG00000031010 | G/C | 526956 | Karisa_et_al_2014 | Missense | 0.01 | deleterious |
| rs208270150 | 1 | 138045480 | ACAD11 | ENSBTAG00000031010 | C/T | 526956 | Karisa_et_al_2014 | Missense | 0.24 | tolerated |
| rs137771776 | 1 | 138084824 | ACAD11 | ENSBTAG00000031010 | G/A | 526956 | Karisa_et_al_2014 | Missense | 0 | deleterious |
| rs41629678 | 1 | 138644549 | KCNH8 | ENSBTAG00000012798 | T/C | 618639 | Abo-Ismail_et_al_2014 | synonymous_variant | | |
| rs43277176 | 1 | 142934135 | BACE2 | ENSBTAG00000000394 | C/T | 534774 | Abo-Ismail_et_al_2014 | synonymous_variant | | |
| rs43285609 | 1 | 146449085 | RRP1B | ENSBTAG00000017418 | G/A | 510240 | Yao_et_al_2013 | | 0.01 | deleterious |
| rs445312693 | 1 | 146457394 | RRP1B | ENSBTAG00000017418 | A/G | 510240 | Yao_et_al_2013 | | 0.13 | tolerated |
| rs17870910 | 2 | 6611059 | ASNSD1 | ENSBTAG00000000492 | C/T | 539672 | Karisa_et_al_2014 | missense variant | 0.59 | tolerated |
| rs450068075 | 2 | 30183902 | SCN9A | ENSBTAG00000002425 | C/T | 533065 | Rolf_et_al_2011 | | 0 | deleterious |
| rs438856835 | 2 | 41791856 | GALNT13 | ENSBTAG00000005562 | A/C | 532545 | Abo-Ismail_et_al_2014 | | | deleterious |
| rs43307594 | 2 | 42036571 | GALNT13 | ENSBTAG00000005562 | C/T | 532545 | Abo-Ismail_et_al_2014 | synonymous_variant | | |
| rs1089991273 | 2 | 68111186 | DPP10 | ENSBTAG00000005235 | A/G | 617222 | Abo-Ismail_et_al_2014 | downstream_gene_variant | | |
| rs136066715 | 2 | 89549796 | AOX1 | ENSBTAG00000009725 | G/A | 338074 | Karisa_et_al_2014 | Missense | 0.33 | tolerated |
| rs134515132 | 2 | 89549850 | AOX1 | ENSBTAG00000009725 | G/A | 338074 | Karisa_et_al_2014 | Missense | 0.6 | tolerated |
| rs133016801 | 2 | 89550348 | AOX1 | ENSBTAG00000009725 | A/G | 338074 | Karisa_et_al_2014 | Missense | 1 | tolerated |
| rs134892794 | 2 | 89550355 | AOX1 | ENSBTAG00000009725 | C/A | 338074 | Karisa_et_al_2014 | Missense | 1 | tolerated |
| rs137383727 | 2 | 89550367 | AOX1 | ENSBTAG00000009725 | A/G | 338074 | Karisa_et_al_2014 | Missense | 0.7 | tolerated |
| rs109437938 | 2 | 89562194 | AOX1 | ENSBTAG00000009725 | G/A | 338074 | Karisa_et_al_2014 | Missense | 0.25 | tolerated |
| rs109065702 | 2 | 105138600 | SMARCAL1 | ENSBTAG00000003843 | T/C | 338072 | Karisa_et_al_2014 | Missense | 0.42 | tolerated |

TABLE 8-continued

| NCBI_dbSNP_rs_ID | Chromosome Name | Base Pair Position | Gene Name | Ensembl Gene ID | Alleles | EntrezGene ID | Author for reference population | Variant Type | SIFT value | SIFT prediction |
|---|---|---|---|---|---|---|---|---|---|---|
| rs109808135 | 2 | 105138712 | SMARCAL1 | ENSBTAG00000003843 | C/T | 338072 | Karisa_et_al_2014 | Missense | 0.49 | tolerated |
| rs109231130 | 2 | 105138883 | SMARCAL1 | ENSBTAG00000003843 | G/C | 338072 | Karisa_et_al_2014 | Missense | 0.61 | tolerated |
| rs110348122 | 2 | 105139011 | SMARCAL1 | ENSBTAG00000003843 | C/A | 338072 | Karisa_et_al_2014 | Missense | 0.23 | tolerated |
| rs109382589 | 2 | 105158290 | SMARCAL1 | ENSBTAG00000003843 | T/G | 338072 | Karisa_et_al_2014 | Missense | 0.02 | deleterious |
| rs208660945 | 2 | 105170755 | SMARCAL1 | ENSBTAG00000003843 | C/T | 338072 | Karisa_et_al_2014 | Missense | 0.15 | tolerated |
| rs110703596 | 2 | 133933240 | PQLC2 | ENSBTAG00000013650 | T/C | 512930 | Karisa_et_al_2014 | Missense | 0.68 | tolerated-low confidence |
| rs208204723 | 2 | 133933770 | PQLC2 | ENSBTAG00000013650 | G/C | 512930 | Karisa_et_al_2014 | Missense | | deleterious-low confidence |
| rs380858825 | 2 | 133933915 | PQLC2 | ENSBTAG00000013650 | G/A | 512930 | Karisa_et_al_2014 | Missense | | tolerated-low confidence |
| rs209148339 | 2 | 133935523 | PQLC2 | ENSBTAG00000013650 | T/C | 512930 | Karisa_et_al_2014 | Missense | 0.21 | |
| rs43330774 | 2 | 136261151 | NECAP2 | ENSBTAG00000013282 | G/A | 509439 | Karisa_et_al_2014 | Splice Region | — | |
| rs211650382 | 3 | 7809972 | ATF6 | ENSBTAG00000046152 | C/T | 530610 | Karisa_et_al_2014 | Missense | 0.42 | tolerated |
| rs42417924 | 3 | 70997059 | LRRIQ3 | ENSBTAG00000005227 | C/G | 523789 | Abo-Ismail_et_al_2014 | 3_prime_UTR_variant | | |
| rs42317715 | 4 | 81074177 | SUGCT | ENSBTAG00000019401 | T/C | 100125578 | Abo-Ismail_et_al_2014 | SPLICE_SITE | | |
| rs29004488 | 4 | 93262056 | LEP | ENSBTAG00000032121 | T/C | 280836 | Karisa_et_al_2014 | Missense Variant | 0.57 | tolerated |
| rs137095760 | 4 | 106138003 | MGAM | ENSBTAG00000014911 | T/G | 100336421 | Rolf_et_al_2011 | Missense | 0.01 | deleterious |
| rs110632853 | 4 | 106144905 | MGAM | ENSBTAG00000046152 | G/C | 100336421 | Rolf_et_al_2011 | Missense | | deleterious |
| rs110519795 | 4 | 117582537 | DPP6 | ENSBTAG00000021941 | A/G | 281123 | Serão et al. BMC Genetics 2013, 14:94 | Missense | 0.5 | tolerated |
| rs132717265 | 4 | 117658647 | DPP6 | ENSBTAG00000021941 | G/A | 281123 | Serão et al. BMC Genetics 2013, 14:94 | Splice Region | — | |
| rs109314460 | 4 | 117907734 | INSIG1 | ENSBTAG00000001592 | A/G | 511899 | Karisa_et_al_2014 | missense variant | 0.22 | tolerated-low confidence |
| rs132883023 | 5 | 30159194 | FAIM2 | ENSBTAG00000017504 | G/A | 509790 | Rolf_et_al_2011 | | 0.01 | deleterious |
| rs109392049 | 5 | 36027229 | NELL2 | ENSBTAG00000032183 | G/A | 524622 | | Missense | 0.17 | tolerated |

TABLE 8-continued

| NCBI_dbSNP_rs_ID | Chromosome Name | Base Pair Position | Gene Name | Ensembl Gene ID | Alleles | EntrezGene ID | Author for reference population | Variant Type | SIFT value | SIFT prediction |
|---|---|---|---|---|---|---|---|---|---|---|
| rs109499238 | 5 | 112922677 | CHADL | ENSBTAG00000012481 | A/C/G/T | 616055 | Abo-Ismail_et_al_2014 | missense_variant | 0.13 | tolerated |
| rs41574929 | 6 | 35938366 | CCSER1 | ENSBTAG00000019808 | G/T | 616908 | Abo-Ismail_et_al_2014 | 5_prime_UTR_variant | | |
| rs134225543 | 6 | 37896750 | PPM1K | ENSBTAG00000005754 | C/T | 540329 | Abo-Ismail_et_al_2014 | 3_prime_UTR_variant | | |
| rs110362902 | 6 | 37994986 | ABCG2 | ENSBTAG00000017704 | T/C | 536203 | Abo-Ismail_et_al_2014 | synonymous_variant | | |
| rs29010895 | 6 | 38042011 | PKD2 | ENSBTAG00000020031 | C/T | 530393 | Abo-Ismail_et_al_2014 | 3_prime_UTR_variant | | |
| rs29010894 | 6 | 38042286 | PKD2 | ENSBTAG00000020031 | C/T | 530393 | Abo-Ismail_et_al_2014 | 3_prime_UTR_variant | | |
| rs43702346 | 6 | 38048024 | PKD2 | ENSBTAG00000020031 | G/T | 530393 | Abo-Ismail_et_al_2014 | synonymous_variant | | |
| rs207525537 | 6 | 105377905 | EVC2 | ENSBTAG00000004277 | C/T | 280834 | Abo-Ismail_et_al_2014 | Missense | 0.02 | deleterious |
| rs41257208 | 6 | 113648200 | BOD1L | ENSBTAG00000004316 | A/G | 508527 | Abo-Ismail_et_al_2014 | 3_prime_UTR_variant | | |
| rs384300699 | 7 | 17044598 | PRKCSH | ENSBTAG00000008202 | G/A | 338067 | Rolf_et_al_2011 | | | deleterious |
| rs109557839 | 7 | 23867466 | ACSL6 | ENSBTAG00000019708 | G/A | 506059 | Saatchi_et_al_2014 | | 0.01 | deleterious |
| rs109305471 | 7 | 26329353 | SLC27A6 | ENSBTAG00000004860 | T/A | 537062 | cannor_et_al_2009 | | 0.01 | deleterious |
| rs109727850 | 7 | 98485261 | CAST | ENSBTAG00000000874 | A/G | 281039 | Karisa_et_al_2014 | Missense | 0.82 | tolerated |
| rs137601357 | 7 | 98485273 | CAST | ENSBTAG00000000874 | T/C/G | 281039 | Karisa_et_al_2014 | Missense | 0.49 | tolerated |
| rs210072660 | 7 | 98535683 | CAST | ENSBTAG00000000874 | A/G | 281039 | Karisa_et_al_2014 | Missense | 1 | tolerated |
| rs384020496 | 7 | 98535716 | CAST | ENSBTAG00000000874 | G/A | 281039 | Karisa_et_al_2014 | Missense | 1 | tolerated |
| rs133057384 | 7 | 98551339 | CAST | ENSBTAG00000000874 | G/A | 281039 | Karisa_et_al_2014 | Splice Region | — | |
| rs109384915 | 7 | 98554459 | CAST | ENSBTAG00000000874 | T/C | 281039 | Karisa_et_al_2014 | Missense | 0.84, 0.83, 0.82 | tolerated |
| rs110712559 | 7 | 98560787 | CAST | ENSBTAG00000000874 | A/G | 281039 | Karisa_et_al_2014 | Splice Region | — | |
| rs110711318 | 7 | 98563483 | CAST | ENSBTAG00000000874 | C/T | 281039 | Karisa_et_al_2014 | Splice Region | — | |
| rs136892391 | 8 | 10456250 | ELP3 | ENSBTAG00000002730 | G/A/C/T | 784720 | Abo-Ismail_et_al_2014 | 3_prime_UTR_variant | | |
| rs137400016 | 8 | 77290760 | CNTFR | ENSBTAG00000015361 | C/T | 539548 | Serão et al. BMC Genetics 2013, 14:94 | 5 Prime UTR | | |
| rs43593167 | 9 | 32473266 | FAM184A | ENSBTAG00000015467 | C/T | 541122 | Abo-Ismail_et_al_2014 | synonymous_variant | | |

TABLE 8-continued

| NCBI_dbSNP_rs_ID | Chromosome Name | Base Pair Position | Gene Name | Ensembl Gene ID | Alleles | EntrezGene ID | Author for reference population | Variant Type | SIFT value | SIFT prediction |
|---|---|---|---|---|---|---|---|---|---|---|
| rs451808712 | 9 | 101960877 | C6orf118 | ENSBTAG00000015485 | A/C | 515846 | Rolf_et_al_2011 | synonymous_variant | | deleterious |
| rs137496481 | 10 | 49901757 | ANXA2 | ENSBTAG00000009615 | C/T | 282689 | Abo-Ismail_et_al_2014 | 3_prime_UTR_variant | | |
| rs471723345 | 10 | 4990425 | ANXA29 | ENSBTAG00000009615 | G/A | 282689 | Abo-Ismail_et_al_2014 | 3_prime_UTR_variant | | |
| rs208224478 | 10 | 77389928 | RAB15 | ENSBTAG00000003474 | C/A/G/T | 614507 | Abo-Ismail_et_al_2014 | synonymous_variant | | |
| rs110711078 | 11 | 389115 | MERTK | ENSBTAG00000005828 | A/C/G/T | 504429 | Abo-Ismail_et_al_2014 | 3_prime_UTR_variant | | |
| rs43657898 | 11 | 3589846 | CNGA3 | ENSBTAG00000009834 | T/A | 281701 | Abo-Ismail_et_al_2014 | | | |
| rs42275280 | 11 | 4671286 | AFF3 | ENSBTAG00000012449 | C/T | 787488 | Yao_et_al_2013 | | 0.01 | deleterious |
| rs382292677 | 11 | 6039571 | TBC1D8 | ENSBTAG00000025898 | C/A | 527162 | Yao_et_al_2013 | | | deleterious |
| rs43673198 | 11 | 28809663 | ATP6V1E2 | ENSBTAG00000013734 | T/C | 540113 | Abo-Ismail_et_al_2014 | 5_prime_UTR_variant | | |
| rs441516506 | 11 | 38706801 | CCDC85A | ENSBTAG00000012394 | G/A | 525800 | Rolf_et_al_2011 | | | |
| rs133716845 | 12 | 83085664 | ERCC5 | ENSBTAG00000014043 | C/T | 509602 | Abo-Ismail_et_al_2014 | synonymous_variant | | |
| rs110323635 | 14 | 2239085 | MAPK15 | ENSBTAG00000019864 | G/A/C/T | 512125 | Abo-Ismail_et_al_2014 | | 1 | tolerated |
| rs109575847 | 14 | 5603441 | FAM135B | ENSBTAG00000018218 | G/A | 618755 | Serão et al. BMC Genetics 2013, 14:94 | | 0 | deleterious |
| rs133015776 | 14 | 9443813 | TG | ENSBTAG00000007823 | C/T | 280706 | | Missense | 0.29 | tolerated |
| rs133269500 | 14 | 9469795 | TG | ENSBTAG00000007823 | G/A | 280706 | | Missense | 0.13 | tolerated |
| rs110547220 | 14 | 9508873 | TG | ENSBTAG00000007823 | G/A/C | 280706 | | Missense | 0.31 | tolerated |
| rs208793983 | 14 | 23155663 | RB1CC1 | ENSBTAG00000000878 | C/A/G/T | 539858 | Abo-Ismail_et_al_2014 | missense_variant | 1 | tolerated |
| rs109800133 | 14 | 23161253 | RB1CC1 | ENSBTAG00000000878 | T/A/C/G | 539858 | Abo-Ismail_et_al_2014 | | 1 | tolerated – low confidence |
| rs41745621 | 15 | 5680312 | | ENSBTAG00000019309 | G/A | 512287 | Abo-Ismail_et_al_2014 | synonymous_variant | | |
| rs42544329 | 15 | 9690877 | CNTN5 | ENSBTAG00000020466 | G/T | 538198 | Abo-Ismail_et_al_2014 | synonymous_variant | | |
| rs42235500 | 15 | 17415692 | ELMOD1 | ENSBTAG00000002691 | G/A | 768233 | Serão et al. BMC Genetics 2013, 14:94 | Splice Region | — | |
| rs449702015 | 15 | 32674668 | SORL1 | ENSBTAG00000014611 | C/T | 533166 | Abo-Ismail_et_al_2014 | | 0.01 | deleterious |

TABLE 8-continued

| NCBI_dbSNP_rs_ID | Chromosome Name | Base Pair Position | Gene Name | Ensembl Gene ID | Alleles | EntrezGene ID | Author for reference population | Variant Type | SIFT value | SIFT prediction |
|---|---|---|---|---|---|---|---|---|---|---|
| rs208805443 | 15 | 32681447 | SORL1 | ENSBTAG00000014611 | G/A | 533166 | Abo-Ismail_et_al_2014 | missense variant | 0.5 | tolerated |
| rs41756484 | 15 | 34750064 | GRAMD1B | ENSBTAG00000001410 | G/A | 517332 | Serão et al. BMC Genetics 2013, 14:94 | Missense | 0.55 | tolerated |
| rs41756519 | 15 | 34754872 | GRAMD1B | ENSBTAG00000001410 | T/C | 517332 | Serão et al. BMC Genetics 2013, 14:94 | Splice Region | — | |
| rs42562042 | 15 | 36160748 | PLEKHA7 | ENSBTAG00000006974 | G/T | 528261 | Karisa_et_al_2014 | Missense | 0.66 | tolerated |
| rs41761878 | 15 | 42385243 | ZBED5 | ENSBTAG00000010568 | T/C | 539898 | Abo-Ismail_et_al_2014 | synonymous_variant | | |
| rs41772016 | 15 | 51796947 | LOC618173 | ENSBTAG00000005070 | T/G | 618173 | Lindholm-Perry_e_2015 | | | |
| rs43705159 | 15 | 66208534 | APIP | ENSBTAG00000018257 | C/T | 508345 | Karisa_et_al_2014 | missense_variant | 1 | tolerated |
| rs109778625 | 15 | 66231595 | APIP | ENSBTAG00000021661 | C/A | 537782 | Abo-Ismail_et_al_2014 | 5 PrimeUTR | — | |
| rs42536153 | 15 | 79136152 | LOC514818 | ENSBTAG00000005914 | G/A | 514818 | Rolf_et_al_2011 | | | deleterious |
| rs42573278 | 16 | 65065063 | RGSL1 | ENSBTAG00000018220 | G/C | 509065 | Abo-Ismail_et_al_2014 | missense_variant | 0.36 | tolerated |
| rs41816109 | 16 | 65097642 | RNASEL | ENSBTAG00000009091 | A/G | 100048947 | Abo-Ismail_et_al_2014 | 3_prime_UTR_variant | | |
| rs41817045 | 16 | 65111693 | RNASEL | ENSBTAG00000009091 | T/C | 100048947 | Abo-Ismail_et_al_2014 | synonymous_variant | | |
| rs109345460 | 16 | 68407342 | HMCN1 | ENSBTAG00000002730 | A/G | 784720 | Abo-Ismail_et_al_2014 | Missense | — | |
| rs109961941 | 16 | 68407519 | HMCN1 | ENSBTAG00000002730 | C/A | 784720 | Abo-Ismail_et_al_2014 | Missense | — | |
| rs41824268 | 16 | 68409088 | HMCN1 | ENSBTAG00000002730 | G/A | 784720 | Abo-Ismail_et_al_2014 | Missense | | |
| rs211555481 | 16 | 68490341 | HMCN1 | ENSBTAG00000002730 | G/A | 784720 | Abo-Ismail_et_al_2014 | Missense | | |
| rs209074324 | 16 | 68516295 | HMCN1 | ENSBTAG00000002730 | A/G | 784720 | Abo-Ismail_et_al_2014 | Missense | | |
| rs381726438 | 16 | 68596680 | HMCN1 | ENSBTAG00000002730 | C/T | 784720 | Abo-Ismail_et_al_2014 | Missense | | |
| rs209012152 | 16 | 68610038 | HMCN1 | ENSBTAG00000002730 | G/A | 784720 | Abo-Ismail_et_al_2014 | Missense | — | |
| rs41821600 | 16 | 68614446 | HMCN1 | ENSBTAG00000015235 | T/A | 521326 | Abo-Ismail_et_al_2014 | missense_variant | | |
| rs210494625 | 16 | 68617900 | HMCN1 | ENSBTAG00000002730 | A/G | 784720 | Abo-Ismail_et_al_2014 | Missense | | |
| rs209439233 | 16 | 68632777 | HMCN1 | ENSBTAG00000002730 | G/A | 784720 | Abo-Ismail_et_al_2014 | Missense | | |
| rs41821545 | 16 | 68672449 | HMCN1 | ENSBTAG00000002730 | A/C | 784720 | Abo-Ismail_et_al_2014 | Missense | | |

TABLE 8-continued

| NCBI_dbSNP_rs_ID | Chromosome Name | Base Pair Position | Gene Name | Ensembl Gene ID | Alleles | EntrezGene ID | Author for reference population | Variant Type | SIFT value | SIFT prediction |
|---|---|---|---|---|---|---|---|---|---|---|
| rs41820824 | 16 | 68690299 | HMCN1 | ENSBTAG00000015235 | C/T | 521326 | Abo-Ismail_et_al_2014 | SPLICE_SITE | | |
| rs210219754 | 17 | 63702804 | RPH3A | ENSBTAG00000004247 | C/A/G/T | 282044 | Abo-Ismail_et_al_2014 | synonymous_variant | | |
| rs437019228 | 17 | 66535047 | CORO1C | ENSBTAG00000007993 | G/A | 515798 | Abo-Ismail_et_al_2014 | missense_variant | 1 | tolerated |
| rs29010201 | 18 | 50581375 | CYP2B | ENSBTAG00000003871 | C/T | 504769 | Karisa_et_al_2014 | missense_variant | 0.1 | tolerated |
| rs476872493 | 19 | 36758184 | CACNA1G | ENSBTAG00000009835 | G/A | 282411 | Abo-Ismail_et_al_2014 | | | deleterious |
| rs41920005 | 19 | 51384984 | FASN | ENSBTAG00000015980 | C/G | 281152 | | 5 Prime UTR | | |
| rs41919993 | 19 | 51397250 | FASN | ENSBTAG00000015980 | T/C | 281152 | | Missense | 0.62 | tolerated |
| rs41919985 | 19 | 51402032 | FASN | ENSBTAG00000015980 | G/A | 281152 | | Missense | 0.14 | tolerated |
| rs137133778 | 20 | 10159258 | OCLN | ENSBTAG00000000561 | T/A | 512405 | Karisa_et_al_2014 | Splice Region | — | |
| rs134264563 | 20 | 10167825 | OCLN | ENSBTAG00000000561 | A/G | 512405 | Karisa_et_al_2014 | Missense | 0.21 | tolerated |
| rs109638814 | 20 | 10186470 | OCLN | ENSBTAG00000000561 | A/G | 512405 | Karisa_et_al_2014 | Missense | 1 | tolerated |
| rs109960657 | 20 | 10193691 | OCLN | ENSBTAG00000000561 | G/A | 512405 | Karisa_et_al_2014 | 5 Prime UTR | — | |
| rs207541156 | 20 | 16853465 | IPO11 | ENSBTAG00000018616 | C/A/G/T | 538236 | Abo-Ismail_et_al_2014 | missense_variant | 0.12 | tolerated |
| rs109300983 | 20 | 31891050 | GHR | ENSBTAG00000001335 | T/C | 280805 | Karisa_et_al_2014 | Missense | 0.09 | tolerated |
| rs209676814 | 20 | 31891107 | GHR | ENSBTAG00000001335 | C/T | 280805 | Karisa_et_al_2014 | Missense | 0.08 | tolerated |
| rs110265189 | 20 | 31891130 | GHR | ENSBTAG00000001335 | T/G | 280805 | Karisa_et_al_2014 | Missense | 0.02 | deleterious |
| rs385640152 | 20 | 31909478 | GHR | ENSBTAG00000001335 | A/T | 280805 | Karisa_et_al_2014 | Missense | 0.02 | deleterious |
| rs108994622 | 20 | 35521670 | OSMR | ENSBTAG00000033107 | T/G | 514720 | Rolf_et_al_2011 | Missense | 0.33 | tolerated |
| rs41580312 | 20 | 35544340 | OSMR | ENSBTAG00000033107 | C/A | 514720 | Rolf_et_al_2011 | Missense | 0.06 | tolerated |
| rs41947101 | 20 | 35561705 | OSMR | ENSBTAG00000033107 | T/A | 514720 | Rolf_et_al_2011 | Missense | 1 | tolerated |
| rs378496139 | 20 | 35942739 | LIFR | ENSBTAG00000010423 | G/A | 539504 | Karisa_et_al_2014 | missense variant | 1 | tolerated |
| rs42345570 | 20 | 38200342 | UGT3A1 | ENSBTAG00000002701 | A/C | 537188 | Karisa_et_al_2014 | Splice Region | — | |
| rs109332450 | 20 | 38200470 | UGT3A1 | ENSBTAG00000002701 | C/T | 537188 | Karisa_et_al_2014 | Missense | 0.09 | tolerated |
| rs134703045 | 20 | 38204849 | UGT3A1 | ENSBTAG00000002701 | A/C | 537188 | Karisa_et_al_2014 | Splice Region | — | |
| rs135350417 | 20 | 38205025 | UGT3A1 | ENSBTAG00000002701 | T/C | 537188 | Karisa_et_al_2014 | Missense | 0.48 | tolerated |

TABLE 8-continued

| NCBI_dbSNP_rs_ID | Chromosome Name | Base Pair Position | Gene Name | Ensembl Gene ID | Alleles | EntrezGene ID | Author for reference population | Variant Type | SIFT value | SIFT prediction |
|---|---|---|---|---|---|---|---|---|---|---|
| rs133951891 | 20 | 38205059 | UGT3A1 | ENSBTAG00000002701 | T/C | 537188 | Karisa_et_al_2014 | Missense | 0.08 | tolerated |
| rs134604394 | 20 | 39832043 | SLC45A2 | ENSBTAG00000018235 | T/A | 538746 | Karisa_et_al_2014 | Missense | 1 | tolerated |
| rs41946086 | 20 | 39867446 | SLC45A2 | ENSBTAG00000018235 | G/A | 538746 | Karisa_et_al_2014 | Missense | 1 | tolerated |
| rs43020736 | 21 | 29654483 | PCSK6 | ENSBTAG00000006675 | C/T | 524684 | Abo-Ismail_et_al_2014 | missense_variant | 0.01 | deleterious |
| rs208239648 | 22 | 17961710 | LMCD1 | ENSBTAG00000005431 | C/A/G/T | 540474 | Abo-Ismail_et_al_2014 | missense_variant | 0.15 | tolerated-low |
| rs133838809 | 22 | 57046580 | TMEM40 | ENSBTAG00000000161 | T/C | 505490 | Serão et al. BMC Genetics 2013, 14:94 | Missense | 1 | tolerated |
| rs132658346 | 22 | 57050048 | TMEM40 | ENSBTAG00000000161 | A/G | 505490 | Serão et al. BMC Genetics 2013, 14:94 | Missense | 0.99 | tolerated |
| rs43563315 | 22 | 57056954 | TMEM40 | ENSBTAG00000000161 | C/G | 505490 | Serão et al. BMC Genetics 2013, 14:94 | Splice Region | — | |
| rs378726699 | 23 | 32030037 | CARMIL1 | ENSBTAG00000016549 | T/G | 537314 | Rolf_et_al_2011 | | | deleterious-low confidence |
| rs42342962 | 23 | 45276782 | PAK1IP1 | ENSBTAG00000018674 | C/T | 505125 | Serão et al. BMC Genetics 2013, 14:94 | Missense | 1 | tolerated |
| rs108968214 | 24 | 59670860 | MC4R | ENSBTAG00000019676 | G/C | 281300 | Abo-Ismail_et_al_2014 | Missense | 0.46 | tolerated |
| rs439445177 | 25 | 14699511 | LOC515570 | ENSBTAG00000017759 | C/T | 515570 | Yao_et_al_2013 | Missense | | deleterious |
| rs110700273 | 25 | 34725002 | POR | ENSBTAG00000017082 | C/T | 532512 | Abo-Ismail_et_al_2014 | missense variant | 0.21 | tolerated |
| rs110216983 | 26 | 47852389 | MKI67 | ENSBTAG00000002444 | A/G | 513220 | Karisa_et_al_2014 | Missense | — | |
| rs109930382 | 26 | 47852501 | MKI67 | ENSBTAG00000002444 | C/T | 513220 | Karisa_et_al_2014 | Missense | — | |
| rs109558734 | 26 | 47854998 | MKI67 | ENSBTAG00000002444 | C/G | 513220 | Karisa_et_al_2014 | Missense | — | |
| rs208328542 | 27 | 37068760 | C27H8orf40 | ENSBTAG00000000979 | C/T | 515895 | Abo-Ismail_et_al_2014 | 3_prime_UTR_variant | | |
| rs135814528 | 27 | 37070184 | C27H8orf40 | ENSBTAG00000000979 | A/G | 515895 | Abo-Ismail_et_al_2014 | 3_prime_UTR_variant | | |
| rs475737617 | 27 | 37328535 | HOOK3 | ENSBTAG00000007634 | C/G | 524648 | Rolf_et_al_2011 | | | deleterious |
| rs209765899 | 28 | 14993619 | PHYHIPL | ENSBTAG00000010947 | T/A | 780878 | Abo-Ismail_et_al_2014 | synonymous_variant | | |

TABLE 8-continued

| NCBI_dbSNP_rs_ID | Chromosome Name | Base Pair Position | Gene Name | Ensembl Gene ID | Alleles | EntrezGene ID | Author for reference population | Variant Type | SIFT value | SIFT prediction |
|---|---|---|---|---|---|---|---|---|---|---|
| rs42402428 | 29 | 6461861 | TYR | ENSBTAG00000011813 | C/T | 280951 | Abo-Ismail_et_al_2014 | synonymous_variant | | |
| rs42190891 | 29 | 46550309 | LRP5 | ENSBTAG00000005903 | A/G | 534450 | Karisa_et_al_2014 | missense variant | 1 | tolerated |

TABLE 9

| Animal Type | Alfalfa Silage | Barley Silage | Barley Grain | Supplement | Other | Count of Animals | Comment |
|---|---|---|---|---|---|---|---|
| Bulls | 0 | 30.82 | 48.64 | 5.26 | 15.28 | 120 | Other = Chopped hay |
| Bulls | 0 | 52.54 | 0 | 0 | 47.46 | 87 | Other = Beef developer pellet |
| Bulls | 0 | 53.45 | 0 | 0 | 46.55 | 77 | Other = Beef developer pellet |
| Heifer | 0 | 79.32 | 20.68 | 0 | 0 | 300 | |
| Heifer | 0 | 11 | 83.6 | 5.4 | 0 | 15 | |
| Steer | 0 | 11 | 83.6 | 5.4 | 0 | 83 | |
| Steer | 0 | 51.64 | 42.6 | 5.76 | 0 | 74 | |
| Steer | 0 | 16.5 | 77.8 | 5.7 | 0 | 9 | |
| Steer | 0 | 20.7 | 73.9 | 5.4 | 0 | 7 | |
| Steer | 0 | 21.3 | 69.4 | 9.3 | 0 | 8 | |
| Steer | 6.4 | 9.4 | 74.2 | 10 | 0 | 8 | |
| Steer | 0 | 16.5 | 77.8 | 5.7 | 0 | 7 | |
| Steer | 0 | 20.7 | 73.9 | 5.4 | 0 | 8 | |
| Steer | 0 | 21.3 | 69.4 | 9.3 | 0 | 5 | |
| Steer | 6.4 | 9.4 | 74.2 | 10 | 0 | 8 | |
| Steer | 0 | 16.5 | 77.8 | 5.7 | 0 | 7 | |
| Steer | 0 | 20.7 | 73.9 | 5.4 | 0 | 9 | |
| Steer | 0 | 21.3 | 69.4 | 9.3 | 0 | 8 | |
| Steer | 6.4 | 9.4 | 74.2 | 10 | 0 | 8 | |
| Steer | 0 | 16.5 | 77.8 | 5.7 | 0 | 5 | |
| Steer | 0 | 20.7 | 73.9 | 5.4 | 0 | 7 | |
| Steer | 0 | 21.3 | 69.4 | 9.3 | 0 | 8 | |
| Steer | 6.4 | 9.4 | 74.2 | 10 | 0 | 8 | |

Note:
Beef developer pellet analyses
Crude Protein Min. 15.00%
Crude Fat Min. 2.00%
Crude Fibre Max. 12.00%
Calcium Actual 1.05%
Phosphorus Actual 0.43%
Sodium Actual 0.21%
Vitamin A Min. 6580 IU/kg
Vitamin D Min. 1462 IU/kg
Vitamin E Min. 30 IU/kg

TABLE 10

| Trait | No. Records |
|---|---|
| ADG, kg/d | 875 |
| DMI, kg | 863 |
| MMWT, kg | 877 |
| RFI, kg/d | 847 |
| RFIf, kg/d | 391 |
| BFat, mm | 537 |
| FCR | 819 |
| RG | 848 |
| RGf | 390 |

TABLE 11

| Gene_Name | rs_same | chr | adg_addPV | sig_ADG | DMI_addPV | sig_DMI | mmwt_addPV | sig_MMWT | rfi_addPV | sig_RFI | rfif_addPV | sig_RFif | bfat_addPV | sig_BFAT |
|---|---|---|---|---|---|---|---|---|---|---|---|---|---|---|
| SMARCAL1 | rs208660945 | 2 | 0.308 | | 0.740 | | 0.471 | | 0.807 | | 0.863 | | 0.092 | sig_BFAT |
| DPP6 | rs132717265 | 4 | 0.169 | | 0.015 | sig_DMI | 0.008 | sig_MMWT | 0.410 | | 0.740 | | 0.255 | |
| CNGA3 | rs43657898 | 11 | 0.584 | | 0.498 | | 0.807 | | 0.138 | | 0.141 | | 0.118 | |
| HMCN1 | rs211555481 | 16 | 0.863 | | 0.888 | | 0.920 | | 0.655 | | 0.752 | | 0.024 | sig_BFAT |
| ABCG2 | rs110362902 | 6 | 0.025 | sig_ADG | 0.020 | sig_DMI | | | 0.610 | | 0.604 | | 0.888 | |
| RB1CC1 | rs109800133 | 14 | 0.680 | | 1.000 | | 1.000 | | 0.791 | | 0.699 | | 0.920 | |
| SLC45A2 | rs134604394 | 20 | 0.276 | | 0.719 | | 0.863 | | 0.699 | | 0.436 | | 1.000 | |
| PKD2 | rs29010894 | 6 | 0.313 | | 0.110 | | 0.184 | | 0.549 | | 0.513 | | 0.193 | |
| EVC2 | rs207525537 | 6 | 0.920 | | 0.278 | | 0.663 | | 0.088 | sig_RFI | 0.342 | | 0.543 | |
| CAST | rs137601357 | 7 | 0.807 | | 0.920 | | 1.000 | | 0.374 | | 0.226 | | 0.295 | |
| SMARCAL1 | rs110348122 | 2 | 0.532 | | 0.708 | | 0.489 | | 0.538 | | 0.625 | | 0.208 | |
| GHR | rs385640152 | 20 | 0.791 | | 0.0336 | sig_DMI | 0.360 | | 0.0308 | sig_RFI | 0.863 | | |
| SMARCAL1 | rs109808135 | 2 | 0.538 | | 0.699 | | 0.498 | | 0.533 | | 0.617 | | 0.198 | |
| CAST | rs384020496 | 7 | 1.000 | | 0.103 | | 0.127 | | 0.055 | sig_RFI | 0.132 | | 0.823 | |
| CNTFR | rs137400016 | 8 | 0.356 | | 0.689 | | 0.740 | | 0.318 | | 0.378 | | 0.239 | |
| DPP6 | rs110519795 | 4 | 0.475 | | 1.000 | | 0.420 | | 0.655 | | 1.000 | | 0.863 | |
| PAK1IP1 | rs42342962 | 23 | 1.000 | | 0.888 | | 0.354 | | 0.352 | | NA | | 0.096 | sig_BFAT |
| CAST | rs210072660 | 7 | 0.920 | | 0.807 | | 0.920 | | 0.218 | | 0.118 | | 0.357 | |
| HMCN1 | rs381726438 | 16 | 0.764 | | 0.584 | | 0.699 | | 0.639 | | 0.920 | | 0.417 | |
| OCLN | rs134264563 | 20 | 0.503 | | 0.330 | | 0.235 | | 0.672 | | 0.689 | | 0.543 | |
| IPO11 | rs207541156 | 20 | 0.888 | | 0.623 | | 0.536 | | 0.764 | | NA | | 0.628 | |
| SMARCAL1 | rs109382589 | 2 | 0.377 | | 0.128 | | 0.043 | sig_MMWT | 0.560 | | 0.604 | | 0.091 | sig_BFAT |
| PCSK6 | rs43020736 | 21 | 0.400 | | 0.368 | | 1.000 | | 0.740 | | 0.820 | | 0.888 | |
| SMARCAL1 | rs109065702 | 2 | 0.417 | | 0.632 | | 0.455 | | 0.549 | | 0.709 | | 0.309 | |
| TMEM40 | rs133838809 | 22 | 1.000 | | 0.888 | | 0.387 | | 0.597 | | 0.920 | | 0.397 | |
| HMCN1 | rs41821600 | 16 | 0.086 | sig_ADG | 0.002 | sig_DMI | 0.120 | | 0.459 | | 0.920 | | 0.610 | |
| TG | rs133269500 | 14 | 0.295 | sig_ADG | 0.054 | sig_DMI | 0.214 | | 0.0279 | sig_RFI | 0.447 | | 0.920 | |
| FAM135B | rs109575847 | 14 | 0.522 | | 0.410 | | 0.584 | | 0.037 | sig_RFI | 0.421 | | 0.443 | |
| HMCN1 | rs209439233 | 16 | 0.604 | | 0.224 | | 0.791 | | 0.708 | | NA | | 0.920 | |
| MGAM | rs110632853 | 4 | 0.752 | | 0.198 | | 0.318 | | 0.035 | sig_RFI | 0.920 | | 0.752 | |
| OSMR | rs41947101 | 20 | 0.655 | | 0.672 | | NA | | 0.512 | | 1.000 | | 0.920 | |
| TG | rs110547220 | 14 | 0.639 | | 0.647 | | 0.888 | | 0.106 | | 0.233 | | 0.920 | |
| HMCN1 | rs208012152 | 16 | 0.764 | | 0.598 | | 0.493 | | 0.543 | | 0.647 | | 0.604 | |
| HMCN1 | rs210494625 | 16 | 0.549 | | 0.343 | | 1.000 | | 0.729 | | 0.719 | | 0.863 | |
| MKI67 | rs109930382 | 26 | 0.249 | | | | 0.295 | | 0.260 | | 0.719 | | 0.002 | sig_BFAT |
| MAPK1S | rs110323635 | 14 | 0.560 | | | | 0.286 | | 0.297 | | 0.355 | | 0.610 | |
| MKI67 | rs110216983 | 26 | 0.208 | | | | 0.274 | | 0.115 | | 0.341 | | 0.001 | sig_BFAT | confirmed to affect (P <= 0.1) the same trait in the current population as in the UAS paper population
significant in the current population for other traits

TABLE 12

| NCBI_dbSNP_rs_ID | Chromosome Name | Base Pair Position | Gene Name | Ensembl Gene ID | Alleles | Entrez Gene ID | Author for reference population | Variant Type | SIFT value | SIFT prediction | Example 3_62SNPs | Example 4_72SNPs |
|---|---|---|---|---|---|---|---|---|---|---|---|---|
| rs109065702 | 2 | 105138600 | SMARCAL1 | ENSBTAG00000003843 | T/C | 338072 | Karisa_et_al_2014 | Missense | 0.42 | tolerated | . | Sig10_62SNP |
| rs109314460 | 4 | 117907734 | INSIG1 | ENSBTAG00000001592 | A/G | 511899 | Karisa_et_al_2014 | missense_variant | 0.22 | tolerated-low confidence | Sig10_62SNP | Sig10_62SNP |
| rs109382589 | 2 | 105158290 | SMARCAL1 | ENSBTAG00000003843 | T/G | 338072 | Karisa_et_al_2014 | Missense | 0.02 | deleterious | Sig10_62SNP | Sig10_62SNP |
| rs109392049 | 5 | 36027229 | NELL2 | ENSBTAG00000032183 | G/A | 524622 |  | Missense | 0.17 | tolerated | . | Sig10_62SNP |
| rs109575847 | 14 | 5603441 | FAM135B | ENSBTAG00000018218 | G/A | 618755 | Serão et al. BMC Genetics 2013, 14:94 |  | 0 | deleterious | Sig10_62SNP | Sig10_62SNP |
| rs109800133 | 14 | 23161253 | RB1CC1 | ENSBTAG00000000878 | T/A/C/G | 539858 | Abo-Ismail_et_al_2014 |  | 1 | tolerated-low confidence | . | Sig10_62SNP |
| rs109808135 | 2 | 105138712 | SMARCAL1 | ENSBTAG00000003843 | C/T | 338072 | Karisa_et_al_2014 | Missense | 0.49 | tolerated | . | Sig10_62SNP |
| rs109930382 | 26 | 47852501 | MKI67 | ENSBTAG00000002444 | C/T | 513220 | Karisa_et_al_2014 | Missense | — |  | Sig10_62SNP | Sig10_62SNP |
| rs110216983 | 26 | 47852389 | MKI67 | ENSBTAG00000002444 | A/G | 513220 | Karisa_et_al_2014 | Missense | — |  | . | Sig10_62SNP |
| rs110323635 | 14 | 2239085 | MAPK15 | ENSBTAG00000019864 | G/A/C/T | 512125 | Abo-Ismail_et_al_2014 |  | 1 | tolerated | . | Sig10_62SNP |
| rs110348122 | 2 | 105139011 | SMARCAL1 | ENSBTAG00000003843 | C/A | 338072 | Karisa_et_al_2014 | Missense | 0.23 | tolerated | . | Sig10_62SNP |
| rs110362902 | 6 | 37994986 | ABCG2 | ENSBTAG00000017704 | T/C | 536203 | Abo-Ismail_et_al_2014 | synonymous_variant |  |  | Sig10_62SNP | Sig10_62SNP |

TABLE 12-continued

| NCBI_dbSNP_rs_ID | Chromosome Name | Base Pair Position | Gene Name | Ensembl Gene ID | Alleles | Entrez Gene ID | Author for reference population | Variant Type | SIFT value | SIFT prediction | Example 3_62SNPs | Example 4_72SNPs |
|---|---|---|---|---|---|---|---|---|---|---|---|---|
| rs110519795 | 4 | 117582537 | DPP6 | ENSBTAG00000021941 | A/G | 281123 | Serão et al. BMC Genetics 2013, 14:94 | Missense | 0.5 | tolerated | . | Sig10_62SNP |
| rs110547220 | 14 | 9508873 | TG | ENSBTAG00000007823 | G/A/C | 280706 | | Missense | 0.31 | tolerated | Sig10_62SNP | Sig10_62SNP |
| rs110632853 | 4 | 106144905 | MGAM | ENSBTAG00000046152 | G/C | 100336421 | Rolf_et_al_2011 | | | deleterious | Sig10_62SNP | Sig10_62SNP |
| rs110712559 | 7 | 98560787 | CAST | ENSBTAG00000000874 | A/G | 281039 | Karisa_et_al_2014 | Splice Region | — | | Sig10_62SNP | Sig10_62SNP |
| rs110953962 | 1 | 69753035 | UMPS | ENSBTAG00000013727 | C/T | 281568 | Karisa_et_al_2014 | Missense | 0.01 | deleterious | . | Sig10_62SNP |
| rs132717265 | 4 | 117658647 | DPP6 | ENSBTAG00000021941 | G/A | 281123 | Serão et al. BMC Genetics 2013, 14:94 | Splice Region | — | | Sig10_62SNP | Sig10_62SNP |
| rs132883023 | 5 | 30159194 | FAIM2 | ENSBTAG00000017504 | G/A | 509790 | Rolf_et_al_2011 | | 0.01 | deleterious | Sig10_62SNP | Sig10_62SNP |
| rs133269500 | 14 | 9469795 | TG | ENSBTAG00000007823 | G/A | 280706 | | Missense | 0.13 | tolerated | Sig10_62SNP | Sig10_62SNP |
| rs133838809 | 22 | 57046580 | TMEM40 | ENSBTAG00000000161 | T/C | 505490 | Serão et al. BMC Genetics 2013, 14:94 | Missense | 1 | tolerated | . | Sig10_62SNP |
| rs134264563 | 20 | 10167825 | OCLN | ENSBTAG00000000561 | A/G | 512405 | Karisa_et_al_2014 | Missense | 0.21 | tolerated | Sig10_62SNP | Sig10_62SNP |
| rs134604394 | 20 | 39832043 | SLC45A2 | ENSBTAG00000018235 | T/A | 538746 | Karisa_et_al_2014 | Missense | 1 | tolerated | . | Sig10_62SNP |
| rs137400016 | 8 | 77290760 | CNTFR | ENSBTAG00000015361 | C/T | 539548 | Serão et al. BMC Genetics 2013, 14:94 | 5 Prime UTR | | | . | Sig10_62SNP |

TABLE 12-continued

| NCBI_dbSNP_rs_ID | Chromosome Name | Base Pair Position | Gene Name | Ensembl Gene ID | Alleles | Entrez Gene ID | Author for reference population | Variant Type | SIFT value | SIFT prediction | Example 3_62SNPs | Example 4_72SNPs |
|---|---|---|---|---|---|---|---|---|---|---|---|---|
| rs137601357 | 7 | 98485273 | CAST | ENSBTAG00000008074 | T/C/G | 281039 | Karisa_et_al_2014 | Missense | 0.49 | tolerated | . | Sig10_62SNP |
| rs207525537 | 6 | 105377905 | EVC2 | ENSBTAG00000042077 | C/T | 280834 | | Missense | 0.02 | deleterious | Sig10_62SNP | Sig10_62SNP |
| rs207541156 | 20 | 16853465 | IPO11 | ENSBTAG00000186016 | C/A/G/T | 538236 | Abo-Ismail_et_al_2014 | missense_variant | 0.12 | tolerated | . | Sig10_62SNP |
| rs208270150 | 1 | 138045480 | ACAD11 | ENSBTAG00000310010 | C/T | 526956 | Karisa_et_al_2014 | Missense | 0.24 | tolerated | Sig10_62SNP | Sig10_62SNP |
| rs208328542 | 27 | 37068760 | C27H8orf40 | ENSBTAG00000009079 | C/T | 515895 | Abo-Ismail_et_al_2014 | 3_prime_UTR_variant | | | Sig10_62SNP | Sig10_62SNP |
| rs208660945 | 2 | 105170755 | SMARCAL1 | ENSBTAG00000038043 | C/T | 338072 | Karisa_et_al_2014 | Missense | 0.15 | tolerated | Sig10_62SNP | Sig10_62SNP |
| rs208793983 | 14 | 23155663 | RB1CC1 | ENSBTAG00000008078 | C/A/G/T | 539858 | Abo-Ismail_et_al_2014 | missense_variant | 1 | tolerated | Sig10_62SNP | Sig10_62SNP |
| rs209012152 | 16 | 68610038 | HMCN1 | ENSBTAG00000027030 | G/A | 784720 | Abo-Ismail_et_al_2014 | Missense | | | . | Sig10_62SNP |
| rs209074324 | 16 | 68516295 | HMCN1 | ENSBTAG00000027030 | A/G | 784720 | Abo-Ismail_et_al_2014 | Missense | | | . | Sig10_62SNP |
| rs209439233 | 16 | 68632777 | HMCN1 | ENSBTAG00000027030 | G/A | 784720 | Abo-Ismail_et_al_2014 | Missense | | | . | Sig10_62SNP |
| rs210494625 | 16 | 68617900 | HMCN1 | ENSBTAG00000027030 | A/G | 784720 | Abo-Ismail_et_al_2014 | Missense | | | . | Sig10_62SNP |
| rs211555481 | 16 | 68490341 | HMCN1 | ENSBTAG00000027030 | G/A | 784720 | Abo-Ismail_et_al_2014 | Missense | | | Sig10_62SNP | Sig10_62SNP |
| rs29004488 | 4 | 93262056 | LEP | ENSBTAG00000 | T/C | 280836 | Karisa_et_al_2014 | Missense Variant | 0.57 | tolerated | . | Sig10_62SNP |

TABLE 12-continued

| NCBI_dbSNP_rs_ID | Chromosome Name | Base Pair Position | Gene Name | Ensembl Gene ID | Alleles | Entrez Gene ID | Author for reference population | Variant Type | SIFT value | SIFT prediction | Example 3_62SNPs | Example 4_72SNPs |
|---|---|---|---|---|---|---|---|---|---|---|---|---|
| rs29010894 | 6 | 38042286 | PKD2 | ENSBTAG00000014911 | C/T | 530393 | Abo-Ismail_et_al_2014 | 3_prime_UTR_variant | | | | Sig10_62SNP |
| rs378496139 | 20 | 35942739 | LIFR | ENSBTAG00000020031 | G/A | 539504 | Karisa_et_al_2014 | missense_variant | 1 | tolerated | Sig10_62SNP | Sig10_62SNP |
| rs381726438 | 16 | 68596680 | HMCN1 | ENSBTAG00000010423 | C/T | 784720 | Abo-Ismail_et_al_2014 | Missense | | | | Sig10_62SNP |
| rs384020496 | 7 | 98535716 | CAST | ENSBTAG00000002730 | G/A | 281039 | Karisa_et_al_2014 | Missense | 1 | tolerated | Sig10_62SNP | Sig10_62SNP |
| rs385640152 | 20 | 31909478 | GHR | ENSBTAG00000000874 | A/T | 280805 | Karisa_et_al_2014 | Missense | 0.02 | deleterious | Sig10_62SNP | Sig10_62SNP |
| rs41574929 | 6 | 35938366 | CCSER1 | ENSBTAG00000019835 | G/T | 616908 | Abo-Ismail_et_al_2014 | 5_prime_UTR_variant | | | Sig10_62SNP | Sig10_62SNP |
| rs41580312 | 20 | 35544340 | OSMR | ENSBTAG00000033108 | C/A | 514720 | Rolf_et_al_2011 | Missense | 0.06 | tolerated | Sig10_62SNP | Sig10_62SNP |
| rs41756484 | 15 | 34750064 | GRAMD1B | ENSBTAG00000014410 | G/A | 517332 | Serão et al. BMC Genetics 2013, 14:94 | Missense | 0.55 | tolerated | Sig10_62SNP | Sig10_62SNP |
| rs41821600 | 16 | 68614446 | HMCN1 | ENSBTAG00000015235 | T/A | 521326 | Abo-Ismail_et_al_2014 | missense_variant | | | Sig10_62SNP | Sig10_62SNP |
| rs41824268 | 16 | 68409088 | HMCN1 | ENSBTAG00000002730 | G/A | 784720 | Abo-Ismail_et_al_2014 | Missense | | | Sig10_62SNP | Sig10_62SNP |
| rs41947101 | 20 | 35561705 | OSMR | ENSBTAG00000033107 | T/A | 514720 | Rolf_et_al_2011 | Missense | 1 | tolerated | Sig10_62SNP | Sig10_62SNP |
| rs42345570 | 20 | 38200342 | UGT3A1 | ENSBTAG00000002701 | A/C | 537188 | Karisa_et_al_2014 | Splice Region | — | | Sig10_62SNP | Sig10_62SNP |

TABLE 12-continued

| NCBI_dbSNP_rs_ID | Chromosome Name | Base Pair Position | Gene Name | Ensembl Gene ID | Alleles | Entrez Gene ID | Author for reference population | Variant Type | SIFT value | SIFT prediction | Example 3_62SNPs | Example 4_72SNPs |
|---|---|---|---|---|---|---|---|---|---|---|---|---|
| rs43020736 | 21 | 29654483 | PCSK6 | ENSBTAG00000006675 | C/T | 524684 | Abo-Ismail_et_al_2014 | missense_variant | 0.01 | deleterious | . | Sig10_62SNP |
| rs43285609 | 1 | 146449085 | RRP1B | ENSBTAG00000017418 | G/A | 510240 | Yao_et_al_2013 | | 0.01 | deleterious | Sig10_62SNP | Sig10_62SNP |
| rs43563315 | 22 | 57056954 | TMEM40 | ENSBTAG00000000161 | C/G | 505490 | Serão et al. BMC Genetics 2013, 14:94 | Splice Region | — | | Sig10_62SNP | Sig10_62SNP |
| rs43657898 | 11 | 3589846 | CNGA3 | ENSBTAG00000009834 | T/A | 281701 | Abo-Ismail_et_al_2014 | 3_prime_UTR_variant | — | | Sig10_62SNP | Sig10_62SNP |
| rs43705159 | 15 | 66208534 | APIP | ENSBTAG00000018257 | C/T | 508345 | Karisa_et_al_2014 | missense_variant | 1 | tolerated | | Sig10_62SNP |
| rs438856835 | 2 | 41791856 | GALNT13 | ENSBTAG00000005562 | A/C | 532545 | Abo-Ismail_et_al_2014 | | — | deleterious | Sig10_62SNP | Sig10_62SNP |
| rs445312693 | 1 | 146457394 | RRP1B | ENSBTAG00000017418 | A/G | 510240 | Yao_et_al_2013 | | 0.13 | tolerated | Sig10_62SNP | Sig10_62SNP |
| rs450068075 | 2 | 30183902 | SCN9A | ENSBTAG00000002425 | C/T | 533065 | Rolf_et_al_2011 | | — | deleterious | Sig10_62SNP | Sig10_62SNP |
| rs108968214 | 24 | 59670860 | MC4R | ENSBTAG00000019676 | G/C | 281300 | | Missense | 0.46 | tolerated | Newdata_sig10 | |
| rs108991273 | 2 | 68111186 | DPP10 | ENSBTAG00000005252 | A/G | 617222 | Abo-Ismail_et_al_2014 | down-stream_gene_variant | — | | Newdata_sig10 | |
| rs108994622 | 20 | 35521670 | OSMR | ENSBTAG00000033107 | T/G | 514720 | Rolf_et_al_2011 | Missense | 0.33 | tolerated | Newdata_sig10 | |
| rs109305471 | 7 | 26329353 | SLC27A6 | ENSBTAG00000004860 | T/A | 537062 | cannor_et_al_2009 | | 0.01 | deleterious | Newdata_sig10 | |
| rs109345460 | 16 | 68407342 | HMCN1 | ENSBTAG00000 | A/G | 784720 | Abo-Ismail_et_al_2014 | Missense | — | | Newdata_sig10 | Newdata_sigTwo Models |

TABLE 12-continued

| NCBI_dbSNP_rs_ID | Chromosome Name | Base Pair Position | Gene Name | Ensembl Gene ID | Alleles | Entrez Gene ID | Author for reference population | Variant Type | SIFT value | SIFT prediction | Example 3_62SNPs | Example 4_72SNPs |
|---|---|---|---|---|---|---|---|---|---|---|---|---|
| rs109384915 | 7 | 98554459 | CAST | ENSBTAG00000027030 | T/C | 281039 | Karisa_et_al_2014 | Missense | 0.84, 0.83, 0.82 | tolerated | Newdata_sig10 | Newdata_sigTwo Models |
| rs109638814 | 20 | 10186470 | OCLN | ENSBTAG00000008074 | A/G | 512405 | Karisa_et_al_2014 | Missense | 1 | tolerated | | Sig10_62SNP |
| rs109778625 | 15 | 66231595 | APIP | ENSBTAG00000005061 | C/A | 537782 | Karisa_et_al_2014 | 5 PrimeUTR | — | | Newdata_sig10 | . |
| rs109961941 | 16 | 68407519 | HMCN1 | ENSBTAG00000021661 | C/A | 784720 | Abo-Ismail_et_al_2014 | Missense | — | | Newdata_sig10 | . |
| rs133015776 | 14 | 9443813 | TG | ENSBTAG00000027030 | C/T | 280706 | Karisa_et_al_2014 | Missense | 0.29 | tolerated | Newdata_sig10 | . |
| rs133951891 | 20 | 38205059 | UGT3A1 | ENSBTAG00000078023 | T/C | 537188 | Karisa_et_al_2014 | Missense | 0.08 | tolerated | Newdata_sig10 | . |
| rs208204723 | 2 | 133933770 | PQLC2 | ENSBTAG00000027001 | G/C | 512930 | Karisa_et_al_2014 | Missense | | | Newdata_sig10 | . |
| rs209676814 | 20 | 31891107 | GHR | ENSBTAG00000013650 | C/T | 280805 | Karisa_et_al_2014 | Missense | 0.08 | tolerated | Newdata_sig10 | Newdata_sigTwo Models |
| rs210072660 | 7 | 98535683 | CAST | ENSBTAG00000013035 | A/G | 281039 | Karisa_et_al_2014 | Missense | 1 | tolerated | | Sig10_62SNP |
| rs210293774 | 1 | 138014396 | ACAD11 | ENSBTAG00000008074 | G/C | 526956 | Karisa_et_al_2014 | Missense | | deleterious | | Sig10_62SNP |
| rs29010201 | 18 | 50581375 | CYP2B | ENSBTAG00000031010 | C/T | 504769 | Karisa_et_al_2014 | missense_variant | 0.1 | tolerated | Newdata_sig10 | Newdata_sigTwo Models |
| rs29010895 | 6 | 38042011 | PKD2 | ENSBTAG00000038071 | C/T | 530393 | Abo-Ismail_et_al_2014 | 3_prime_UTR_variant | | | Newdata_sig10 | Newdata_sigTwo Models |

TABLE 12-continued

| NCBI_dbSNP_rs_ID | Chromosome Name | Base Pair Position | Gene Name | Ensembl Gene ID | Alleles | Entrez Gene ID | Author for reference population | Variant Type | SIFT value | SIFT prediction | Example 3_62SNPs | Example 4_72SNPs |
|---|---|---|---|---|---|---|---|---|---|---|---|---|
| rs378726699 | 23 | 32030037 | CARMIL1 | ENSBTAG00000016549 | T/G | 537314 | Rolf_et_al_2011 | | | deleterious-low confidence | Newdata_sig10 | Newdata_sigTwo Models |
| rs382292677 | 11 | 6039571 | TBC1D8 | ENSBTAG00000025898 | C/A | 527162 | Yao_et_al_2013 | | | deleterious | Newdata_sig10 | Newdata_sigTwo Models |
| rs41257208 | 6 | 113648200 | BOD1L | ENSBTAG00000004316 | A/G | 508527 | Abo-Ismail_et_al_2014 | 3_prime_UTR_variant | | | Newdata_sig10 | . |
| rs41629678 | 1 | 138644549 | KCNH8 | ENSBTAG00000012798 | T/C | 618639 | Abo-Ismail_et_al_2014 | synonymous_variant | | | Newdata_sig10 | Newdata_sigTwo Models |
| rs41756519 | 15 | 34754872 | GRAMD1B | ENSBTAG00000001410 | T/C | 517332 | Serão et al. BMC Genetics 2013, 14:94 | Splice Region | — | | Newdata_sig10 | . |
| rs41772016 | 15 | 51796947 | LOC618173 | ENSBTAG00000005070 | T/G | 618173 | Lindholm-Perry_et_2015 | | | | Newdata_sig10 | Newdata_sigTwo Models |
| rs41820824 | 16 | 68690299 | HMCN1 | ENSBTAG00000015235 | C/T | 521326 | Abo-Ismail_et_al_2014 | SPLICE_SITE | — | | Newdata_sig10 | . |
| rs41821545 | 16 | 68672449 | HMCN1 | ENSBTAG00000002730 | A/C | 784720 | Abo-Ismail_et_al_2014 | Missense | | | Newdata_sig10 | . |
| rs42190891 | 29 | 46550309 | LRP5 | ENSBTAG00000005903 | A/G | 534450 | Karisa_et_al_2014 | missense_variant | 1 | tolerated | Newdata_sig10 | Newdata_sigTwo Models |
| rs42342962 | 23 | 45276782 | PAK1IP1 | ENSBTAG00000018674 | C/T | 505125 | Serão et al. BMC Genetics 2013, 14:94 | Missense | 1 | | Newdata_sig10 | . |
| rs42562042 | 15 | 36160748 | PLEKHA7 | ENSBTAG00000006974 | G/T | 528261 | Karisa_et_al_2014 | Missense | 0.66 | tolerated | Newdata_sig10 | . |
| rs42573278 | 16 | 65065063 | RGSL1 | ENSBTAG00000018220 | G/C | 509065 | Abo-Ismail_et_al_2014 | missense_variant | 0.36 | tolerated | Newdata_sig10 | . |
| rs43330774 | 2 | 136261151 | NECAP2 | ENSBTAG000... | G/A | 509439 | Karisa_et_al_2014 | Splice Region | — | | Newdata_sig10 | . |

TABLE 12-continued

| NCBI_dbSNP_rs_ID | Chromosome Name | Base Pair Position | Gene Name | Ensembl Gene ID | Alleles | Entrez Gene ID | Author for reference population | Variant Type | SIFT value | SIFT prediction | Example 3_62SNPs | Example 4_72SNPs |
|---|---|---|---|---|---|---|---|---|---|---|---|---|
| rs437019228 | 17 | 66535047 | CORO1C | ENSBTAG00000013282 | G/A | 515798 | Abo-Ismail_et_al_2014 | missense_variant | 1 | tolerated | Newdata_sig10 | Newdata_sigTwo Models |
| rs439445177 | 25 | 14699511 | LOC515570 | ENSBTAG00000007993 | C/T | 515570 | Yao_et_al_2013 | | | deleterious | . | . |
| rs43242284 | 1 | 67635588 | PARP14 | ENSBTAG00000017759 | G/A | 540789 | Karisa_et_al_2014 | Missense | 0.04 | deleterious | . | . |
| rs110746934 | 1 | 136620597 | RAB6B | ENSBTAG00000016656 | G/A | 526526 | Serão et al. BMC Genetics 2013, 14:94 | Splice Region | — | | . | . |
| rs384044855 | 1 | 137993085 | UBA5 | ENSBTAG00000000905 | T/A | 509292 | Karisa_et_al_2014 | missense_variant | 0.18 | tolerated | . | . |
| rs137771776 | 1 | 138084824 | ACAD11 | ENSBTAG00000004495 | G/A | 526956 | Karisa_et_al_2014 | Missense | 0 | deleterious | . | . |
| rs43277176 | 1 | 142934135 | BACE2 | ENSBTAG00000003110 | C/T | 534774 | Abo-Ismail_et_al_2014 | synonymous_variant | 0.59 | tolerated | . | . |
| rs17870910 | 2 | 6611059 | ASNSD1 | ENSBTAG00000000394 | C/T | 539672 | Karisa_et_al_2014 | missense_variant | 0.33 | tolerated | . | . |
| rs43307594 | 2 | 42036571 | GALNT13 | ENSBTAG00000005562 | C/T | 532545 | Abo-Ismail_et_al_2014 | synonymous_variant | 0.6 | tolerated | . | . |
| rs136066715 | 2 | 89549796 | AOX1 | ENSBTAG00000009725 | G/A | 338074 | Karisa_et_al_2014 | Missense | 0.33 | tolerated | . | . |
| rs134515132 | 2 | 89549850 | AOX1 | ENSBTAG00000009725 | G/A | 338074 | Karisa_et_al_2014 | Missense | 0.6 | tolerated | . | . |
| rs133016801 | 2 | 89550348 | AOX1 | ENSBTAG00000009725 | A/G | 338074 | Karisa_et_al_2014 | Missense | 1 | tolerated | . | . |

TABLE 12-continued

| NCBI_dbSNP_rs_ID | Chromosome Name | Base Pair Position | Gene Name | Ensembl Gene ID | Alleles | Entrez Gene ID | Author for reference population | Variant Type | SIFT value | SIFT prediction | Example 3_62SNPs | Example 4_72SNPs |
|---|---|---|---|---|---|---|---|---|---|---|---|---|
| rs134892794 | 2 | 89550355 | AOX1 | ENSBTAG00000009725 | C/A | 338074 | Karisa_et_al_2014 | Missense | 1 | tolerated | . | . |
| rs137383727 | 2 | 89550367 | AOX1 | ENSBTAG00000009725 | A/G | 338074 | Karisa_et_al_2014 | Missense | 0.7 | tolerated | . | . |
| rs109437938 | 2 | 89562194 | AOX1 | ENSBTAG00000009725 | G/A | 338074 | Karisa_et_al_2014 | Missense | 0.25 | tolerated | . | . |
| rs109231130 | 2 | 105138883 | SMARCAL1 | ENSBTAG00000003843 | G/C | 338072 | Karisa_et_al_2014 | Missense | 0.61 | tolerated | . | . |
| rs110703596 | 2 | 133933240 | PQLC2 | ENSBTAG00000013650 | T/C | 512930 | Karisa_et_al_2014 | Missense | 0.68 | tolerated-low confidence | . | . |
| rs380858825 | 2 | 133933915 | PQLC2 | ENSBTAG00000013650 | G/A | 512930 | Karisa_et_al_2014 | Missense | . | deleterious-low confidence | . | . |
| rs209148339 | 2 | 133935523 | PQLC2 | ENSBTAG00000013650 | T/C | 512930 | Karisa_et_al_2014 | Missense | 0.21 | tolerated-low confidence | . | . |
| rs211650382 | 3 | 7809972 | ATF6 | ENSBTAG00000005227 | C/T | 530610 | | Missense | 0.42 | tolerated | . | . |
| rs42417924 | 3 | 70997059 | LRRIQ3 | ENSBTAG00000019401 | C/G | 523789 | Abo-Ismail_et_al_2014 | 3_prime_UTR_variant | | | . | . |
| rs42317715 | 4 | 81074177 | SUGCT | ENSBTAG00000032121 | T/C | 100125578 | Abo-Ismail_et_al_2014 | SPLICE_SITE | | | . | . |
| rs137095760 | 4 | 106138003 | MGAM | ENSBTAG00000046152 | T/G | 100336421 | Rolf_et_al_2011 | | 0.01 | deleterious | . | . |
| rs109499238 | 5 | 112922677 | CHADL | ENSBTAG00000012481 | A/C/G/T | 616055 | Abo-Ismail_et_al_2014 | missense_variant | 0.13 | tolerated | . | . |
| rs134225543 | 6 | 37896750 | PPM1K | ENSBTAG00000 | C/T | 540329 | Abo-Ismail_et_al_2014 | 3_prime_UTR_variant | | | . | . |

TABLE 12-continued

| NCBI_dbSNP_rs_ID | Chromosome Name | Base Pair Position | Gene Name | Ensembl Gene ID | Alleles | Entrez Gene ID | Author for reference population | Variant Type | SIFT value | SIFT prediction | Example 3_62SNPs | Example 4_72SNPs |
|---|---|---|---|---|---|---|---|---|---|---|---|---|
| rs43702346 | 6 | 38048024 | PKD2 | ENSBTAG00000005754 | G/T | 530393 | Abo-Ismail_et_al_2014 | synonymous_variant | | | . | . |
| rs384300699 | 7 | 17044598 | PRKCSH | ENSBTAG00000020031 | G/A | 338067 | Rolf_et_al_2011 | | | deleterious | . | . |
| rs109557839 | 7 | 23867466 | ACSL6 | ENSBTAG00000008202 | G/A | 506059 | Saatchi_et_al_2014 | | | deleterious | . | . |
| rs109727850 | 7 | 98485261 | CAST | ENSBTAG00000019708 | A/G | 281039 | Karisa_et_al_2014 | Missense | 0.01 | | . | . |
| rs133057384 | 7 | 98551339 | CAST | ENSBTAG00000008074 | G/A | 281039 | Karisa_et_al_2014 | Splice Region | 0.82 | tolerated | . | . |
| rs110711318 | 7 | 98563483 | CAST | ENSBTAG00000008074 | C/T | 281039 | Karisa_et_al_2014 | Splice Region | — | | . | . |
| rs136892391 | 8 | 10456250 | ELP3 | ENSBTAG00000002730 | G/A/C/T | 784720 | Abo-Ismail_et_al_2014 | 3_prime_UTR_variant | — | | . | . |
| rs43593167 | 9 | 32473266 | FAM184A | ENSBTAG00000015467 | C/T | 541122 | Abo-Ismail_et_al_2014 | synonymous_variant | | | . | . |
| rs451808712 | 9 | 101960877 | C6orf118 | ENSBTAG00000015485 | A/C | 515846 | Rolf_et_al_2011 | | | deleterious | . | . |
| rs137496481 | 10 | 49901757 | ANXA2 | ENSBTAG00000009615 | C/T | 282689 | Abo-Ismail_et_al_2014 | synonymous_variant | | | . | . |
| rs471723345 | 10 | 49904259 | ANXA2 | ENSBTAG00000009615 | G/A | 282689 | Abo-Ismail_et_al_2014 | 3_prime_UTR_variant | | | . | . |
| rs208224478 | 10 | 7338928 | RAB15 | ENSBTAG00000003474 | C/A/G/T | 614507 | Abo-Ismail_et_al_2014 | 3_prime_UTR_variant | | | . | . |

TABLE 12-continued

| NCBI_dbSNP_rs_ID | Chromosome Name | Base Pair Position | Gene Name | Ensembl Gene ID | Alleles | Entrez Gene ID | Author for reference population | Variant Type | SIFT value | SIFT prediction | Example 3_62SNPs | Example 4_72SNPs |
|---|---|---|---|---|---|---|---|---|---|---|---|---|
| rs110711078 | 11 | 389115 | MERTK | ENSBTAG00000005828 | A/C/G/T | 504429 | Abo-Ismail_et_al_2014 | synonymous_variant | | | . | . |
| rs42275280 | 11 | 4671286 | AFF3 | ENSBTAG00000012449 | C/T | 787488 | Yao_et_al_2013 | | 0.01 | deleterious | . | . |
| rs43673198 | 11 | 28809663 | ATP6V1E2 | ENSBTAG00000013734 | T/C | 540113 | Abo-Ismail_et_al_2014 | 5_prime_UTR_variant | | | . | . |
| rs441516506 | 11 | 38706801 | CCDC85A | ENSBTAG00000012394 | G/A | 525800 | Rolf_et_al_2011 | | | | . | . |
| rs133716845 | 12 | 83085664 | ERCC5 | ENSBTAG00000014043 | C/T | 509602 | Abo-Ismail_et_al_2014 | synonymous_variant | | | . | . |
| rs41745621 | 15 | 5680312 | | ENSBTAG00000019309 | G/A | 512287 | Abo-Ismail_et_al_2014 | synonymous_variant | | | . | . |
| rs42544329 | 15 | 9690877 | CNTN5 | ENSBTAG00000020466 | G/T | 538198 | Abo-Ismail_et_al_2014 | synonymous_variant | | | . | . |
| rs42235500 | 15 | 17415692 | ELMOD1 | ENSBTAG00000002691 | G/A | 768233 | Serão et al. BMC Genetics 2013, 14:94 | Splice Region | — | | . | . |
| rs449702015 | 15 | 32674668 | SORL1 | ENSBTAG00000014611 | C/T | 533166 | Abo-Ismail_et_al_2014 | | 0.01 | deleterious | . | . |
| rs208805443 | 15 | 32681447 | SORL1 | ENSBTAG00000014611 | G/A | 533166 | Abo-Ismail_et_al_2014 | missense_variant | 0.54 | tolerated | . | . |
| rs41761878 | 15 | 42385243 | ZBED5 | ENSBTAG00000010568 | T/C | 539898 | Abo-Ismail_et_al_2014 | synonymous_variant | | | . | . |
| rs42536153 | 15 | 79136152 | LOC514818 | ENSBTAG00000005914 | G/A | 514818 | Rolf_et_al_2011 | | | deleterious | . | . |
| rs41816109 | 16 | 65097642 | RNASEL | ENSBTAG00000... | A/C | 100048947 | Abo-Ismail_et_al_2014 | 3_prime_UTR_variant | | | . | . |

TABLE 12-continued

| NCBI_dbSNP_rs_ID | Chromosome Name | Base Pair Position | Gene Name | Ensembl Gene ID | Alleles | Entrez Gene ID | Author for reference population | Variant Type | SIFT value | SIFT prediction | Example 3_62SNPs | Example 4_72SNPs |
|---|---|---|---|---|---|---|---|---|---|---|---|---|
| rs41817045 | 16 | 65111693 | RNASEL | ENSBTAG00000090091 | T/C | 100048947 | Abo-Ismail_et_al_2014 | synonymous_variant | | | . | . |
| rs210219754 | 17 | 63702804 | RPH3A | ENSBTAG00000090091 | C/A/G/T | 282044 | Abo-Ismail_et_al_2014 | synonymous_variant | | | . | . |
| rs476872493 | 19 | 36758184 | CACNA1G | ENSBTAG00000009835 | G/A | 282411 | Abo-Ismail_et_al_2014 | | | deleterious | . | . |
| rs41920005 | 19 | 51384984 | FASN | ENSBTAG00000015980 | C/G | 281152 | | 5 Prime UTR | | | . | . |
| rs41919993 | 19 | 51397250 | FASN | ENSBTAG00000015980 | T/C | 281152 | | Missense | 0.62 | tolerated | . | . |
| rs41919985 | 19 | 51402032 | FASN | ENSBTAG00000015980 | G/A | 281152 | | Missense | 0.14 | tolerated | . | . |
| rs137133778 | 20 | 10159258 | OCLN | ENSBTAG00000000561 | T/A | 512405 | Karisa_et_al_2014 | Splice Region | — | | . | . |
| rs109960657 | 20 | 10193691 | OCLN | ENSBTAG00000000561 | G/A | 512405 | Karisa_et_al_2014 | 5 Prime UTR | — | | . | . |
| rs109300983 | 20 | 31891050 | GHR | ENSBTAG00000001335 | T/C | 280805 | Karisa_et_al_2014 | Missense | 0.09 | tolerated | . | . |
| rs110265189 | 20 | 31891130 | GHR | ENSBTAG00000001335 | T/G | 280805 | Karisa_et_al_2014 | Missense | 0.02 | deleterious | . | . |
| rs109332450 | 20 | 38200470 | UGT3A1 | ENSBTAG00000002701 | C/T | 537188 | Karisa_et_al_2014 | Missense | 0.09 | tolerated | . | . |
| rs134703045 | 20 | 38204849 | UGT3A1 | ENSBTAG00000002701 | A/C | 537188 | Karisa_et_al_2014 | Splice Region | — | | . | . |

TABLE 12-continued

| NCBI_dbSNP_rs_ID | Chromosome Name | Base Pair Position | Gene Name | Ensembl Gene ID | Alleles | Entrez Gene ID | Author for reference population | Variant Type | SIFT value | SIFT prediction | Example 3_62SNPs | Example 4_72SNPs |
|---|---|---|---|---|---|---|---|---|---|---|---|---|
| rs135350417 | 20 | 38205025 | UGT3A1 | ENSBTAG00000002701 | T/C | 537188 | Karisa_et_al_2014 | Missense | 0.48 | tolerated | . | . |
| rs41946086 | 20 | 39867446 | SLC45A2 | ENSBTAG00000018235 | G/A | 538746 | Karisa_et_al_2014 | Missense | 1 | tolerated | . | . |
| rs208239648 | 22 | 17961710 | LMCD1 | ENSBTAG00000005431 | C/A/G/T | 540474 | Abo-Ismail_et_al_2014 | missense_variant | 0.15 | tolerated-low confidence | . | . |
| rs132658346 | 22 | 57050048 | TMEM40 | ENSBTAG00000000161 | A/G | 505490 | Serão et al. BMC Genetics 2013, 14:94 | Missense | 0.99 | tolerated | . | . |
| rs110700273 | 25 | 34725002 | POR | ENSBTAG00000017082 | C/T | 532512 | Abo-Ismail_et_al_2014 | missense_variant | 0.21 | tolerated | . | . |
| rs109558734 | 26 | 47854998 | MKI67 | ENSBTAG00000002444 | C/G | 513220 | Karisa_et_al_2014 | Missense | — | | . | . |
| rs135814528 | 27 | 37070184 | C27H8orf40 | ENSBTAG00000000979 | A/G | 515895 | Abo-Ismail_et_al_2014 | 3_prime_UTR_variant | | | . | . |
| rs475737617 | 27 | 37328535 | HOOK3 | ENSBTAG00000007634 | C/G | 524648 | Rolf_et_al_2011 | | | deleterious | . | . |
| rs209765899 | 28 | 14993619 | PHYHIPL | ENSBTAG00000010947 | T/A | 780878 | Abo-Ismail_et_al_2014 | synonymous_variant | | | . | . |
| rs42402428 | 29 | 6461861 | TYR | ENSBTAG00000011813 | C/T | 280951 | Abo-Ismail_et_al_2014 | synonymous_variant | | | . | . |

TABLE 13

| DMI Panel | | | RFI Panel | | |
|---|---|---|---|---|---|
| SNPID | Chr | Position | SNPID | Chr | Position |
| RS108968214 | 24 | 59670860 | RS108968214 | 24 | 59670860 |
| RS108991273 | 2 | 68111186 | RS108991273 | 2 | 68111186 |
| RS108994622 | 20 | 35521670 | RS108994622 | 20 | 35521670 |
| RS109305471 | 7 | 26329353 | RS109305471 | 7 | 26329353 |
| RS109314460 | 4 | 117907734 | RS109314460 | 4 | 117907734 |
| RS109382589 | 2 | 105158290 | RS109382589 | 2 | 105158290 |
| RS109384915 | 7 | 98554459 | RS109384915 | 7 | 98554459 |
| RS109575847 | 14 | 5603441 | RS109575847 | 14 | 5603441 |
| RS109930382 | 26 | 47852501 | RS109930382 | 26 | 47852501 |
| RS110216983 | 26 | 47852389 | RS110216983 | 26 | 47852389 |
| RS110362902 | 6 | 37994986 | RS110362902 | 6 | 37994986 |
| RS110547220 | 14 | 9508873 | RS110547220 | 14 | 9508873 |
| RS110632853 | 4 | 106144905 | RS110632853 | 4 | 106144905 |
| RS110712559 | 7 | 98560787 | RS110712559 | 7 | 98560787 |
| RS132717265 | 4 | 117658647 | RS132717265 | 4 | 117658647 |
| RS132883023 | 5 | 30159194 | RS132883023 | 5 | 30159194 |
| RS133015776 | 14 | 9443813 | RS133015776 | 14 | 9443813 |
| RS133269500 | 14 | 9469795 | RS133269500 | 14 | 9469795 |
| RS134264563 | 20 | 10167825 | RS134264563 | 20 | 10167825 |
| RS207525537 | 6 | 105377905 | RS207525537 | 6 | 105377905 |
| RS208204723 | 2 | 133933770 | RS208204723 | 2 | 133933770 |
| RS208270150 | 1 | 138045480 | RS208270150 | 1 | 138045480 |
| RS208328542 | 27 | 37068760 | RS208328542 | 27 | 37068760 |
| RS208660945 | 2 | 105170755 | RS208660945 | 2 | 105170755 |
| RS208793983 | 14 | 23155663 | RS208793983 | 14 | 23155663 |
| RS211555481 | 16 | 68490341 | RS211555481 | 16 | 68490341 |
| RS29010201 | 18 | 50581375 | RS29010201 | 18 | 50581375 |
| RS29010895 | 6 | 38042011 | RS29010895 | 6 | 38042011 |
| RS378496139 | 20 | 35942739 | RS378496139 | 20 | 35942739 |
| RS378726699 | 23 | 32030037 | RS378726699 | 23 | 32030037 |
| RS382292677 | 11 | 6039571 | RS382292677 | 11 | 6039571 |
| RS384020496 | 7 | 98535716 | RS384020496 | 7 | 98535716 |
| RS385640152 | 20 | 31909478 | RS385640152 | 20 | 31909478 |
| RS41257208 | 6 | 113648200 | RS41257208 | 6 | 113648200 |
| RS41574929 | 6 | 35938366 | RS41574929 | 6 | 35938366 |
| RS41580312 | 20 | 35544340 | RS41580312 | 20 | 35544340 |
| RS41629678 | 1 | 138644549 | RS41629678 | 1 | 138644549 |
| RS41756484 | 15 | 34750064 | RS41756484 | 15 | 34750064 |
| RS41756519 | 15 | 34754872 | RS41756519 | 15 | 34754872 |
| RS41772016 | 15 | 51796947 | RS41772016 | 15 | 51796947 |
| RS41820824 | 16 | 68690299 | RS41820824 | 16 | 68690299 |
| RS41821545 | 16 | 68672449 | RS41821545 | 16 | 68672449 |
| RS41821600 | 16 | 68614446 | RS41821600 | 16 | 68614446 |
| RS41824268 | 16 | 68409088 | RS41824268 | 16 | 68409088 |
| RS42190891 | 29 | 46550309 | RS42190891 | 29 | 46550309 |
| RS42345570 | 20 | 38200342 | RS42345570 | 20 | 38200342 |
| RS42562042 | 15 | 36160748 | RS42562042 | 15 | 36160748 |
| RS42573278 | 16 | 65065063 | RS42573278 | 16 | 65065063 |
| RS43285609 | 1 | 146449085 | RS43285609 | 1 | 146449085 |
| RS43330774 | 2 | 136261151 | RS43330774 | 2 | 136261151 |
| RS43563315 | 22 | 57056954 | RS43563315 | 22 | 57056954 |
| RS43657898 | 11 | 3589846 | RS43657898 | 11 | 3589846 |
| RS437019228 | 17 | 66535047 | RS437019228 | 17 | 66535047 |
| RS438856835 | 2 | 41791856 | RS438856835 | 2 | 41791856 |
| RS445312693 | 1 | 146457394 | RS445312693 | 1 | 146457394 |
| snp113359 | 13 | 77836421 | snp113327 | 13 | 77390382 |
| snp116465 | 14 | 24285472 | snp120187 | 15 | 4643341 |
| snp120246 | 15 | 5596597 | snp 121741 | 15 | 26880589 |
| snp155060 | 18 | 64878369 | snp148414 | 18 | 45788371 |
| snp190398 | 24 | 41961677 | snp 160039 | 19 | 32790843 |
| snp193208 | 25 | 9474324 | snp160183 | 19 | 34024573 |
| snp201742 | 26 | 49707892 | snp160576 | 19 | 36083884 |
| snp208418 | 28 | 44512171 | snp 160577 | 19 | 36084009 |
| snp213198 | 29 | 43964483 | snp166503 | 20 | 4791751 |
| snp32714 | 4 | 26490406 | snp167616 | 20 | 22382661 |
| snp44601 | 5 | 68875631 | snp 171506 | 21 | 21904160 |
| snp54468 | 6 | 94123737 | snp176625 | 22 | 11756783 |
| snp54469 | 6 | 94130313 | snp207577 | 28 | 34631416 |
| snp54769 | 6 | 95719829 | snp213663 | 29 | 45207689 |
| snp64233 | 7 | 49155508 | snp31738 | 4 | 7433019 |
| snp68885 | 8 | 10013895 | snp56474 | 6 | 118336049 |
| snp73653 | 8 | 83652278 | snp67833 | 7 | 111291704 |
| snp73656 | 8 | 83674570 | snp90343 | 10 | 87108872 |
| snp79504 | 9 | 71750710 | snp92282 | 11 | 7268172 |
| snp79505 | 9 | 71750734 | snp98219 | 11 | 97092757 |

What is claimed is:

1. A method for producing meat from or breeding a *Bos taurus* animal having increased feed efficiency, the method comprising:
    obtaining nucleic acid samples from members of a population of *Bos taurus* animals;
    genotyping the samples to detect alleles of single nucleotide polymorphisms (SNPs) in a panel of SNPs for each member of the population, wherein the panel of SNPs comprises rs109382589, rs208660945, rs43702346, rs137601357, rs210072660, rs133057384, rs41821600, rs476872493, rs134264563, rs385640152, rs43020736, rs110216983, rs109930382, rs109558734, and rs209765899;
    assigning a molecular breeding value to each animal in the population, wherein the molecular breeding value is calculated from allele substitution effects on at least one feed efficiency phenotype for each detected allele in the SNP panel for the animal, and wherein the at least one feed efficiency phenotype comprises Residual Feed Intake (RFI) and/or Residual Feed Intake adjusted for backfat (RFIf); and
    producing meat from and/or breeding a *Bos taurus* animal from the population having a molecular breeding value in the top 16% of the population.

2. The method of claim 1, wherein the panel is less than 250 SNPs.

3. The method of claim 1, wherein the genotyping comprises extracting and/or amplifying DNA from the sample and contacting the DNA with an array comprising at least one probe suitable for determining the identity of the allele at each of said SNPs.

4. The method of claim 3, wherein the array is a DNA array, a DNA microarray or a bead array.

5. The method of claim 1, wherein the genotyping comprises amplifying a region of the nucleic acid sample using an oligonucleotide primer pair, to form nucleic acid amplification products comprising said SNPs.

6. The method of claim 5, wherein at least one primer of said oligonucleotide primer pair comprises at least 10 contiguous sequences flanking said SNPs.

7. The method of claim 1, further comprising genotyping the samples to detect alleles of SNPs comprising: rs109065702, rs109808135, rs110348122, rs42417924, rs110632853, rs110519795, rs132717265, rs109499238, rs134225543, rs110362902, rs29010894, rs207525537, rs384020496, rs110711318, rs137400016, rs471723345, rs43657898, rs42275280, rs43673198, rs110323635, rs109575847, rs133269500, rs110547220, rs109800133, rs42544329, rs42235500, rs211555481, rs381726438, rs209012152, rs210494625, rs209439233, rs207541156, rs41947101, rs134604394, rs41946086, rs133838809, rs132658346, rs42342962, and rs135814528.

8. The method of claim 1, further comprising genotyping the samples to detect alleles of SNPs comprising: comprises rs132717265, rs43657898, rs211555481, rs110362902, rs109800133, rs134604394, rs29010894, rs207525537, rs110348122, rs109808135, rs384020496, rs137400016, rs110519795, rs42342962, rs381726438, rs207541156, rs109065 702, rs133838809, rs133269500, rs109575847, rs209439233, rs110632853, rs41947101, rs110547220, rs209012152, rs210494625, and rs110323635.

9. The method of claim 1, further comprising genotyping the samples to detect alleles of SNPs comprising: comprises rs43242284, rs110953962, rs110746934, rs384044855, rs210293774, rs208270150, rs137771776, rs41629678, rs43277176, rs43285609, rs445312693, rs17870910, rs450068075, rs438856835, rs43307594, rs108991273, rs136066715, rs134515132, rs133016801, rs134892794, rs137383727, rs109437938, rs109065702, rs109808135, rs109231130, rs110348122, rs110703596, rs208204723, rs380858825, rs209148339, rs43330774, rs211650382, rs42417924, rs42317715, rs29004488, rs137095760, rs110632853, rs110519795, rs132717265, rs109314460, rs132883023, rs109392049, rs109499238, rs41574929, rs134225543, rs110362902, rs29010895, rs29010894, rs207525537, rs41257208, rs384300699, rs109557839, rs109305471, rs109727850, rs384020496, rs109384915, rs110712559, rs110711318, rs136892391, rs137400016, rs43593167, rs451808712, rs137496481, rs471723345, rs208224478, rs110711078, rs43657898, rs42275280, rs382292677, rs43673198, rs441516506, rs133716845, rs110323635, rs109575847, rs133015776, rs133269500, rs110547220, rs208793983, rs109800133, rs41745621, rs42544329, rs42235500, rs449702015, rs208805443, rs41756484, rs41756519, rs42562042, rs41761878, rs41772016, rs43705159, rs109778625, rs42536153, rs42573278, rs41816109, rs41817045, rs109345460, rs109961941, rs41824268, rs211555481, rs209074324, rs381726438, rs209012152, rs210494625, rs209439233, rs41821545, rs41820824, rs210219754, rs437019228, rs29010201, rs41920005, rs41919993, rs41919985, rs137133778, rs109638814, rs109960657, rs207541156, rs109300983, rs209676814, rs110265189, rs108994622, rs41580312, rs41947101, rs378496139, rs42345570, rs109332450, rs134703045, rs135350417, rs133951891, rs134604394, rs41946086, rs208239648, rs133838809, rs132658346, rs43563315, rs378726699, rs42342962, rs108968214, rs439445177, rs110700273, rs208328542, rs135814528, rs475737617, rs42402428, and rs42190891.

10. The method of claim 1, wherein the panel of SNPs further comprises rs109065702, rs109314460, rs109392049, rs109575847, rs109800133, rs109808135, rs110323635, rs110348122, rs110362902, rs110519795, rs110547220, rs110632853, rs110712559, rs110953962, rs132717265, rs132883023, rs133269500, rs133838809, rs134604394, rs137400016, rs207525537, rs207541156, rs208270150, rs208328542, rs208793983, rs209012152, rs209074324, rs209439233, rs210494625, rs211555481, rs29004488, rs29010894, rs378496139, rs381726438, rs384020496, rs41574929, rs41580312, rs41756484, rs41824268, rs41947101, rs42345570, rs43285609, rs43563315, rs43657898, rs43705159, rs438856835, rs445312693, rs450068075, rs109345460, rs109384915, rs109638814, rs209676814, rs210293774, rs29010201, rs29010895, rs378726699, rs382292677, rs41629678, rs41772016, rs42190891, and rs437019228.

11. The method of claim 1, further comprising genotyping the samples to detect alleles of SNPs comprising: comprises rs110953962, rs41574929, rs29010894, rs471723345, rs42544329, rs207541156, and rs208239648.

12. The method of claim 1, further comprising genotyping the samples to detect alleles of SNPs comprising: comprises rs210293774, rs208270150, rs109065702, rs109808135, rs42417924, rs134225543, rs384020496, rs137400016, rs43673198, rs133716845, rs133269500, rs110547220, rs209012152, rs134604394, rs41946086, and rs208239648.

13. The method of claim 1, further comprising genotyping the samples to detect alleles of SNPs comprising: comprises rs210293774, rs208270150, rs133716845, rs41946086, and rs208239648.

14. The method of claim 1, further comprising genotyping the samples to detect alleles of SNPs comprising: comprises rs210293774, rs208270150, rs109065702, rs109808135, rs134225543, rs384020496, rs137400016, rs43673198, rs133269500, rs110547220, rs209012152, rs134604394, rs41946086, and rs208239648.

15. The method of claim 1, further comprising genotyping the samples to detect alleles of SNPs comprising: comprises rs43285609, rs438856835, rs42417924, rs110519795, rs132717265, rs134225543, rs384020496, rs110711318, rs42275280, rs133716845, rs110323635, rs133269500, rs42235500, rs42345570, rs134604394, and rs135814528.

16. The method of claim 1, further comprising genotyping the samples to detect alleles of SNPs comprising: comprises rs43285609, rs438856835, rs132717265, rs134225543, rs384020496, rs110711318, rs42235500, rs42345570, and rs135814528.

17. The method of claim 1, further comprising genotyping the samples to detect alleles of SNPs comprising: comprises rs108968214, rs108991273, rs108994622, rs109305471, rs109314460, rs109384915, rs109575847, rs110362902, rs110547220, rs110632853, rs110712559, rs132717265, rs132883023, rs133015776, rs133269500, rs207525537, rs208204723, rs208270150, rs208328542, rs208793983, rs211555481, rs29010201, rs29010895, rs378496139, rs378726699, rs382292677, rs384020496, rs41257208, rs41574929, rs41580312, rs41629678, rs41756484, rs41756519, rs41772016, rs41820824, rs41821545, rs41824268, rs42190891, rs42345570, rs42562042, rs42573278, rs43285609, rs43330774, rs43563315, rs43657898, rs437019228, rs438856835, and rs445312693.

18. The method of claim 1, wherein said panel is 200 or less SNPs.

19. The method of claim 1, wherein said panel is 100 or less SNPs.

20. The method of claim 1, wherein said panel is 70 or less SNPs.

21. The method of claim 1, wherein said panel is 60 or less SNPs.

22. The method of claim 1, wherein said panel is 50 or less SNPs.

23. The method of claim 1, wherein said panel is 40 or less SNPs.

* * * * *